US012692301B2

(12) United States Patent
Sikorski et al.

(10) Patent No.: US 12,692,301 B2
(45) **Date of Patent: *Jul. 28, 2026**

(54) METHODS OF IMPROVING RETINA-ASSOCIATED DISEASE OUTCOME USING CCR3-INHIBITORS

(71) Applicant: ALKAHEST INC., San Carlos, CA (US)

(72) Inventors: Bartosz Sikorski, Bydgoszcz (PL); Elizabeth W. Jeffords, San Carlos, CA (US); Erin McCaskill Newman, San Carlos, CA (US); Jessica A. Powell, San Carlos, CA (US); Esther Rawner, San Carlos, CA (US)

(73) Assignee: ALKAHEST INC., San Carlos, CA (US)

( * ) Notice: Subject to any disclaimer, the term of this patent is extended or adjusted under 35 U.S.C. 154(b) by 606 days.

This patent is subject to a terminal disclaimer.

(21) Appl. No.: 18/009,408

(22) PCT Filed: Jun. 9, 2021

(86) PCT No.: PCT/US2021/036641

§ 371 (c)(1), (2) Date: Dec. 9, 2022

(87) PCT Pub. No.: WO2021/252647

PCT Pub. Date: Dec. 16, 2021

(65) Prior Publication Data

US 2023/0312697 A1 Oct. 5, 2023

Related U.S. Application Data

(60) Provisional application No. 63/040,345, filed on Jun. 17, 2020, provisional application No. 63/037,970, filed on Jun. 11, 2020.

(51) Int. Cl.

| | |
|---|---|
| ***C07K 16/22*** | (2006.01) |
| ***A61K 31/4545*** | (2006.01) |
| ***A61P 27/02*** | (2006.01) |

(52) U.S. Cl.

CPC .......... *C07K 16/22* (2013.01); *A61K 31/4545* (2013.01); *A61P 27/02* (2018.01)

(58) Field of Classification Search

CPC .......................... C07K 16/22; C07K 2317/24; A61K 31/4545; A61K 39/395; A61K 38/179; A61P 27/02

See application file for complete search history.

(56) References Cited

U.S. PATENT DOCUMENTS

| | | | | |
|---|---|---|---|---|
| 7,705,153 | B2 | 4/2010 | Ting et al. | |
| 7,935,700 | B2 | 5/2011 | Tanaka et al. | |
| 8,030,303 | B2 | 10/2011 | Masuda et al. | |
| 8,278,302 | B2 | 10/2012 | Grundl et al. | |
| 8,653,075 | B2 | 2/2014 | Grundl et al. | |
| 8,680,280 | B2 | 3/2014 | Duran et al. | |
| 8,742,115 | B2 | 6/2014 | Frank et al. | |
| RE45,323 | E | 1/2015 | Grundl et al. | |
| 9,206,186 | B2 | 12/2015 | Li et al. | |
| 9,233,950 | B2 | 1/2016 | Frank et al. | |
| 11,590,118 | B2 * | 2/2023 | Corradini | A61P 27/02 |
| 11,951,102 | B2 * | 4/2024 | Corradini | A61K 9/282 |
| 2013/0266646 | A1 | 10/2013 | Fetscher et al. | |
| 2016/0038589 | A1 | 2/2016 | Patel | |
| 2016/0081998 | A1 | 3/2016 | Nivens et al. | |
| 2016/0193217 | A1 | 7/2016 | Higashi | |
| 2017/0319567 | A1 | 11/2017 | Nivens et al. | |
| 2020/0054622 | A1 | 2/2020 | Braithwaite et al. | |
| 2020/0054745 | A1 | 2/2020 | Lashkari | |

FOREIGN PATENT DOCUMENTS

| | | | |
|---|---|---|---|
| WO | WO-2004/084898 | A1 | 10/2004 |
| WO | WO-2012/097019 | A1 | 7/2012 |
| WO | WO-2018/187473 | A1 | 10/2018 |

OTHER PUBLICATIONS

Nagai et al. "Novel CCR3 Antagonists Are Effective Mono- and Combination Inhibitors of Choroidal Neovascular Growth and Vascular Permeability" American Journal of Pathology. Jul. 2015, vol. 185. p. 2534-2549.

PCT App. No. PCT/US 21/36641; International Search Report and Written Opinion mailed Oct. 4, 2021.

Pease & Horuk, Expert Opin. Ther. Patents 19(1) (2009).

Jager, R. et al., The New England Journal of Medicine, 358(2606-17), 2008.

Pease JE and Horuk R, Expert Opin Drug Discov, 9(5):467-83 (2014).

Wise EL et al., J Biol Chem, 282(38): 27935-43 (2007).

Sabroe I, et al., J Biol Chem, 275(34): 25985-92 (2000).

Mori A. et al., Int Immunol, 19(8):913-21 (2007).

Nitta A, et al., Bioorg & Med Chem Lett, 22 6872-81 (2012).

Sato I, et al., Bioorg & Med Chem Lett, 16 144-56 (2008).

Suzuki K, et al., BBRC, 339:1217-23 (2006).

(Continued)

*Primary Examiner* — Sudhakar Katakam

(74) *Attorney, Agent, or Firm* — MARSHALL, GERSTEIN & BORUN LLP

(57) ABSTRACT

The disclosure provides a method of reducing the frequency of administration of an anti-VEGF agent to a subject diagnosed with wet age-related macular degeneration. The method comprises administering a CCR3 inhibitory agent to the subject; administering the anti-VEGF agent to the subject after the administering of the CCR3 inhibitory agent; and administering additional subsequent doses of the anti-VEGF agent to the subject at a frequency less than the recommended frequency. The disclosure further provides a method of treating a subject suffering from a retina-associated disease, the method comprising administering an anti-VEGF agent to a subject suffering from a retina-associated disease and previously treated with a CCR3 inhibitory agent, wherein the anti-VEGF agent is administered at a frequency less than the recommended frequency for the anti-VEGF agent.

9 Claims, 22 Drawing Sheets

(56) References Cited

OTHER PUBLICATIONS

Suzuki K, et al., Eur J Pharm, 563 224-32 (2007).
Morokata T et al., J Pharm Exp Ther 317(1):244-50 (2006).
Helzner J, Retinal Physician, Jun. 2020, P. E5.
Kuppermann BD et al., Ophthalmologica, 234:40-54 (2015).
Hadayer A et al., Expert Opin Drug Delivery, 13(8):1083-91 (2016).
Corpus K et al., Philipp J Ophthalmol, 40:52-56 (2015).
Quatrini L et al., Cell Mol Immunol, 18:269-78 (2021).
Desai, SJ, et al., Curr Opthalmol. Rep. (Feb. 1, 2017).
Ambati, J., et al., Neuron 75(1):26-39, Jul. 2012.
Papadopoulou DN, et al., Ophthalmology 116(9):1755-61 (2009).
Sacu S, et al., Invest. Ophthalmol. Vis. Sci. 52(6):3046-50 (2011).
Rofagha S, et al. Am. J. Ophthalmol. 159(5):915-24 (2015).
Peden MC et al., Retina Specialist, Jun:28-32 (2016).
Aflibercept (Eylea): Treatment of Neovascular (Wet) Age-Related Macular Degeneration (wAMD) [Internet]. Ottawa (ON): Canadian Agency for Drugs and Technologies in Health; 2015.
Beck RW et al., Am J Ophthalmol. 135. 194-205 (2003).
Senechal S et al., Lab Investig 82:929-39 (2002).
Williams TJ, Front. Immunol. 6(84) (2015) (CAT-213, iCo-008, Bertilimumab).
MacCumber M, Yu, JS, Sagkriotis A, et al. Injection intervals in treatment-naïve neovascular AMD patients who received anti-VEGF agents: An analysis of the IRIS Registry. American Academy of Ophthalmology, San Francisco, 2019:PO471).
Ciulla TA et al., Ophthalmology Retina, 4:19-30 (2020).
Karth PA et al., *Bevacizumab*, EyeWiki, American Academy of Ophthalmology, (2020).
Lucentis® (ranibizumab injection) for Intravitreal Injection Prescribing Information (Revised Jan. 2017).
Yang S et al., Drug Design, Development and Therapy, 10:1857-67 (2016).
Raecker ME et al., *Diagnosis and Treatment of CNV in Myopic Macular Degeneration*, EyeNet Mag, (Apr. 2015):35-37.
Bokinni, Y, et al., Eye 29:1085-91 (2015).
Fujimoto, JG, et al., *Neoplasia*, 2(1-2):9-25 (Jan. 2000).
Fingler J et al., Investig Ophthalmol Vis Sci, 49(11):5055-59 (2008).
Sousa DC et al., *Optical Coherence Tomography Angiography*, EyeWiki, American Academy of Ophthalmology (2019).
Waheed NK et al., Developments in Ophthalmology 56:91-100 (2016).
Samara WA et al., Ophthalmology, 124(2):235-44 (2017).
De Carlo TE et al., Ophthalmic Surgery, Lasers Imaging Rein. 47(2):128-33 (2016).
Wakabayashi T et al., Investig Ophthalmology Vis Sci, 58(4):2087 (2017)).
Zhang Q et al., Retina, 35(11):2285-99 (2015)).
Querques L et al., Br J Ophthalmol, 309162 (2016).
De Carlo TE et al. Int J Rein Vitr. 1(1):5 (2015).
Faridi A et al., Ophthalmol Retina, 1(4):294-303 (2017)).
Patel AV et al., Int Ophthalmol Clin, 55(4):103-12 (2015).
Martin DF et al., Ophthalmology, 119(7):1388-98 (2012).
Jang L et al., Graefes Arch Clin Exp Ophthalmol, 253(8):1211-16 (2015).
Fowler SC and Schneider EW, More frequent dosing for refractory nAMD?, Retina Specialist, May 13, 2020.
Jaffe GJ, et al., Ophthalmology, 123:1856-64 (2016)).

* cited by examiner

Figure 22

| Patient Case Number | Eye | Days Between Doses | Months Between Doses or Since Last Dose | Notes | Mean Months Without anti-VEGF Injection | Std Dev | Range | Doses Per Month | Doses Per Year |
|---|---|---|---|---|---|---|---|---|---|
| Refractory | | | | | | | | | |
| Patient Case 4 | Right Eye | 279 | 9.17 | | | | | | |
| Patient Case 4 | Right Eye | 221 | ***7.27*** | No 3rd dose | | | | 0.115 | 1.374 |
| Patient Case 4 | Left Eye | 488 | ***16.04*** | No 2nd dose | 10.83 | 4.61 | 7.27 - 16.04 | 0.057 | 0.687 |
| | | | | | | | | | |
| Naive | | | | | | | | | |
| Patient Case 1 | Right Eye | 493 | ***16.2*** | No 2nd dose | | | | 0.056 | 0.667 |
| Patient Case 2 | Right Eye | 175 | 5.75 | | | | | | |
| Patient Case 2 | Right Eye | 154 | 5.06 | | | | | | |
| Patient Case 2 | Right Eye | 108 | ***3.55*** | No 4th dose | | | | 0.197 | 2.368 |
| Patient Case 3 | Left Eye | 348 | 11.41 | | | | | | |
| Patient Case 3 | Left Eye | 187 | ***6.15*** | No 3rd dose | 8.02 | 4.81 | 3.55 - 16.2 | 0.103 | 1.231 |
| | | | | | | | | | |
| | | | *Bold-Italics indicate time since last dose where a next follow-up dose had not yet been administered at the time this data was compiled. | | | | | | |

METHODS OF IMPROVING RETINA-ASSOCIATED DISEASE OUTCOME USING CCR3-INHIBITORS

CROSS REFERENCE TO RELATED APPLICATIONS

This application is a United States national stage entry of International Patent Application No. PCT/US2021/036641, filed Jun. 9, 2021, claims priority pursuant to 35 U.S.C. § 119(e) to U.S. Provisional Application No. 63/037,970, filed Jun. 11, 2020, and U.S. Provisional Patent Application No. 63/040,345, filed Jun. 17, 2020, the disclosures of which applications are herein incorporated by reference.

BACKGROUND

Among the variety of retinal-associated diseases, there are those that manifest themselves early in life as well as those that manifest themselves in connection with aging. An example of the former type of disease is retinopathy of prematurity (ROP) and Stargardt's disease. Examples of age-related retina-associated diseases include: age-related macular degeneration (AMD) which is the most common degenerative disease of the macula; retinal vein occlusion (RVO), myopic choroidal neovascularization (mCNV) and diabetic retinopathy (with and without macular edema). Untreated, retina-associated disease can lead to legal blindness.

AMD is the leading cause of irreversible blindness in people 50 years of age or older in the developed world. (Jager, R. et al., The New England Journal of Medicine, 358(2606-17), 2008). AMD is a term that is used to describe a family of diseases that are all characterized by a progressive loss of central vision associated with abnormalities of Bruch's membrane, the choroid, the neural retina and/or the retinal pigment epithelium. In the early stages of AMD, which is often referred to as age-related maculopathy (ARM) or non-exudative or "dry" AMD (early and intermediate disease), accumulation of drusen (biochemical byproducts of the photoreceptor cells which accumulate in Bruch's membrane which are categorized by their appearance) and disturbances of the retinal pigment epithelium (RPE) are often observed.

AMD that becomes clinically advanced is classified into two forms—"dry," nonexudative or atrophic AMD called "Geographic Atrophy" and exudative "wet" (wAMD) or neovascular AMD (nAMD). Advanced dry AMD or Geographic Atrophy occurs in approximately 15% and wet AMD 10% of AMD patients. Wet AMD is considered the more immediate debilitating form of AMD and is thought to be caused by the growth of abnormal choroidal neovascular membranes (CNVM). These new blood vessels grow from the choriocapillaris, growing under the RPE or retina, and leak serum and blood. This fluid accumulates in the sub-RPE and subretinal and retinal (e.g., intraretinal fluid) spaces along with the neurosensory retina, and in turn causes measurable thickening of the macula. If the fovea becomes involved with the CNVM, the resulting edema and hemorrhage can significantly impair visual acuity (VA), leading to dramatic vision loss.

Estimates suggest that about 10% of those aged 65-74 years old and 30% of those aged 75-85+ years old, exhibit signs of AMD. The current standard of care for wet AMD is anti-angiogenic therapies such as ranibizumab (Lucentis®) and aflibercept (Eylea®) by intravitreal (IVT) administration (i.e. injection directly into the eye). Another standard of care utilized off-label is bevacizumab (Avastin®). Such therapies target vascular endothelial growth factors (VEGF, VEGF-A) and their angiogenic-promoting properties. Additional treatments targeting VEGF include brolucizumab, KSI301 (Kodiak Sciences), abicipar, GB-102, (Graybug Vision), and anti-VEGF genetic therapies such as RGX-314 (RegenxBio) and ADVM-022 (Adverum). A concentrated bevacizumab eye port delivery system and conbercept (KH902) fusion protein have also been explored. Modifications to standard of care have mostly concentrated not on identifying new targets or polypharmacy like the instant application, but ways to extend the durability or pharmacology of anti-VEGF therapies. However even these attempts (e.g., brolucizumab) at increasing the duration of doses in order to lower the per year dosing rate have been met with safety concerns (Helzner J, *Retinal Physician*, June 2020, P. E5).

Glucocorticoids delivered IVT have also been explored in patients with retina related disease. However, anti-VEGF IVT treatments have been generally associated with fewer side effects and ocular complications. (Kuppermann B D et al., *Ophthalmologica,* 234:40-54 (2015)). For example, glucocorticoids delivered IVT can have a high rate of cataract formation and steroid-induced glaucoma. (Hadayer A et al., *Expert Opin Drug Delivery,* 13(8):1083-91 (2016) and Corpus K et al., *Philipp J Ophthalmol,* 40:52-56 (2015)). Further, almost all cells in the body are sensitive to glucocorticoids, producing pleiotropic effects that are undesirable to human health. (Quatrini L et al., *Cell Mol Immunol,* 18:269-78 (2021)).

Unfortunately, monthly IVT anti-VEGF injections have been associated with the adverse effects of geographic atrophy. (Desai, S J, et al., Curr Opthalmol. Rep. (Feb. 1, 2017)). In nAMD there have been serious concerns raised of increased intraocular pressure and increased risk of glaucoma. (Fowler S C and Schneider E W, More frequent dosing for refractory nAMD?, Retina Specialist, May 13, 2020). Further, IVT injections can be associated with serious adverse events such as endophthalmitis, retinal detachment, and traumatic cataract. Currently, there exist no effective, less-invasive therapies, underscoring an unmet need for a non-IVT delivered anti-VEGF based therapy for treating AMD, such as in orally administered form. In addition to alleviating and reversing the symptoms and dramatic detrimental effects on the vision of patients, such a therapy would have the added benefit of increased compliance. IVT injections bear increased cost and risk to patients and are burdensome to both patients and caregivers. Requirements for a cold chain and prefilled vials and syringes involve substantial financial investment. And even when injections are given in a bi-monthly fashion, patients often need to visit the office of the retinal specialist more frequently for diagnostic tests to ensure the stability of the retina. Due to the state of their vision, these visits frequently involve a caregiver. Recent estimates have suggested that between drive time, wait time, treatment, recovery, and booking time, each visit can take more than 10 hours of combined time. Because of the burden on patients and care staff, physicians and patients alike have attempted to create "treat and extend regimens" which decrease the frequency of injections and visits. However, these decreased injection frequencies lead to decreased treatment outcomes over time.

In the instances where glucocorticoid therapy adjunctive to anti-VEGF treatment have been explored, both practical and safety concerns remain. Glucocorticoid (dexamethasone) implants in the eye in conjunction with anti-VEGF agents delivered IVT have exhibited modest efficacy in reducing the frequency of anti-VEGF injections in neovascular AMD; at best, the adjunct therapy allowed the interval between anti-VEGF injections to be extended by less than 30 days. Further, the eye implants release glucocorticoids continuously over the life of the implant (e.g., 3-4 months), thereby requiring constant exposure to the subject. (Kuppermann, supra.). Further, implants expire, requiring invasive reinsertion of replacement implants into patients' eyes. (Corpus, supra.)

The mechanistic basis of anti-VEGF therapies also bears risk. VEGF, particularly VEGF-A has a physiologic cytoprotective role in the retina. Modulating VEGF expression and activity can be toxic to multiple cell types. (Ambati, J., et al., Neuron 75(1):26-39, July 2012). Evidence shows that anti-VEGF-A therapy can also contribute to physiologic alterations in the retinal vasculature in the short-term as well as RPE toxicity in the long-term. (Papadopoulou D N, et al., Ophthalmology 116(9):1755-61 (2009); Sacu S, et al., Invest. Ophthalmol. Vis. Sci. 52(6):3046-50 (2011); and Rofagha S, et al. Am. J. Ophthalmol. 159(5):915-24 (2015)).

An additional drawback to the use of anti-VEGF agents such as aflibercept, ranibizumab, and bevacizumab is the need for frequent dosing such as once per month (q4 wk) or bimonthly (q8 wk) or even as frequent as twice per month. (Peden M C et al., Retina Specialist, June: 28-32 (2016)). Not only does such frequent dosing result in higher cost and repeated, invasive injections into affected eyes, but a significant number of patients have proven to have a poor or non-response to anti-VEGF agents upon standard treatment. Further, many patients have experienced a loss of efficacy of anti-VEGF agents after repeated administration over time, becoming refractory to treatment. (Id.). Persistent presence of fluid at the retina as observed by optical coherence tomography (OCT) or angiography has been observed in 51.5% of patients receiving IVT ranibizumab and in 67.4% of patients receiving IVT bevacizumab after two years of monthly injections. (Id.) Similarly, 19.7% to 36.6% of patients receiving IVT aflibercept either monthly or bimonthly have active exudation via OCT or angiography after 1 year. (Id.)

Despite the promise of anti-VEGF therapy for the treatment of retinal disorders including nAMD, there is a need for new agents and methods to overcome the drawbacks of IVT anti-VEGF agents.

SUMMARY

The methods of the disclosure are surprisingly effective at improving the outcome of IVT anti-VEGF dosing regimens by decreasing the necessary frequency of dosing of such agents in both treatment naïve and refractory patients through the use of C—C motif chemokine receptor 3 (CCR3) pathway antagonists. The methods provide a response that is unexpectedly greater in robustness and durability compared to prior methods using anti-VEGF agents, steroids or a combination of the two. Naïve patients who undergo treatment with a small molecule CCR3 antagonist in conjunction with anti-VEGF agents require significantly less frequent doses of anti-VEGF agents, while those with refractory disease surprisingly experience renewed sensitivity.

The disclosure provides methods of treating patients for retinal-associated disease, including, e.g., dry and wet age-associated macular degeneration, retinal vein occlusion, retinopathy of prematurity, diabetic retinopathy (with and without macular edema), myopic choroidal neovascularization and geographic atrophy. Aspects of the methods include treating the patient with a dosing regimen of a CCL11/CCR3 pathway antagonist and anti-VEGF agents so as to decrease the recommended frequency of anti-VEGF agents. The methods also include administering of a CCL11/CCR3 pathway antagonist to re-sensitize patients with refractory disease to anti-VEGF agents.

All publications and patent applications mentioned in this specification are herein incorporated by reference to the same extent as if each individual publication or patent application was specifically and individually indicated to be incorporated by reference.

Figure 1:
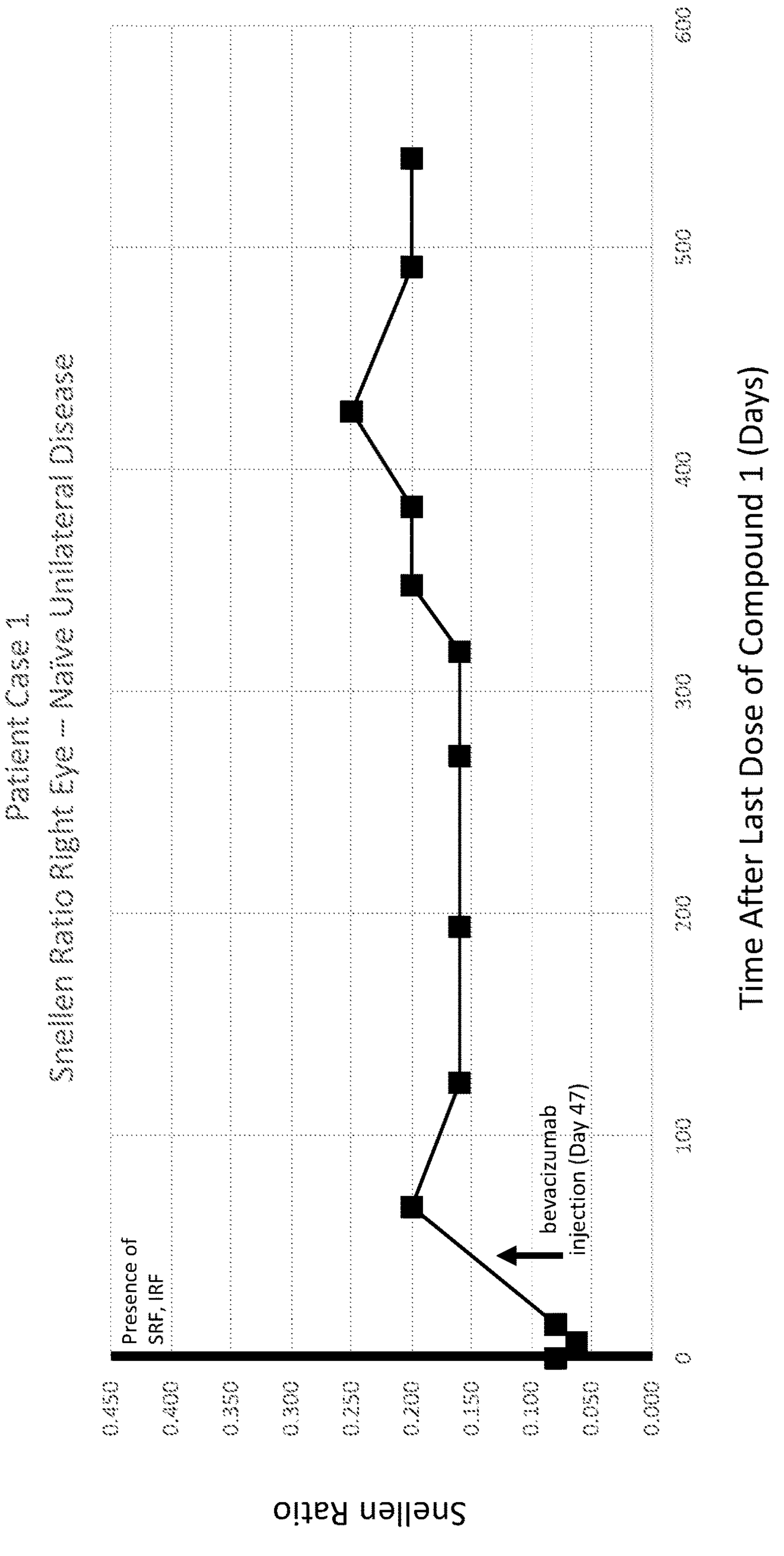
FIG. 1, FIG. 2 and FIG. 3 are graphs reporting the Snellen-based visual acuity ratio in three subjects with naïve unilateral wAMD (i.e. having wAMD in one eye). The subjects are referred to as Patient Case 1, Patient Case 2, and Patient Case 3, respectively. The x-axis depicts time after the last dose of Compound 1 CCR3 antagonist had been administered. Arrows report when an anti-VEGF agent was administered intravitreally (IVT). Notes at the top of the graph annotate changes to morphological features of the retina, particularly the fovea, leading to decision to retreat with an anti-VEGF agent. The Snellen eye chart is a commonly employed and well-recognized test of visual acuity in clinical practice. See Aflibercept (Eylea): Treatment of Neovascular (Wet) Age-Related Macular Degeneration (wAMD) [Internet]. Ottawa (ON): Canadian Agency for Drugs and Technologies in Health; 2015 August APPENDIX 5, VALIDITY OF OUTCOME MEASURES.
Figure 2:
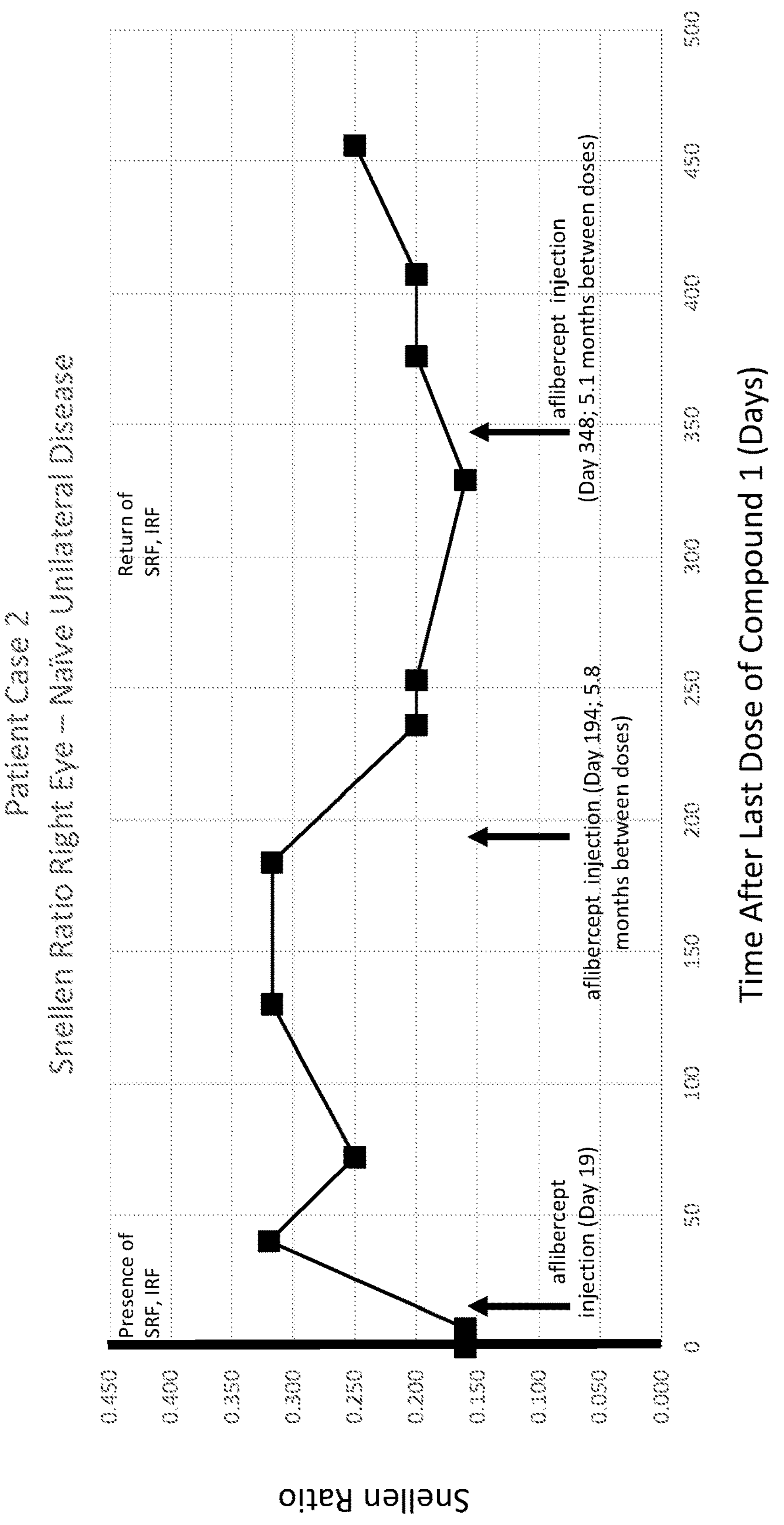
Figure 3:
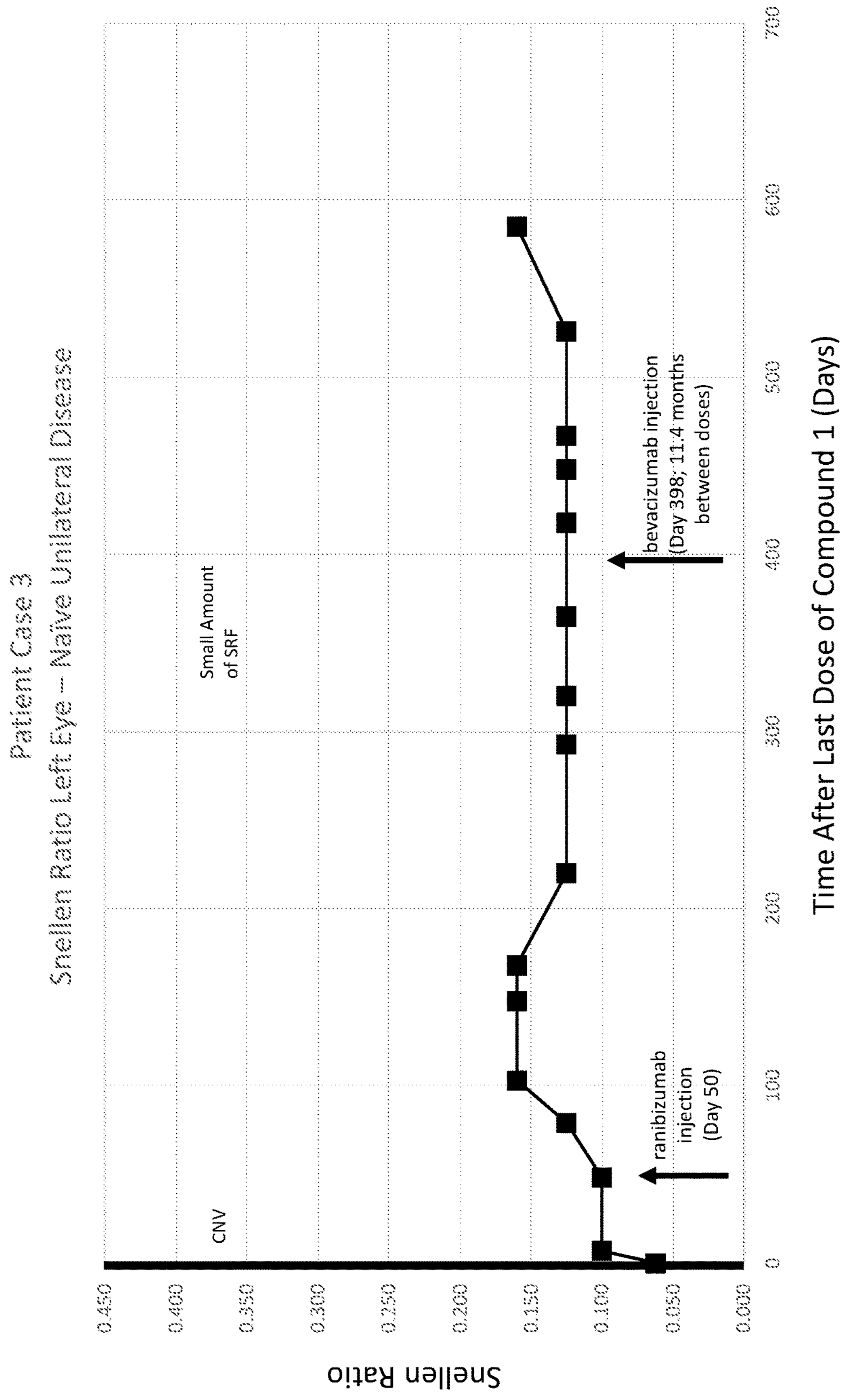
Figure 4:
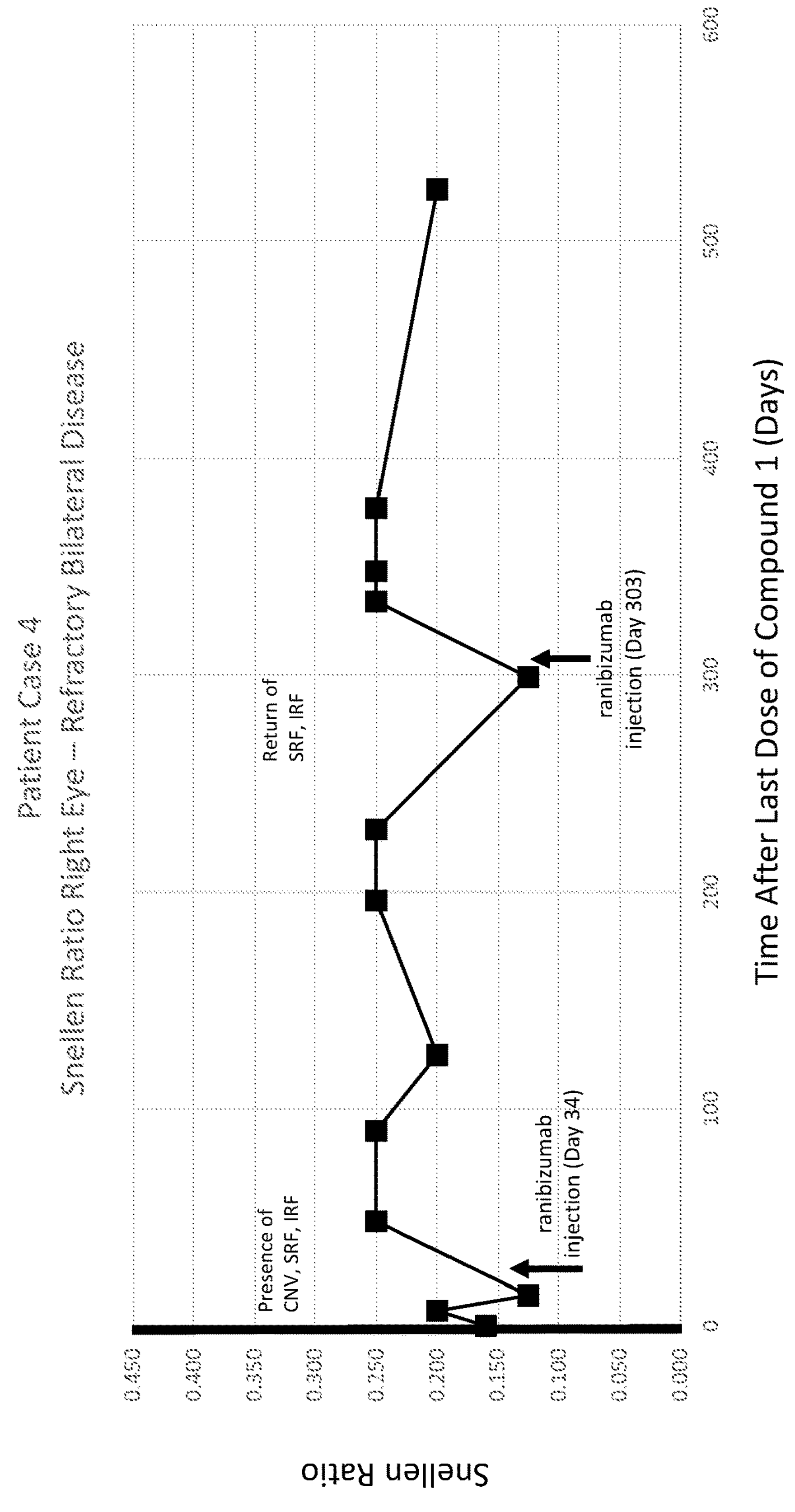
FIG. 4 and FIG. 5 report the Snellen-based visual acuity ratio in each of the eyes of a subject with refractory, bilateral wAMD (i.e., having wAMD in both eyes). The subject is referred to as Patient Case 4. The x-axis depicts time after the last dose of Compound 1 had been administered. Arrows report when an anti-VEGF agent was administered intravitreally (IVT).
Figure 5:
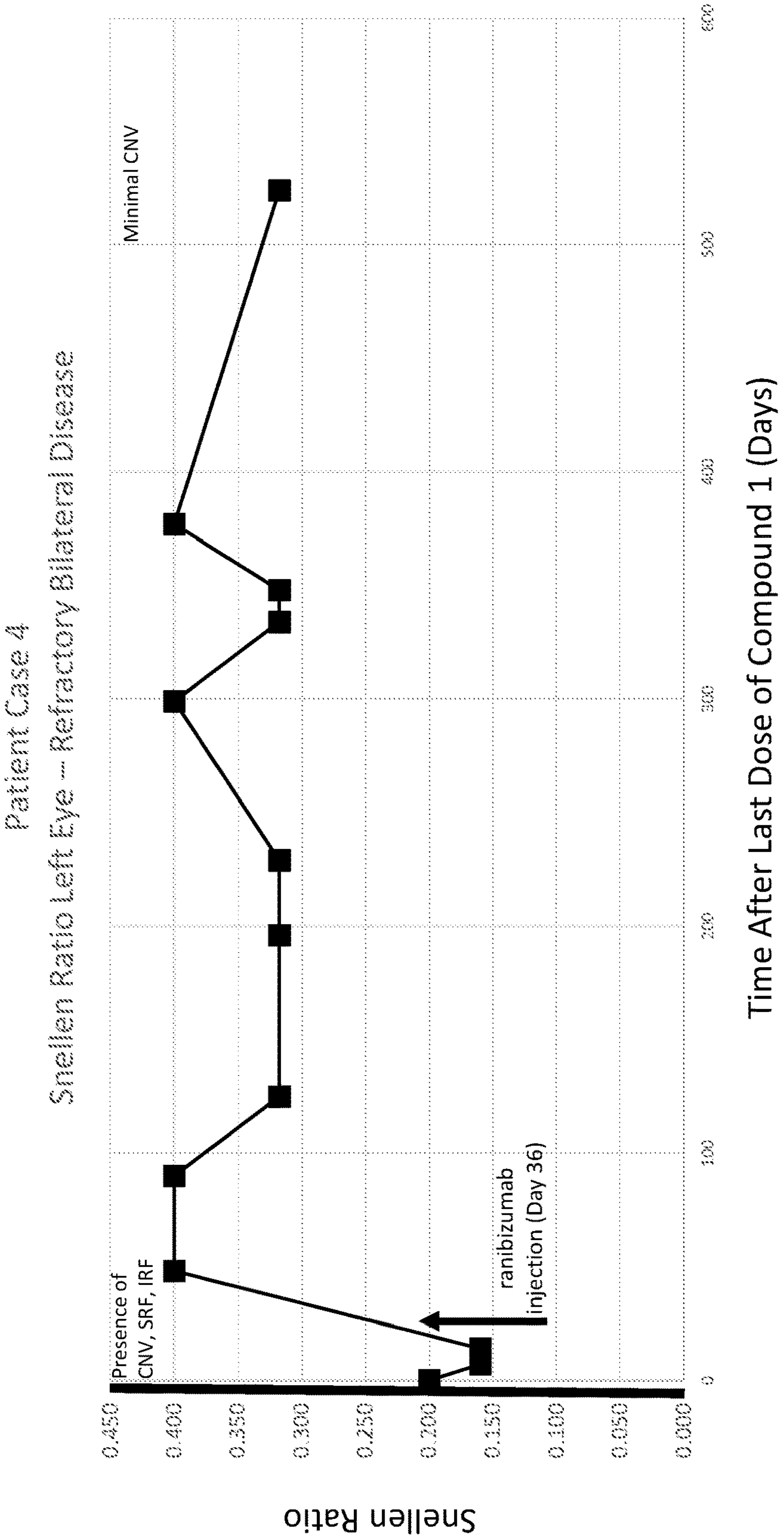
Figure 6:
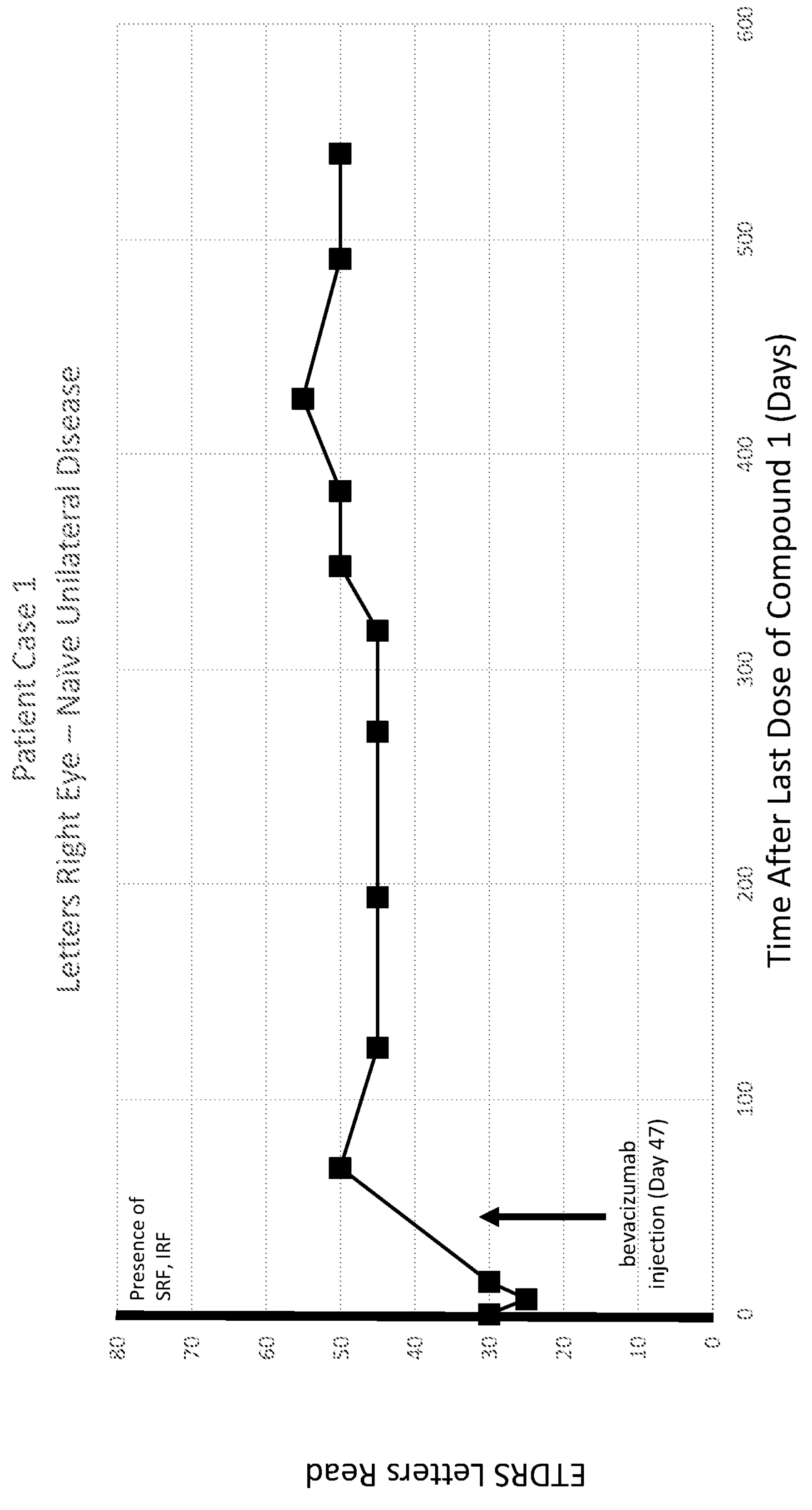
FIG. 6, FIG. 7 and FIG. 8 report the number of ETDRS letters read in the three subjects with naïve unilateral wAMD. The x-axis depicts time after the last dose of Compound 1 had been administered. Arrows report when an anti-VEGF agent was administered intravitreally (IVT). Notes at the top of the graph annotate changes to morphological features of the retina, particularly the fovea, leading to decision to retreat with an anti-VEGF agent. The number of ETDRS letters read was converted from the Snellen-based visual acuity ratios in FIGS. 1 through 3. See Beck R W et al., Am J Ophthalmol. 135. 194-205 (2003).
Figure 7:
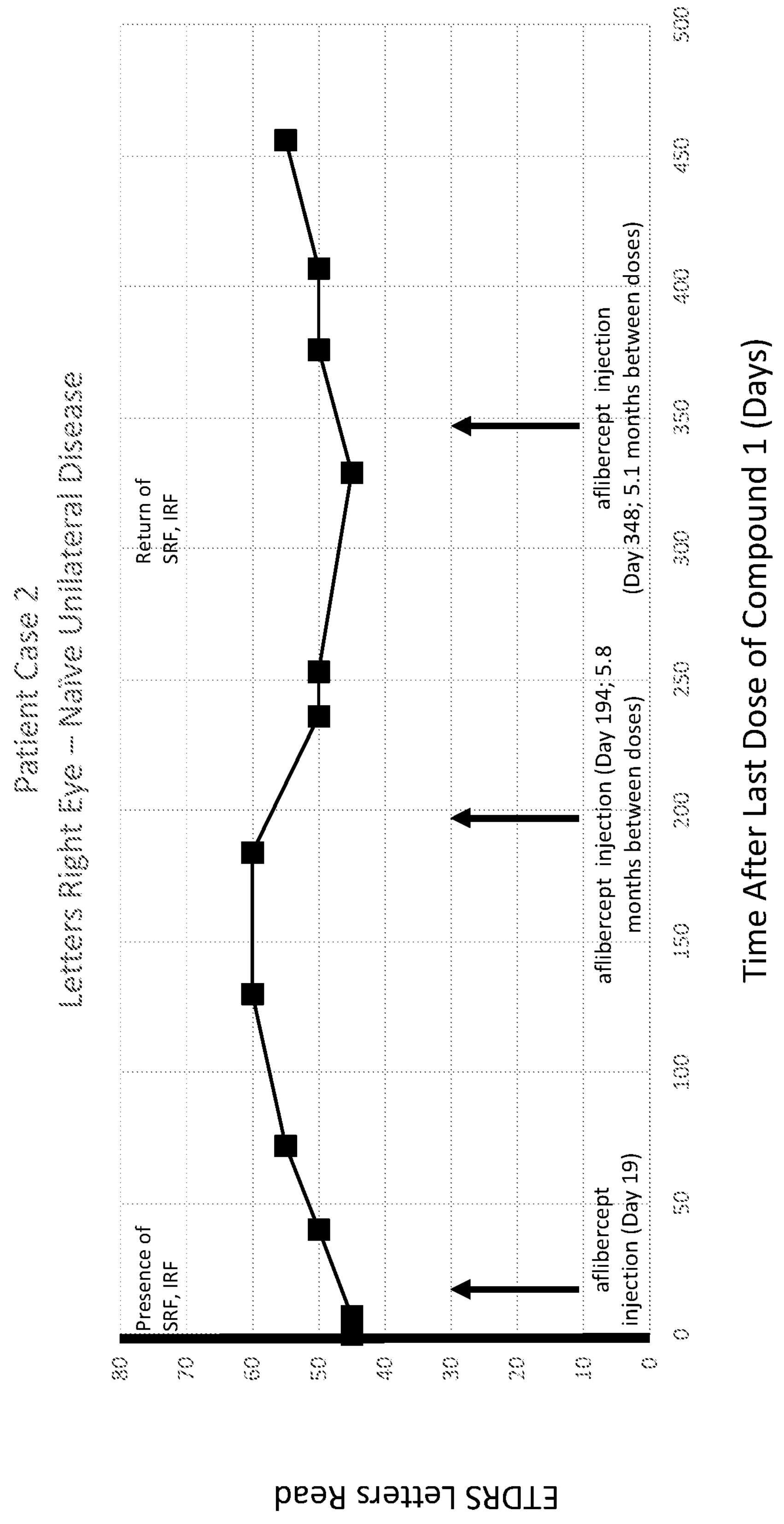
Figure 8:
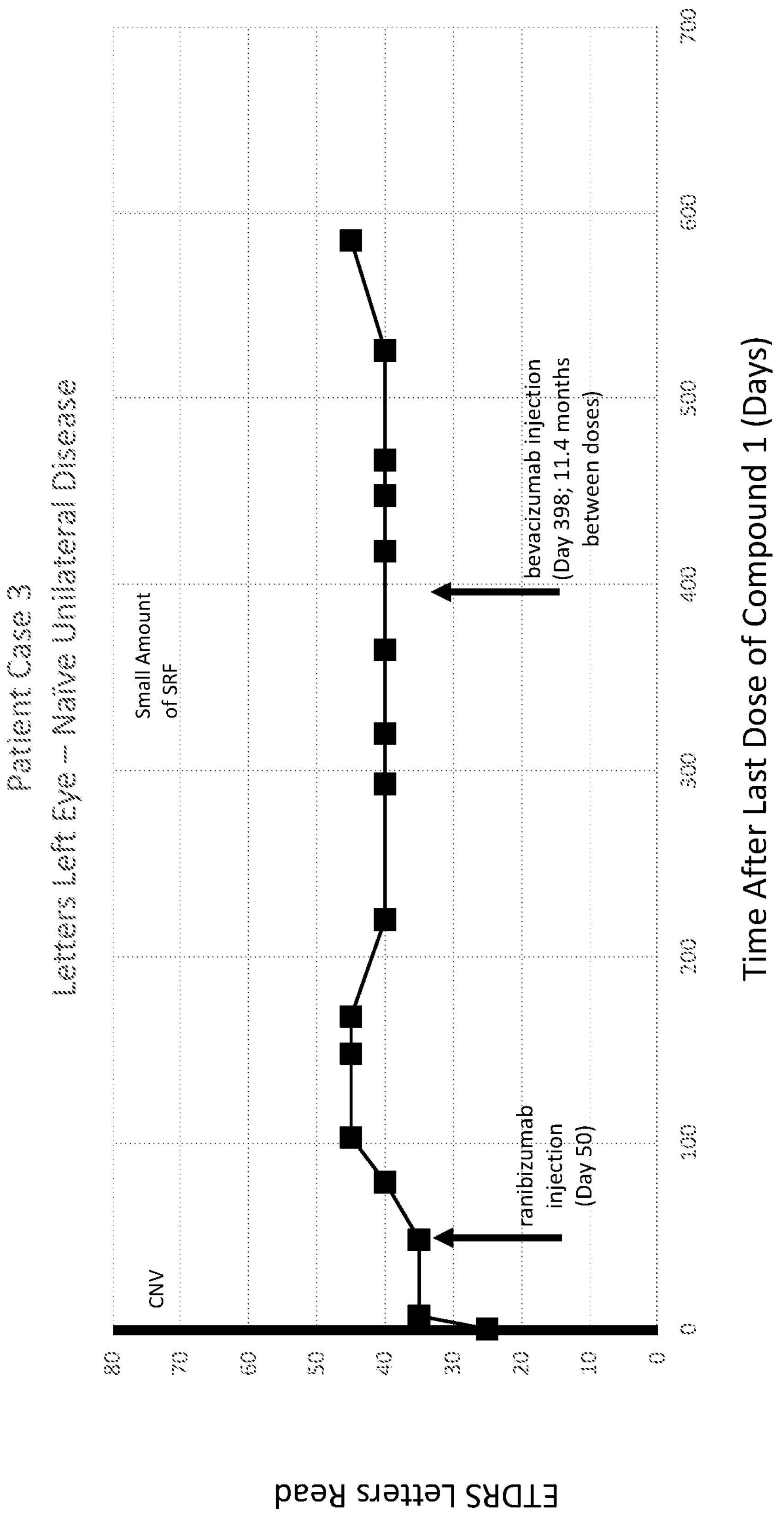

For the subject with refractory, bilateral wAMD (Patient Case 4), 11 anti-VEGF IVT treatments had been received in the left eye and 18 in the right eye prior to treatment with Compound 1. The mean months between doses (after Compound 1 treatment) is reported in the box labeled "Refract Mean."

FIG. 22 is a table reporting the days between doses, months between doses (or since last dose), mean months without anti-VEGF injection with standard deviation, the range of months between doses, doses per month, and doses per year for each treated anti-VEGF IVT eye for Subjects 1-3 (naïve) and Subject 4 (refractory).

All publications and patent applications mentioned in this specification are herein incorporated by reference to the same extent as if each individual publication or patent application was specifically and individually indicated to be incorporated by reference.

DETAILED DESCRIPTION

The methods and compositions disclosed in PCT Patent Publication Number WO2018/187473, U.S. patent application Ser. No. 12/727,318, U.S. patent application Ser. No. 13/596,225, U.S. patent application Ser. No. 14/175,082, U.S. patent application Ser. Ser. No. 13/267,417, U.S. patent application Ser. No. 14/160,646, U.S. patent application Ser. No. 14/572,889, U.S. patent application Ser. No. 13/851,547, U.S. patent application Ser. No. 13/851,564, and U.S. patent application Ser. No. 13/851,538 are hereby incorporated by reference in their entirety as if set forth herein.

Methods of treating symptoms of retina-related disease are provided, the method comprising administering compounds from the compounds and formulae discussed below as well as anti-VEGF agents. An aspect of the disclosure comprises a method of reducing the frequency of administering an anti-VEGF agent to a subject diagnosed with a retina related disorder or disease, such as wet age-related macular degeneration, the method comprising: administering a CCR3 inhibitory agent to the subject; administering the anti-VEGF agent to the subject after the administering of the CCR3 inhibitory agent; and administering additional subsequent doses of the anti-VEGF agent to the subject at a frequency less than the recommended frequency or frequency given in standard practice. In other aspects of the disclosure, the administering additional subsequent doses of the anti-VEGF agent to the subject at a frequency less than the recommended frequency may comprise substituting various different anti-VEGF agents for one or more subsequent doses. For example, the first subsequent dose may be ranibizumab and one or more additional subsequent doses may be bevacizumab, aflibercept, or brolucizumab. Thus mixing anti-VEGF agents is contemplated by the disclosure. In aspects of the disclosure when a first anti-VEGF agent is provided in the initial administration(s) and a second anti-VEGF agent is provided in subsequent administrations, and the first and second anti-VEGF agents differ, the frequency of the doses in the subsequent administrations is less than (i.e., reduced compared to) the recommended frequency of the second anti-VEGF agent or less than the frequency of the second anti-VEGF agent given in standard practice.

Additional aspects of the disclosure include using CCR3 antagonists as the CCR3 inhibitory agent. Further aspects of the disclosure include using Eotaxin-1 antagonists as the CCR3 inhibitory agent. An additional aspect of the disclosure includes using small molecule agents as the CCR3 inhibitory agent or CCR3 antagonist. Yet an additional aspect of the disclosure utilizes Compound 1 as the small molecule agent. A further aspect of the disclosure utilizes CCR3 inhibitory agents that are not delivered through intravitreal or other type of injection into the eye. A further aspect of the disclosure utilizes CCR3 inhibitory agents that are administered orally to the subject diagnosed with the retina related disorder or disease.

Further aspects of the disclosure comprise utilization of antibodies or antibody fragments to vascular endothelial growth factor (VEGF). Additional aspects comprise utilization of said antibodies that selectively bind to or inhibit the activity of VEGF. Examples of such antibodies may include, by way of example and not limitation, bevacizumab, ranibizumab, and brolucizumab. Additional aspects of the disclosure comprise use of recombinant fusion proteins as the anti-VEGF agent. Such fusion proteins may be, by way of example and not limitation, aflibercept.

Another aspect of the disclosure comprises administering additional subsequent doses of the anti-VEGF agent to the subject at a frequency less than the recommended frequency wherein said recommended frequency is greater than or equal to twelve doses every twelve months (i.e., greater than or equal to twelve doses administered within a twelve-month window). Further aspects comprise administering additional subsequent doses of the anti-VEGF agent to the subject at a frequency less than the recommended frequency wherein the recommended frequency is less than one dose every six months. Further aspects comprise administering additional subsequent doses of the anti-VEGF agent to the subject wherein the recommended frequency is less than one dose every five months. Further aspects comprise administering additional subsequent doses of the anti-VEGF agent to the subject wherein the recommended frequency is less than one dose every four months. Further aspects comprise administering additional subsequent doses of the anti-VEGF agent to the subject wherein the recommended frequency is less than one dose every three months. An additional aspect comprises administering additional subsequent doses of the anti-VEGF agent to the subject wherein the recommended frequency is less than one dose every two months.

Further aspects comprise administering additional subsequent doses of the anti-VEGF agent to the subject at a frequency less than the recommended frequency wherein the recommended frequency is greater than or equal to eleven doses every twelve months. Further aspects comprise administering additional subsequent doses of the anti-VEGF agent to the subject at a frequency less than the recommended frequency wherein the recommended frequency is greater than or equal to ten doses every twelve months. Further aspects comprise administering additional subsequent doses of the anti-VEGF agent to the subject at a frequency less than the recommended frequency wherein the recommended frequency is greater than or equal to nine doses every twelve months. Further aspects comprise administering additional subsequent doses of the anti-VEGF agent to the subject at a frequency less than the recommended frequency wherein the recommended frequency is greater than or equal to eight doses every twelve months. An additional aspect comprises administering additional subsequent doses of the anti-VEGF agent to the subject at a frequency less than the recommended frequency wherein the recommended frequency is greater than or equal to seven doses every twelve months.

An additional aspect comprises administering additional subsequent doses of the anti-VEGF agent to the subject at a frequency less than the recommended frequency wherein the recommended frequency is greater than or equal to six doses every twelve months. An additional aspect comprises administering additional subsequent doses of the anti-VEGF agent to the subject at a frequency less than the recommended frequency wherein the recommended frequency is greater than or equal to five doses every twelve months. An additional aspect comprises administering additional subsequent doses of the anti-VEGF agent to the subject at a frequency less than the recommended frequency wherein the recommended frequency is greater than or equal to four doses every twelve months. An additional aspect comprises administering additional subsequent doses of the anti-VEGF agent to the subject at a frequency less than the recommended frequency wherein the recommended frequency is greater than or equal to three doses every twelve months. An additional aspect comprises administering additional subsequent doses of the anti-VEGF agent to the subject at a frequency less than the recommended frequency wherein the recommended frequency is greater than or equal to two doses every twelve months. Another aspect of the disclosure includes equivalents to the aforementioned frequencies, (e.g., a frequency of twelve doses every twelve months can also be understood to include one dose per month and a frequency of six doses per twelve months can also be understood to include one dose every two months, etc.). Another aspect of the disclosure includes irregular dosing frequencies, (e.g., a frequency of twelve doses every twelve months can also be understood to include twelve doses in twelve months that may not follow an absolute regular schedule such as two of the twelve doses administered over one and a half months so long as twelve doses were administered within a twelve-month period overall). Another aspect of the disclosure comprises administering an anti-VEGF agent to a subject intravitreally or otherwise by injection into the eye.

Another aspect of the disclosure further comprises observing or diagnosing a morphological or functional change in an eye of the subject diagnosed with wet age-related macular degeneration (or other retina-associated disease) and who has received one or more additional subsequent doses of the anti-VEGF agent after having been administered a dosing regimen of CCR3/eotaxin-1 pathway antagonist, such as a CCR3 antagonist. Put another way, in any of the methods described herein, the method optionally further comprises examining an eye of the subject to detect a morphological or functional change in the eye. An additional aspect further comprises determining whether to administer additional subsequent doses of the anti-VEGF agent based on the outcome of observing or diagnosing the morphological or functional change in the eye of the subject diagnosed with wet age-related macular degeneration or other retinal disorder or disease. Optionally, any of the methods described herein may further comprise administering one or more doses of anti-VEGF agent following examination of an eye of the subject, or may comprise delaying one or more further administrations of an anti-VEGF agent to the subject. Further aspects of the disclosure comprise the preceding methods wherein the morphological change is selected from increased intraretinal fluid, increased intraretinal fluid, increased choroidal neovascularization, and increased central retinal pigmental epithelium detachment height. Additional aspects of the disclosure comprise the preceding methods wherein the functional change is selected from decreased visual acuity. The types and degree of change in morphological or functional characteristics would be readily determined by physicians or others having ordinary skill in the art. Additional aspects of the disclosure comprise the preceding methods wherein the functional change is selected from a clinically relevant change in central retinal thickness (CRT), central macular thickness (CMT), or CSF thickness, which refers to the retinal thickness in the central 1 mm subfield of the retina. Another aspect comprises a functional change in clinically relevant CRT, CMT, or CSF as determined from optical coherence tomography (OCT).

An additional aspect of the disclosure comprises a method of reducing the frequency of administering an anti-VEGF agent to a subject diagnosed with a retina related disorder or disease, the method comprising concurrently administering the anti-VEGF agent with a CCR3 inhibitory agent wherein the anti-VEGF agent is administered at a frequency less than the recommended frequency or frequency given in standard practice. Another aspect comprises the aforementioned concurrent administration of the anti-VEGF agent with a CCR3 inhibitory agent wherein the frequency of administration of the anti-VEGF agent is adjusted based on a morphological or functional change in the eye of the subject. An additional aspect comprises administering a loading dose of the anti-VEGF agent and either concurrently administering a CCR3 inhibitory agent from the start of the loading dose period onward or beginning the concurrent CCR3 inhibitor administration after the anti-VEGF loading dose period is completed.

Yet an additional aspect of the disclosure comprises first administering a CCR3 inhibitory agent to a treatment-naïve subject with respect to treatment of the retina related disorder and subsequently administering the anti-VEGF agent.

In any of the methods described herein, the CCR3 inhibitory agent may be administered within about 360 days of administration of the anti-VEGF agent (e.g., within about 330 days, within about 300 days, within about 270 days, within about 240 days, within about 210 days, within about 180 days, within about 150 days, within about 120 days, within about 90 days, within about 75 days, within about 60 days, within about 45 days, within about 30 days, within about 14 days, within about 7 days, within about 3 days, or within about 1 day of administering the anti-VEGF agent). For example, the CCR3 inhibitory agent may be administered between about 1-180 days prior to the initial anti-VEGF agent administration (i.e., within six months, within three months, within two months, within one month, within three weeks, within two weeks, or within one week of the initial administration of the anti-VEGF agent to the subject in the context of the method of the disclosure). In various aspects of the method described herein, the CCR3 inhibitory agent may be administered until a morphological or functional change in the eye of the subject warrants administration of an anti-VEGF agent. Administration of the CCR3 inhibitory agent may be continued after commencing the anti-VEGF agent, but this is not required. Alternatively, the method comprises ceasing the administration of the CCR3 inhibitory agent.

The disclosure further provides a method of treating a subject suffering from a retina-associated disease, the method comprising administering an anti-VEGF agent to a subject suffering from a retina-associated disease and previously treated with a CCR3 inhibitory agent, wherein the anti-VEGF agent is administered at a frequency less than the recommended frequency for the anti-VEGF agent. Optionally, the subject was treated with the CCR3 inhibitory agent within six months of administration of the anti-VEGF agent.

Additional aspects of the disclosure comprise the preceding methods wherein the subject has been diagnosed with, by way of example and not limitation, dry macular degeneration (dry AMD), retinal vein occlusion either branched (BRVO) or central (CRVO), retinopathy of prematurity, diabetic retinopathy (with or without macular edema), diabetic macular edema (DME) and geographic atrophy.

A. CCR3 ANTAGONISTS i. Compound 1 & its Analogs

The methods of the disclosure further comprise administration to a subject of Compound 1. Compound 1 is a small molecule antagonist of CCR3 which specifically and selectively binds to CCR3.

Compound 1

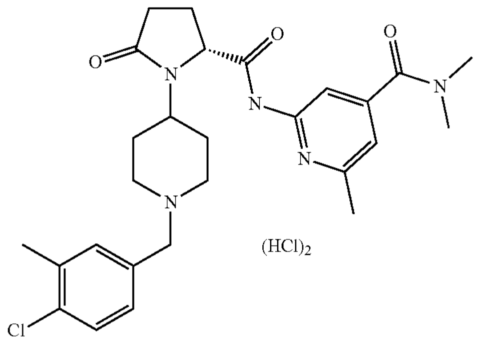

$(HCl)_2$

Structural and chemical analogs to Compound 1 also are contemplated for use in the methods the disclosure. Examples of such analogs and their structural and chemical formulae may be found in PCT patent publication number WO2018/187473, U.S. patent application Ser. No. 12/727,318, U.S. patent application Ser. No. 13/596,225, U.S. patent application Ser. No. 14/175,082, U.S. patent application Ser. No. 13/267,417, U.S. patent application Ser. No. 14/160,646, U.S. patent application Ser. No. 14/572,889, U.S. patent application Ser. No. 13/851,547, U.S. patent application Ser. No. 13/851,564, and U.S. patent application Ser. No. 13/851,538 which are incorporated by reference in their entirety as if set forth herein.

In any of the methods described herein, the CCR3 inhibitory agent may comprise a compound of Formula 1:

Formula 1

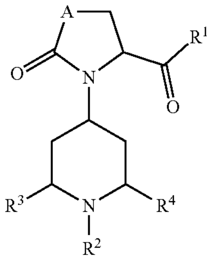

wherein

A is $CH_2$, O or N—$C_{1-6}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$-alkyl, $NHSO_2$-phenyl, NHCONH-phenyl, halogen, CN, $SO_2$—$C_{1-6}$-alkyl, COO—$C_{1-6}$-alkyl;

a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, methoxy-phenyl;

a group selected from $NHCH(pyridinyl)CH_2COO$—$C_{1-6}$-alkyl, $NHCH(CH_2O$—$C_{1-6}$-alkyl)-benzoimidazolyl, optionally substituted with halogen or CN;

or 1-aminocyclopentyl, optionally substituted with methyl-oxadiazole;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}\text{-alkyl})_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}\text{-alkyl})(CH_2CON(C_{1-4}\text{-alkyl})_2)$ O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}\text{-alkyl})_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl and =O;

$R^{1.1}$ is H, $C_{1-6}$-alkyl, $C_{3-6}$-cycloalkyl, $C_{1-6}$-haloalkyl, $CH_2CON(C_{1-6}\text{-alkyl})_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ is H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-6}\text{-alkyl})_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

a aromatic or non-aromatic $C_{9\ or\ 10}$-bicyclic-ring, whereas one or two carbon atoms are replaced by N, O or S each optionally substituted with one or two residues selected from the group consisting of $N(C_{1-6}\text{-alkyl})_2$, CONH—$C_{1-6}$-alkyl, =O;

a heterocyclic non-aromatic ring, optionally substituted with pyridinyl;

4,5-dihydro-naphtho[2,1-d]thiazole, optionally substituted with NHCO—$C_{1-6}$-alkyl, $R^{1.2.1}$ is H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$ alkylene O—$C_{1-4}$ alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ is H, $C_{1-6}$-alkyl;

$R^{1.2.3}$ is a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, heteroaryl;

$R^2$ is selected from the group consisting of $C_{1-6}$-alkylene-phenyl, $C_{1-6}$-alkylene-naphthyl, and $C_{1-6}$-alkylene-heteroaryl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-6}$-alkyl;

$R^4$ is H, $C_{1-6}$-alkyl;

or $R^3$ and $R^4$ together are forming a $CH_2$—$CH_2$ group.

The antagonistic potency of Compound 1 was determined in several human CCR3-dependent assays (see WO2018/187473). Compound 1's potency was determined via a receptor binding assay, with the IC50 measured at 4.0±1.8 nM and the Ki at 3.2±0.6 nM. IC50 for a calcium influx assay using human CCR3-transfected CHEM1-Gα15 cells was determined to be 0.9±0.2 nM. Antagonism by Compound 1 of human eotaxin-1 induced eosinophil shape change in human whole blood was achieved with an IC50 of 42.5±43.5 nM.

Potencies for several other mammalian species were also determined in different assays. Species included cynomolgus (macaque) monkeys, mouse, rat, and canines. With respect to receptor binding assays, the Ki for Compound 1 on mouse CCR3 was 124.3±0.9 nM, and the IC50 87.3±5.6 nM. For rat CCR3, the Ki for the investigational drug of the invention was 1488.6±127.6 nM and the IC50 1719.0±129.9 nM.

ii. Additional CCR3 Antagonists

1. Small Molecules

An aspect of the disclosure is CCR3 small molecule antagonists which are both potent and selective antagonists of human CCR3. An additional aspect of the disclosure is CCR3 small molecule antagonists which exhibit an inhibitory concentration 50 (IC50) of 500 nM or less in one or more of various assays. Yet another aspect of the disclosure is CCR3 small molecule antagonists which exhibit an inhibitory concentration 50 (IC50) of 200 nM or less in one or more of various assays. A further aspect of the disclosure is CCR3 small molecule antagonists which exhibit an inhibitory concentration 50 ($IC_{50}$) of 100 nM or less in one or more of various assays. Another aspect of the disclosure is CCR3 small molecule antagonists which exhibit an inhibitory concentration 50 ($IC_{50}$) of 50 nM or less in one or more various assays. Yet another aspect of the disclosure is CCR3 small molecule antagonists which exhibit an inhibitor concentration 50 (IC50) of 10 nM or less in one or more various assays. An "$IC_{50}$" is the concentration of an inhibitor where the response induced by the agonist ligand is reduced by half. An aspect of the disclosure is that the response can be the activity of the CCR3 receptor protein which binds CCR3 antagonists (including small molecule and antibody antagonists), calcium influx in CCR3-transfected cells, eosinophil shape change, CCR3 internalization, or chemotaxis (migration) assays.

Various assays to determine an IC50 value for a CCR3 small molecule antagonist are well-known to those having ordinary skill in the art.

Eosinophil Shape Change Assay (ESC)

Eosinophils undergo dramatic shape changes in response to immunological and chemotactic factors, which can be measured in an eosinophil shape change (ESC) assay. It can be determined, for example, using whole blood samples which are incubated with 30 nmol/L of eoxtaxin-1 at 37° C. for 7 minutes. Samples are then fixed on ice for 20 minutes followed by erythrocyte lysis at room temperature for 15 minutes. ESC is determined by flow cytometry using forward scatter (FSC) as a measure of cell size and side scatter (SSC) as a measure of granularity. The percentage inhibition of ESC is then calculated and plotted in order to determine the $IC_{50}$.

CCR3 Internalization

CCR3 ligand-induced internalization is a critical step in eosinophil functional response to stimulatory signals. Inhibition of CCR3 internalization by CCR3 antagonists can be determined using blood samples incubated with 30 nmol/L of eotaxin-1 at 37° C. for 30 minutes. The samples are then incubated with allophycocyanin (APC)-conjugated antibody against CCR3 at room temperature in the dark for 30 minutes, followed by erythrocyte lysis and cell fixation. Samples are then washed and analyzed for FSC, SSC, and APC-fluorescence by flow cytometry. The percentage inhibition of CCR3 internalization is then calculated and plotted.

Calcium Influx (Calcium Mobilization) Assay

CCR3 $Ca^{2+}$ mobilization studies can be carried out as described previously (White R J, et al., J Biol Chem, 275(47):36626-31 (2000)). The assay can be performed using Fluo 3-loaded RBL-2H3-CCR3 cells and a microtiter plate-based assay using a fluorescent imaging plate reader (FLIPR). RBL-2H3-CCR3 cells are grown to confluence in RPMI 1640 medium containing 10% fetal calf serum in T-150 flasks with 5% $CO_2$ at 37° C. Cells are removed from the T-150 flask by removing the medium and then treating the cells with 5 mL of Versene for 5 min at room temperature. Cells are then washed once in RPMI 1640 medium, 10% fetal calf serum and subsequently plated into sterile 96-well black at 40,000 cells/well and incubated for 18-24 hours. On the day of assay, the medium is removed and replaced with 100 μl of Earle's minimal essential medium with Earle's salts containing L-glutamine, 0.1% bovine serum albumin, 4 μM Fluo-3 acetoxymethyl ester (Fluo-3/AM; Molecular Probes, Inc., Eugene, OR), and 1.5 mM sulfinpyrazone. Plates are then incubated for 60 min at 37° C., medium is removed and replaced with the same medium without Fluo-3/AM, and plates are incubated for 10 min at 37° C. Cells are washed three times and incubated at 37° C. in 100 μL of assay buffer (120 mm NaCl, 4.6 mm KCl, 1.03 mM $KH_2PO4$, 25 mM NaHCO3, 1.0 mm $CaCl_2$, 11 mM glucose, 20 mM HEPES (pH 7.4) with 1.5 mM sulfinpyrazone. Plates are then placed into FLIPR for analysis. The maximal change in fluorescence after addition of agonist (eotaxin-1) is quantitated. The percentage of maximal agonist-induced $Ca^{2+}$ mobilization is determined for each concentration of antagonist, and the $IC_{50}$ is defined as the concentration of antagonist that inhibits 50% of the maximal response induced by 33 nM eotaxin-1.

Chemotaxis (Migration) Assay

Chemotactic responsiveness of eosinophils (which express CCR3) can be determined using ChemoTx™ plates (see Wise E L, J Biol Chem, 282(38):27935-43 (2007)). An assay buffer of RPMI supplemented with 0.1% BSA are loaded with duplicate concentrations of agonist in the presence or absence of a CCR3 antagonist. These solutions are applied in a final volume of 31 μL to the lower wells of the chemotaxis chamber. A filter is put into place and $2\times10^5$ eosinophils in the same assay buffer are applied to the upper surface. Following a 5-hour incubation at (humid) 37° C. in the presence of 5% $CO_2$, the number of migrating eosinophils traversing a 5 μm pore filter are counted, providing the number of migrated cells. The greater the inhibition by an antagonist, the less migration is observed.

Another aspect of the disclosure is CCR3 small molecule antagonists which have a Ki value of 200 nM or less in a receptor displacement binding assay (also referred to as a receptor binding assay). The Ki value is the dissociation constant which describes the binding affinity between the inhibitor and the receptor. An additional aspect of the disclosure is CCR3 small molecule antagonists which have a Ki value of 100 nM or less in a receptor displacement binding assay. Yet an additional aspect of the disclosure is CCR3 small molecule antagonists which have a Ki value of 50 nM or less in a receptor displacement binding assay. Yet another aspect of the disclosure is CCR3 small molecule antagonists which have a Ki value of 10 nM or less in a receptor displacement binding assay. IC50 values for receptor displacement can also be determined for CCR3 receptor binding and are a measure of the concentration of antagonist needed to inhibit 50% of the agonist ligand (eotaxin-1) from binding CCR3 receptors.

Receptor Displacement Binding Assay

Dissociation constant (Ki) values for CCR3 small molecule antagonists can be determined using techniques known to those having ordinary skill in the art. Similarly, $IC_{50}$ values for CCR3 antagonists can be determined with such techniques. An example of a receptor displacement binding assay to determine dissociation constants for receptors such as CCR3 similarly uses radioligand displacement (see Warrior U, et al., J Biomol Screening, 8(3):324-31 (2003) and Becker O M et al., PNAS, 101(31):11304-309 (2004)). Unlabeled (cold) antagonist compounds are initially tested at a 10-μM concentration in duplicate with K562 cell membranes (containing CCR3 receptors) and radioligand. Hits showing >50% inhibition at 10 μM are validated by a full-concentration dose-response curve, measured between 10-10 M (0.1 nM) and 10-4 M (0.1 mM). The radioligand is [1251] eotaxin (0.1 nM, Kd=0.7 nM).

Thus, the disclosure contemplates use of other small molecule CCR3 antagonists (other than Compound 1 of the disclosure and its analogs) in the context of the method described herein. Many other small molecule CCR3 antagonists are known to those having ordinary skill in the art. These include CCR3 antagonists disclosed by Pease J E and Horuk R, *Expert Opin Drug Discov,* 9(5):467-83 (2014) and *Expert Opin Ther Patents* 19(1) (2009), such as (by way of example, and not limitation) ASM8, GSK766994, GW824575, DPC168, BMS-639623, QAP-642, AZD3778, SB-328437, YM-344031, Compound 80, Compound 27, Compound 32, YM 344484, Compound 3a (Astra Zeneca), Compound 3b (Astra Zeneca), AZ10565259, AZ12436092, 2-(4-fluorophenyl)-4-(2-(1-isonicotinoylpiperidin-4-yl)-4-(4-nitrophenyl)butyl)-1,5-dimethyl-1,2-dihydro-3H-pyrazol-3-one (Astra Zeneca), Compound 20 (Astra Zeneca), and Compound 60 (Astra Zeneca). Aspects of the disclosure may employ these molecules as small molecule CCR3 antagonists serving as CCR3 inhibitory agents.

Further aspects of the disclosure include administration of small molecules disclosed in U.S. Pat. Nos. 7,705,153, 9,206,186, 8,030,303, 7,935,700, and International Patent Application Serial Number PCT/EP2004/002496, as small molecule CCR3 antagonists.

The disclosure contemplates aspects wherein the CCR3 inhibitory agent comprises a CCR3 antagonist compound from the following table:

| Compound Structure | Reference |
|---|---|
| 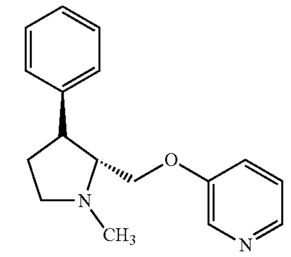 | Pease & Horuk, *Expert Opin. Ther. Patents* 19(1) (2009). $IC_{50}$ = 195 nM |
| 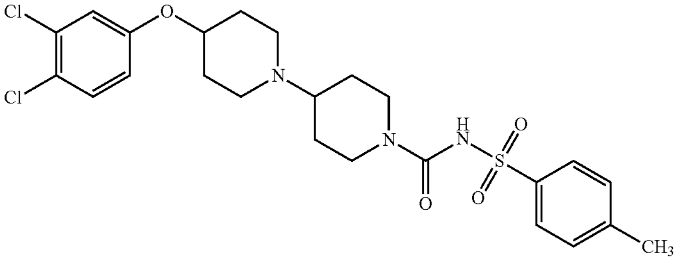 [SMILES: Cc1ccc(S(=O)(=O)NC(=O)N2CCC(N3CCC(Oc4ccc(Cl)c(Cl)c4)CC3)CC2)cc1] | U.S. Pat. No. 7,307,090 $IC_{50}$ = 8 nM |
| 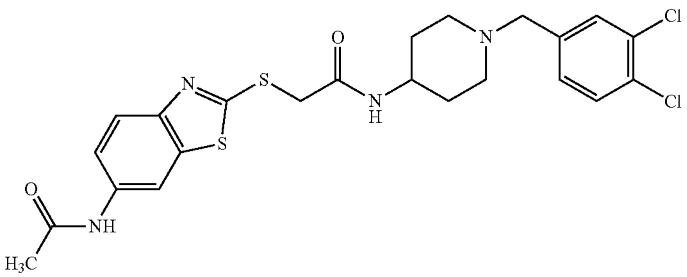 [SMILES: CC(=O)Nc1ccc2nc(SCC(=O)NC3CCN(Cc4ccc(Cl)c(Cl)c4)CC3)sc2c1] | Pease & Horuk, *Expert Opin. Ther. Patents* 19(1) (2009). $IC_{50}$ = 1.5 nM |
| 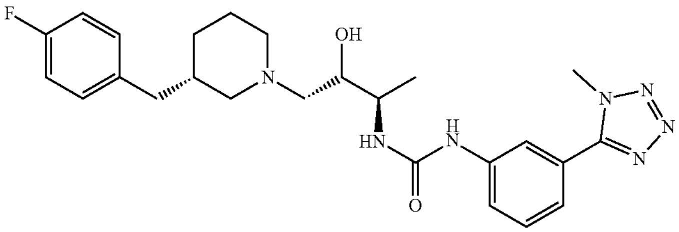 | Pease JE and Horuk R, *Expert Opin Drug Discov*, 9(5):467-83 (2014) $IC_{50}$ (binding) = 300 pM (0.3 nM) $IC_{50}$ (chemotaxis) = 38 pM |
| 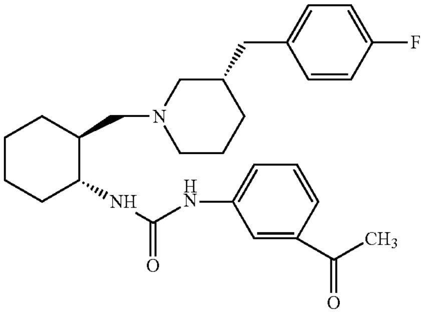 [SMILES: CC(=O)c1cccc(NC(=O)N[C@@H]2CCCC[C@H]2CN2CCC[C@@H](Cc3ccc(F)cc3)C2)c1] | Pease & Horuk, *Expert Opin. Ther. Patents* 19(1) (2009). $IC_{50}$ = 2 nM |
| 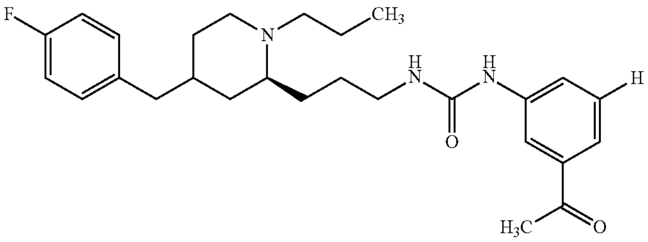 [SMILES: CCCN1CCC(Cc2ccc(F)cc2)C[C@@H]1CCCNC(=O)Nc1cccc(C(C)=O)c1] | Watson PS et al., Bioorg & Med Chem, 282(38):27935-43 (2007). $IC_{50}$ (binding) = 2 nM $IC_{50}$ (Calcium Influx) = 26 nM $IC_{50}$ (Chemotaxis) = 19 nM |

-continued
| Compound Structure | Reference |
| --- | --- |
| 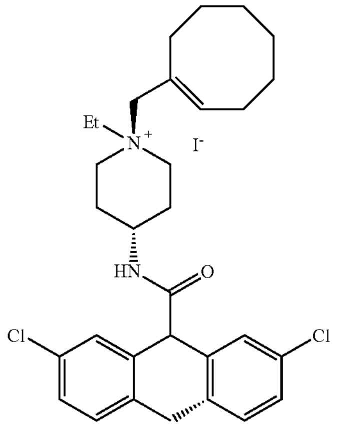 | Wise EL et al., *J Biol Chem*, 282(38): 27935-43 (2007) and Sabroe I, et al., J Biol Chem, 275(34): 25985-92 (2000). |
| 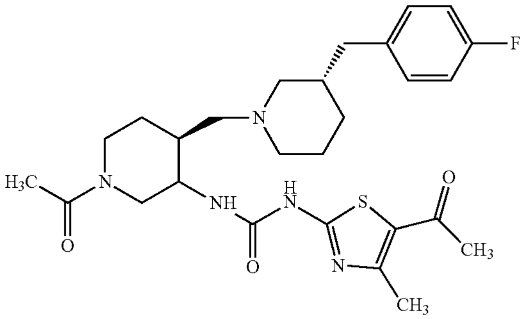 [SMILES: CC(=O)c1sc(NC(=O)NC2CN(C(C)=O)CC[C@H]2CN2CCC[C@@H](Cc3ccc(F)cc3)C2)nc1C] | Pease & Horuk, *Expert Opin Ther Patents* 19(1) (2009). $IC_{50}$ = 1.9 nM |
| 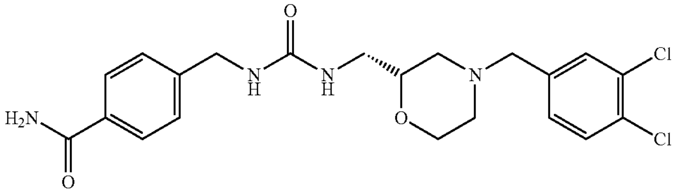 | Pease & Horuk, *Expert Opin Ther Patents* 19(1) (2009). $IC_{50}$ = 10 nM |
| 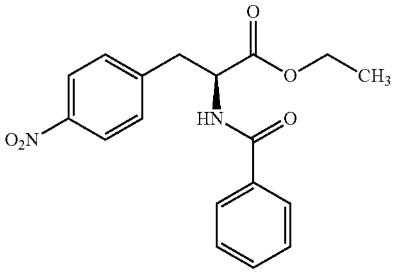 [SMILES: CCOC(=O)[C@H](Cc1ccc([N+](=O)[O-])cc1)NC(=O)c1ccccc1] | Mori A. et al., *Int Immunol*, 19(8):913-21 (2007). |
| 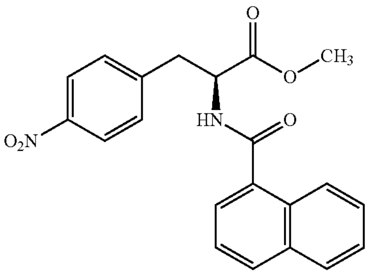 [SMILES: COC(=O)[C@H](Cc1ccc([N+](=O)[O-])cc1)NC(=O)c1cccc2ccccc12] | Pease & Horuk, *Expert Opin Ther Patents* 19(1) (2009). |

-continued
| Compound Structure | Reference |
| --- | --- |
| 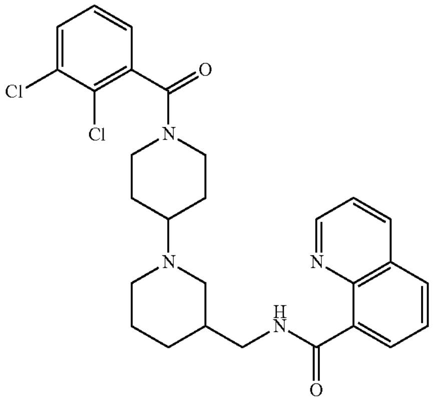 [SMILES: O=C(NCC1CCCN(C2CCN(C(=O)c3cccc(Cl)c3Cl)CC2)C1)c1cccc2cccnc12] | Pease & Horuk, *Expert Opin Ther Patents* 19(1) (2009). |
| 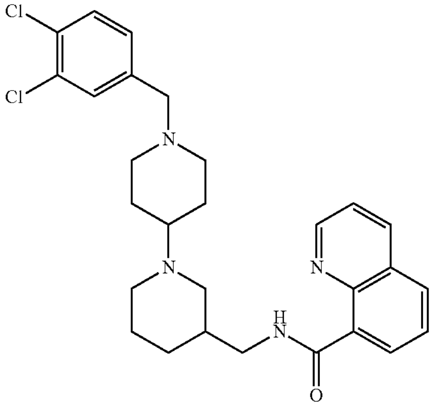 [SMILES: O=C(NCC1CCCN(C2CCN(Cc3ccc(Cl)c(Cl)c3)CC2)C1)c1cccc2cccnc12] | Pease & Horuk, *Expert Opin Ther Patents* 19(1) (2009). $IC_{50}$ = 30 nM |
| 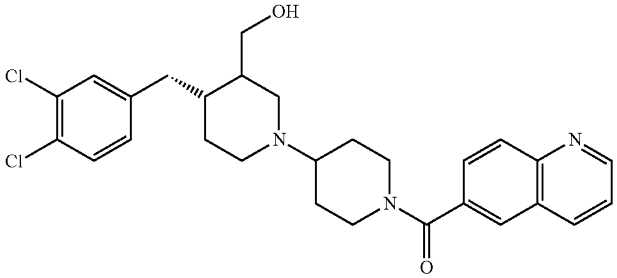 | Pease & Horuk, *Expert Opin Ther Patents* 19(1) (2009). |
| 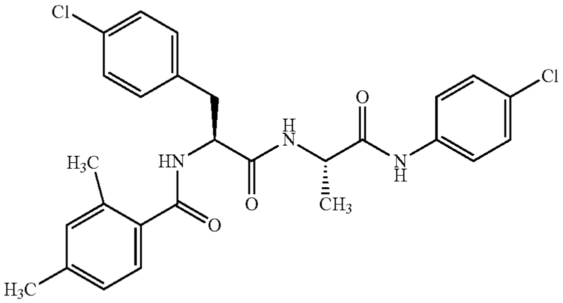 [SMILES: Cc1ccc(C(=O)N[C@@H](Cc2ccc(Cl)cc2)C(=O)N[C@@H](C)C(=O)Nc2ccc(Cl)cc2)c(C)c1] | Pease & Horuk, *Expert Opin Ther Patents* 19(1) (2009). $IC_{50}$ = 3.5 nM |

-continued
| Compound Structure | Reference |
| --- | --- |
| 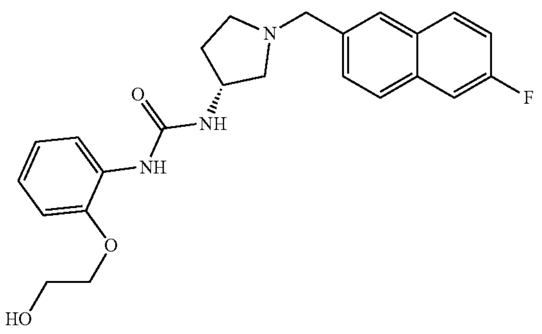 [SMILES: O=C(Nc1ccccc1OCCO)N[C@@H]1CCN(Cc2ccc3cc(F)ccc3c2)C1] | Nitta A, et al., *Bioorg & Med Chem Lett*, 22 6872-81 (2012). $IC_{50}$ = 1.7 nM |
| 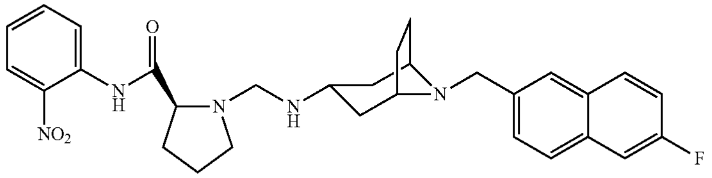 [SMILES: O=C(Nc1ccccc1[N+](=O)[O-])[C@@H]1CCCN1CNC1CC2CCC(C1)N2Cc1ccc2cc(F)ccc2c1] | Nitta A, et al., *Bioorg & Med Chem Lett*, 22 6872-81 (2012). $IC_{50}$ = 4.9 nM |
| 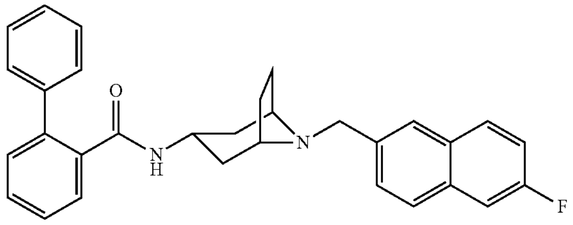 [SMILES: O=C(NC1CC2CCC(C1)N2Cc1ccc2cc(F)ccc2c1)c1ccccc1-c1ccccc1] | Sato I, et al., *Bioorg & Med Chem Lett*, 16 144-56 (2008). $IC_{50}$ = 20 nM |
| 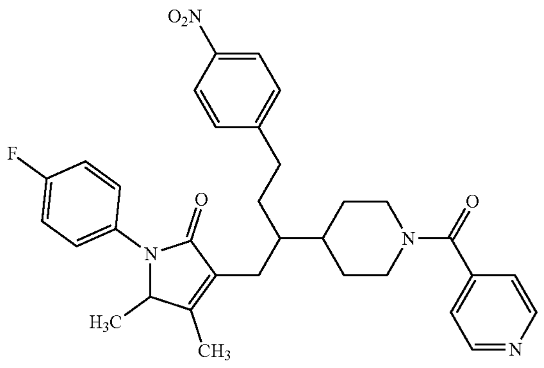 [SMILES: CC1=C(CC(CCc2ccc([N+](=O)[O-])cc2)C2CCN(C(=O)c3ccncc3)CC2)C(=O)N(c2ccc(F)cc2)C1C] | Pease & Horuk, *Expert Opin Ther Patents* 19(1) (2009). $IC_{50}$ = 12 nM |

-continued

| Compound Structure | Reference |
|---|---|
| 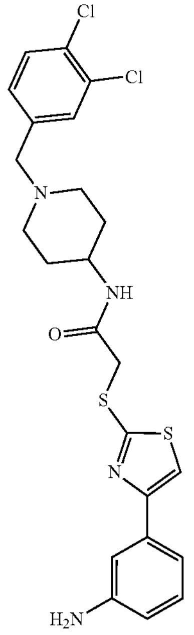 [SMILES: Nc1cccc(-c2csc(SCC(=O)NC3CCN(Cc4ccc(Cl)c(Cl)c4)CC3)n2)c1] | U.S. Pat. No. 7,115,635 |
| 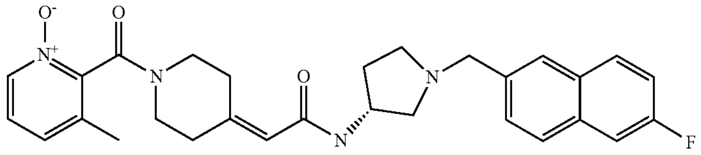 [SMILES: Cc1ccc[n+]([O-])c1C(=O)N1CCC(=CC(=O)N[C@@H]2CCN(Cc3ccc4cc(F)ccc4c3)C2)CC1] | Suzuki K, et al., *BBRC*, 339:1217-23 (2006). $IC_{50}$ (binding) = 3 nM $IC_{50}$ (Calcium influx) = 5.4 nM $IC_{50}$ (chemotaxis) = 19.9 nM |
| 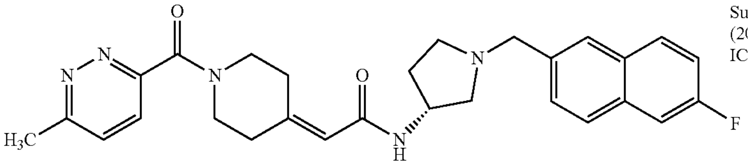 | Suzuki K, et al., *Eur J Pharm*, 563 224-32 (2007). $IC_{50}$ (Calcium influx) = 6.2 nM |
| 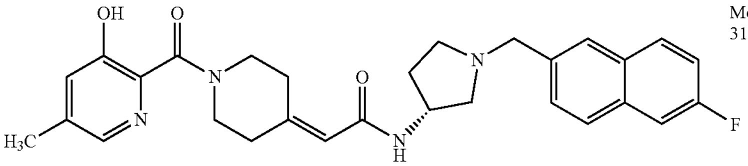 | Morokata T et al., *J Pharm Exp Ther* 317(1):244-50 (2006). |

The disclosure further contemplates methods wherein the CCR3 inhibitory agent is comprised of one of the following small molecule CCR3 antagonists (further described in U.S. Pat. No. 10,130,634 (morpholine compounds) and U.S. Pat. No. 7,935,700 (morpholine compounds) which have IC50 values below 50 nM with many below 10 nM, incorporated herein by reference in their entireties and particular with respect to their description of the following compounds):

(2S)-[4-(carboxymethyl)thiazol-2-ylthio]-N-{[4-(3,4-dichlorobenzyl)morpholin-2-yl]methyl}acetamide (2S)-[4-(carboxymethyl)thiazol-2-ylthio]-N-{[4-(3,4-dichlorobenzyl)morpholin-2-yl]methyl}acetamidehydrobromide (2S)-[4-(3-aminophenyl)thiazol-2-ylthio]-N-{[4-(3,4-dichlorobenzyl)morpholin-2-yl]methyl}acetamide, (2S)-[4-(3-carbamoyl-4-hydroxyphenyl)thiazol-2-ylthio]N-{[4-(3,4-dichlorobenzyl)morpholin-2-yl]methyl}acetamide, (2S)—N-{[4-(3,4-dichlorobenzyl)morpholin-2-yl]methyl}[4-(pyridin-4-yl)thiazol-2-ylthio]acetamide, (2S)—N-{[4-(3,4-dichlorobenzyl)morpholin-2-yl]methyl}[4-(3,4-dimethoxyphenyl)thiazol-2-ylthio]acetamide, (2S)-(4-carbamoylthiazol-2-ylthio)-N-{[4-(3,4-dichlorobenzyl)morpholin-2-yl]methyl}acetamide, (2S)-{4-[(2-amino-2-oxoethyl)aminocarbonyl]thiazol-2-ylthio}-N-{[4-(3,4-dichlorobenzyl)morpholin-2-yl]methyl}acetamide, (2S)—N-{[4-(3,4-dichlorobenzyl)morpholin-2-yl]methyl}[4-(5-methyl-1,2,4-oxadiazol-3-yl)thiazol-2-ylthio]acetamidehydrochloride, (2S)-(5-amino-8H-indeno[1,2-d]thiazol-2-ylthio)-N-{[4-(3,4-dichlorobenzyl)morpholin-2-yl]methyl}acetamide, (2S)-(4-carboxyphenylthio)-N-{[4-(3,4-dichlorobenzyl) morpholin-2-yl]methyl}acetamide,
(2S)-{4-[(2-amino-2-oxoethyl)aminocarbonyl] phenylthio}N-{[4-(3,4-dichlorobenzyl)morpholin-2-yl] methyl}acetamide,
(2S)-{4-[(2-carboxyethyl)aminocarbonyl]thiazol-2-ylthio}N-{[4-(3,4-dichlorobenzyl)morpholin-2-yl] methyl}acetamide hydrochloride,
(2S)-(5-acetamino-1,3,4-thiadiazol-2-ylthio)-N-{[4-(3,4-dichlorobenzyl)morpholin-2-yl]methyl}acetamide,
(2S)-4-(4-carbamoylthiazol-2-ylthio)-N-{[4-(3,4-dichlorobenzyl)morpholin-2-yl]methyl}butylamide hydrochloride,
(2S)—N-{[4-(3,4-dichlorobenzyl)morpholin-2-yl]methyl} [4-(1H-tetrazol-5-yl)thiazol-2-ylthio]acetamide,
(2S)—N-{[4-(3,4-dichlorobenzyl)morpholin-2-yl]methyl} ([1,3]thiazolo[5,4-b]pyridin-2-ylthio) acetamide,
(2S)-(E)-[4-(2-carbamoylethen-1-yl)thiazol-2-ylthio]-N-{ [4-(3,4-dichlorobenzyl)morpholin-2-yl] methyl}acetamide,
(2S)-[4-(carbamoylmethyl)thiazol-2-ylthio]-N-{[4-(3,4-fluorobenzyl)morpholin-2-yl]methyl}acetamide,
(2S)-[4-(carbamoylmethyl)thiazol-2-ylthio]-N-{[4-(4-fluorobenzyl)morpholin-2-yl]methyl}acetamide,
(2S)-(4-carboxy-5-methylthiazol-2-ylthio)-N-{[4-(3,4-dichlorobenzyl)morpholin-2-yl]methyl}acetamide,
(2S)-(4-carbamoyl-5-methylthiazol-2-ylthio)-N-{[4-(3,4-dichlorobenzyl)morpholin-2-yl]methyl}acetamide,
(2S)-(4-carbamoylthiazol-2-ylthio)-N-{[4-(3-chloro-4-fluorobenzyl)morpholin-2-yl]methyl}acetamide,
(2S)-[4-(2-amino-2-oxoethyl)aminocarbonylthiazol-2-ylthio]-N-{[4-(3,4-difluorobenzyl)morpholin-2-yl] methyl}acetamide,
(2S)-(5-amino-1,3,4-thiadiazol-2-ylthio)-N-{[4-(3-chlorobenzyl)morpholin-2-yl]methyl}acetamide,
(2S)-(5-amino-1,3,4-thiadiazol-2-ylthio)-N-{[4-(3,4-difluorobenzyl)morpholin-2-yl]methyl}acetamide,
(2S)—N-{[4-(3,4-dichlorobenzyl)morpholin-2-yl]methyl} (pyrimidin-2-ylthio)acetamide,
(2S)-(3-acetyl-2-oxo-2H-chromen-6-ylthio)-N-{[4-(3,4-dichlorobenzyl)morpholin-2-yl]methyl}acetamide,
(2S)—N-{[4-(3,4-difluorobenzyl)morpholin-2-yl]methyl} (6-oxo-1,6-dihydropyridazin-3-ylthio)acetamide,
(2S)-[6-(carbamoylmethyl)pyrazin-2-ylthio]-N-{[4-(3,4-dichlorobenzyl)morpholin-2-yl]methyl}acetamide,
(2S)-4-(cyclopentanesulfonyl)-N-{[4-(3-chloro-4-fluorobenzyl)morpholin-2-yl]methyl}butylamide,
(2S)-[4-(carboxymethyl)thiazol-2-ylthio]-N-{[4-(3,4-dichlorobenzyl)morpholin-2-yl]methyl}acetamide,
(2S)-[4-(carboxymethyl)thiazol-2-ylthio]-N-{[4-(3,4-dichlorobenzyl)morpholin-2-yl]methyl}acetamide hydrobromide,
(2S)-[4-(2-carboxypropan-2-yl)thiazol-2-ylthio]-N-{[4-(3,4-dichlorobenzyl)morpholin-2-yl]methyl}acetamide,
(2S)-(5-amino-1,3,4-thiadiazol-2-ylthio)-N-{[4-(3,4-difluorobenzyl)morpholin-2-yl]methyl}acetamide,
(2S)—N-{[4-(3,4-difluorobenzyl)morpholin-2-yl]methyl}-(6-oxo-1,6-dihydropyridazin-3-ylthio)acetamide,
(2S)-[4-(carboxymethyl)thiazol-2-ylthio]-N-{[4-(3,4-dichlorobenzyl)morpholin-2-yl]methyl}acetamide,
(2S)-[4-(carboxymethyl)thiazol-2-ylthio]-N-{[4-(3,4-dichlorobenzyl)morpholin-2-yl]methyl}acetamide,
(2S)[4-(3-aminophenyl)thiazol-2-ylthio]-N-{[4-(3,4-dichlorobenzyl)morpholin-2-yl]methyl}acetamide,
(2S)-[4-(3-carbamoyl-4-hydroxyphenyl)thiazol-2-ylthio]-N-{[4-(3,4-dichlorobenzyl)morpholin-2-yl] methyl}acetamide,
(2S)—N{[4-(3,4-dichlorobenzyl)morpholin-2-yl]methyl}-[4-(pyridin-4-yl)thiazol-2-ylthio]acetamide,
(2S)—N-{[4-(3,4-dichlorobenzyl)morpholin-2-yl]methyl}-[4-(3,4-dimethoxyphenyl)thiazol-2-ylthio]acetamide,
(2S)-(4-carbamoylthiazol-2-ylthio)-N-{[4-(3,4-dichlorobenzyl)morpholin-2-yl]methyl}acetamide,
(2S)-{4-[(2-amino-2-oxoethyl)aminocarbonyl]thiazol-2-ylthio}-N-{[4-(3,4-dichlorobenzyl)morpholin-2-yl] methyl}acetamide,
(2S)—N{[4-(3,4-dichlorobenzyl)morpholin-2-yl]methyl}-[4-(5-methyl-1,2,4-oxadiazol-3-yl)thiazol-2-ylthio]acetamide hydrochloride,
(2S)-(5-amino-SH-indeno[1,2-d]thiazol-2-ylthio)-N-{[4-(3,4-dichlorobenzyl)morpholin-2-yl]methyl}acetamide,
(2S)-(4-carboxyphenylthio)-N-{[4-(3,4-dichlorobenzyl) morpholin-2-yl]methyl}acetamide,
(2S)-{4-[(2-amino-2-oxoethyl)aminocarbonyl]phenylthio}-N-{[4-(3,4-dichlorobenzyl)morpholin-2-yl] methyl}acetamide,
(2S)-{4-[(2-carboxyethyl)aminocarbonyl]thiazol-2-ylthio}N-{[4-(3,4-dichlorobenzyl)morpholin-2-yl] methyl}acetamide hydrochloride,
(2S)-(5-acetamino-1,3,4-thiadiazol-2-ylthio)-N-{[4-(3,4-dichlorobenzyl)morpholin-2-yl]methyl}acetamide,
(2S)-4-(4-carbamoylthiazol-2-ylthio)-N-{[4-(3,4-dichlorobenzyl)morpholin-2-yl]methyl}butyramide hydrochloride,
(2S)—N-{[4-(3,4-dichlorobenzyl)morpholin-2-yl]methyl}-[4-(1H-tetrazol-5-yl)thiazol-2-ylthio]acetamide,
(2S)—N-{[4-(3,4-dichlorobenzyl)morpholin-2-yl]methyl}-([1,3]thiazolo[5,4-b]pyridin-2-ylthio)acetamide,
(2S)-(E)-[4-(2-carbamoylethen-1-yl)thiazol-2-ylthio]-N-{ [4-(3,4-dichlorobenzyl)morpholin-2-yl] methyl}acetamide,
(2S)-[4-(carbamoylmethyl)thiazol-2-ylthio]-N-{[4-(3,4-difluorobenzyl)morpholin-2-yl]methyl}acetamide,
(2S)-[4-(carbamoylmethyl)thiazol-2-ylthio]-N-{[4-(4-fluorobenzyl)morpholin-2-yl]methyl}acetamide,
(2S)-(4-carboxy-5-methylthiazol-2-ylthio)-N-{[4-(3,4-dichlorobenzyl)morpholin-2-yl]methyl}acetamide,
(2S)-(4-carbamoyl-5-methylthiazol-2-ylthio)-N-{[4-(3,4-dichlorobenzyl)morpholin-2-yl]methyl}acetamide,
(2S)-(4-carbmoylthiazol-2-ylthio)-N-{5[4-(3-chloro-4-fluorobenzyl)morpholin-2-yl]methyl}acetamide,
(2S)-[4-(2-amino-2-oxoethyl)aminocarbonylthiazol-2-ylthio]-N-{[4-(3,4-difluorobenzyl)morpholin-2-yl] methyl}acetamide,
(2S)-(5-amino-1,3,4-thiadiazol-2-ylthio)-N-{[4-(3-chlorobenzyl)morpholin-2-yl]methyl}acetamide,
(2S)-(5-amino-1,3,4-thiadiazol-2-ylthio)-N-{[4-(3,4-difluorobenzyl)morpholin-2-yl]methyl}acetamide,
(2S)—N-{[4-(3,4-dichlorobenzyl)morpholin-2-yl]methyl}-(pyrimidin-2-ylthio)acetamide,
(2S)-(3-acetyl-2-oxo-2H-chromen-6-ylthio)-N-{[4-(3,4-dichlorobenzyl)morpholin-2-yl]methyl}acetamide,
(2S)—N{[4-(3,4-difluorobenzyl)morpholin-2-yl]methyl}-(6-oxo-1,6-dihydropyridazin-3-ylthio)acetamide,
(2S)-[6-dichlorobenzyl)morpholin-2-yl]methyl}acetamide,
(2S)-4-(cyclopentanesulfonyl)-N-{[4-(3-chloro-4-fluorobenzyl)morpholin-2-yl]methyl}butyramide.

The disclosure further contemplates methods wherein the CCR3 inhibitory agent is comprised of one of the following phenoxy or phenylsulfonamide small molecule CCR3 antagonists (further described in U.S. Pat. No. 9,206,186, incorporated herein by reference in its entirety and particular with respect to its description of the following compounds)

all of which exhibit a binding $IC_{50}$ less than 100 nM and a calcium influx assay $IC_{50}$ less than 100 nM:

N—(R)-(+)-(1-aza-bicyclo[2.2.2]oct-3-yl)-5-cyano-2-(3,5-dichloro-phenoxy)-benzenesulfonamide, 5-cyano-2-(3,5-dichloro-phenoxy)-N-(2-dimethylamino-ethyl)-N-[2-(2,5-dioxo-pyrrolidin-1-yl)ethyl]-benzene-sulfonamide, 4-(3,5-dichloro-phenoxy)-3-[(3S)-(1H-indol-3-ylmethyl)-piperazine-1-sulfonyl]-benzonitrile, 4-(3,5-dichlorophenoxy)-3-{[2-(1H-1,2,4-triazol-1-ylm-ethyl)-1-piperazinyl]sulfonyl}benzonitrile hydrochloride.

The disclosure also further contemplates methods wherein the CCR3 inhibitory agent is comprised of the bipiperidine CCR3 antagonists described U.S. Pat. No. 7,705,153, incorporated herein by reference in its entirety) all of which exhibit a Ki value of between 3 nM and 50 nM.

2. Antibodies

Optionally, the methods of the disclosure comprise administration to a subject antibodies specific for CCR3 or its ligand, Eotaxin-1/CCL11. Such antibodies are known to those having ordinary skill in the art. These include, by way of example and not limitation, MAB320-SP and MAB155-SP (R&D Systems, Minneapolis, MN), MA5-23831 (ThermoFisher Scientific, Waltham, MA), and Cat #12-1939-42 (Invitrogen, Waltham, MA). Additional examples can be found in Senechal S et al., Lab Investig 82:929-39 (2002) and Williams T J, Front. Immunol. 6(84) (2015) (CAT-213, iCo-008, Bertilimumab). The antibodies may be administered systemically (e.g., IV) or by IVT injection.

B. CO-CRYSTALS AND SALTS, FORMULATIONS, DOSAGE FORMS/INGREDIENTS AND DOSAGES

The disclosure further contemplates aspects wherein co-crystals and salts of Compound 1 or its analogs are administered as CCR3 inhibitory agents. The disclosure further contemplates aspects using formulations of Compound 1 and its analogs. Use of various dosage forms, ingredients, and dosages of Compound 1 and its analogs (or any of the CCR3 inhibitory agents described herein) are also contemplated by the disclosure and suitable for use in any of the methods described herein. Examples of these aspects may be found in PCT Patent Publication Number WO2018/187473, U.S. patent application Ser. No. 12/727,318, U.S. patent application Ser. No. 13/596,225, U.S. patent application Ser. No. 14/175,082, U.S. patent application Ser. No. 13/267,417, U.S. patent application Ser. No. 14/160,646, U.S. patent application Ser. No. 14/572,889, U.S. patent application Ser. No. 13/851,547, U.S. patent application Ser. No. 13/851,564, and U.S. patent application Ser. No. 13851538 which are incorporated by reference in their entirety as if set forth herein.

C. DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The term "about" means 5% more or less of the specified value. Thus, about 100 minutes could also be read as from 95 to 105 minutes.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain aspects, the subject is a non-human mammal. In some aspects, the subject is a farm animal. In other aspects, the subject is a pet. In some aspects, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain aspects the subject are humans. The term subject is also meant to include a person or organism of any age, weight or other physical characteristic, where the subjects may be an adult, a child, an infant (including premature infants) or a newborn.

As used herein, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of an aging-related disease or disorder in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, rejuvenation of tissue or organs, etc. The therapeutic agent may be administered before, during or after the onset of disease. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease.

As used herein, the term "recommended frequency" refers to the rate of administration over time of a pharmaceutical agent approved by a regulatory agency which has been mandated or suggested whether by product label or other documentation. Said regulatory agency may be, for example, the U.S. Food and Drug Administration, European Medicines Agency, Pharmaceuticals and Medical Devices Agency (Japan), China Food and Drug Administration or other comparable national or regional authority. For off-label or pre- or non-approved use, the "recommended frequency" refers to the rate of administration over time of a pharmaceutical agent as is generally recognized for an indication by those healthcare givers having ordinary skill in the art whether as recommended by experts in the field or used in general common practice. In both cases, the term also includes the frequency given in standard practice as understood by one having ordinary skill in the art.

As used herein, the term "loading dose" refers to the practice of administering monthly doses of an anti-VEGF agent to a subject for a period of time lasting no longer than six months, followed by a variable dosing regimen. Thus, the term "loading dose" encompasses (but is not limited to) administering six doses over the course of six months, five doses over the course of five months, four doses over the course of four months, three doses over the course of three months, or two doses over the course of two months. In an exemplary aspect of the disclosure, the method comprises administering an initial "loading dose" of anti-VEGF agent which comprises administering three monthly doses (i.e., one dose per month every three months) prior to administering subsequent additional doses of anti-VEGF agent at an altered frequency between doses (i.e., at an interval other than once a month, and/or which is less frequent than the recommended dosing of the anti-VEGF agent). The variable dosing regimen may be PRN (pro re nata or as needed) or follow a prescribed regimen such as bimonthly or trimonthly dosing. (Schmidt-Erfurth U et al., Br J Ophthalmol, 98:1144-67 (2014) and Ba J et al., Drug Design, Develop Therapy, 9:5397-405 (2015)). In various aspects, the variable dosing regimen does not comprise monthly administrations of the anti-VEGF agent.

Aflibercept

The recommended frequency derived from the FDA approved label (available at www.accessdata.fda.gov/drugsatfda_docs/label/2017/125387s054lbl.pdf under Reference ID 4102905 herein incorporated by reference) for aflibercept (Eylea®) for neovascular (wet) AMD is 2 mg (0.05 mL) administered by intravitreal injection every 4 weeks (monthly) for the first 3 months (a loading dose), followed by 2 mg (0.05 mL) via intravitreal injection every 8 weeks (2 months). Per the label, although it may be dosed as frequently as 2 mg every 4 weeks, additional efficacy has not been demonstrated in most patients when aflibercept is dosed every 4 weeks compared to every 8 weeks. Some patients may require monthly dosing after the first 12 weeks (3 months).

For the most common uses of aflibercept, nAMD, the labeled dose would result in 7-8 doses per year (1 dose per month). As mentioned in the introduction, the labeled use of anti-VEGF agents does not always tie to the use of these agents in practice due to the burden of use. Two retrospective analyses assessed two large claims databases of treatment-naïve neovascular AMD patients treated with IVT anti-VEGF. The intensity of anti-VEGF therapy and its relationship with visual acuity change in nAMD patients was assessed. The mean number of injections per patient per year in the first year of treatment for aflibercept was 5.1 (0.43 per month) to 7.3 (0.61 per month/median being 7 (0.58 per month) reflecting the burden of treatment and the desire to extend treatment duration. In the second year, it was 4.8 injections (0.4 per month) yet vision still decreased. (MacCumber M, Yu, J S, Sagkriotis A, et al. Injection intervals in treatment-naïve neovascular AMD patients who received anti-VEGF agents: An analysis of the IRIS Registry, American Academy of Ophthalmology, San Francisco, 2019:PO471).

It was determined that patients who received fewer anti-VEGF injections experience worse visual outcomes compared with those receiving fixed, frequent anti-VEGF therapy. (Ciulla T A et al., Ophthalmology Retina, 4:19-30 (2020)). In addition, even in this suboptimal treatment paradigm, more than 33% of patients in the claims database required treatment frequency of less than 8 weeks with aflibercept in both the first and second year of treatment, showing the need for frequent follow-up and injections.

For macular edema following vein occlusion (RVO), the recommended dose for aflibercept is 2 mg (0.05 mL) administered by intravitreal injection every 4 weeks (monthly).

For diabetic macular edema (DME), the recommended dose for aflibercept is 2 mg (0.05 mL) administered by intravitreal injection every 4 weeks (monthly) for the first 5 injections, followed by 2 mg (0.05 mL) via intravitreal injection once every 8 weeks (2 months). Per the label, although aflibercept may be dosed as frequently as 2 mg every 4 weeks (monthly), additional efficacy has not not demonstrated in most patients when aflibercept was dosed every 4 weeks compared to every 8. Some patients need every 4-week (monthly) dosing after the first 20 weeks (5 months).

For diabetic retinopathy (DR) the recommended dose for aflibercept is 2 mg (0.05 mL or 50 microliters) administered by intravitreal injection every 4 weeks (monthly) for the first 5 injections, followed by 2 mg (0.05 mL) via intravitreal injection once every 8 weeks (2 months). Per the label, although aflibercept may be dosed as frequently as 2 mg every 4 weeks (monthly), additional efficacy has not been demonstrated in most patients when aflibercept was dosed every 4 weeks compared to every 8 weeks. Some patients may need every 4-week (monthly) dosing after the first 20 weeks (5 months).

Bevacizumab

In ophthalmology, oncology drug bevacizumab (Avastin®) is typically aliquoted by compounding pharmacies into microdoses and given by transconjunctival intravitreal injections into the posterior segment. Intravitreal injections for retinal pathologies are typically administered at 4-6-week intervals, although this varies widely based on disease and response. The typical dose is 1.25 mg in 0.05 ml in adults, and half that dose in premature infants. Importantly, bevacizumab has never been approved for ocular use in the US, for any indication. While other doses (2.5 mg) have been evaluated in large trials, no significant benefit has been shown over the 1.25 mg standard dose, although some advocate "super-doses" in certain situations. (See Karth P A et al., *Bevacizumab*, EyeWiki, American Academy of Ophthalmology, (2020) (available at eyewiki.aao.org/Bevacizumab).

For the most common uses of bevacizumab, the labeled dose would result in 12 doses per year (1 dose per month). As mentioned in the introduction, the labeled use of anti-VEGF agents does not always tie to the use of these agents in practice due to the burden of use. A retrospective analysis assessed a large database of treatment-naïve neovascular AMD patients treated with IVT anti-VEGF. The intensity of anti-VEGF therapy and its relationship with visual acuity change in nAMD patients was assessed. The mean number of injections per patient per year for bevacizumab was 7.3 (0.61 per month), with the median being 8 (0.67 per month). It was determined that patients who received fewer anti-VEGF injections experience worse visual outcomes compared with those receiving fixed, frequent anti-VEGF therapy. (Ciulla T A et al., Ophthalmology Retina, 4:19-30 (2020)).

Ranibizumab

The recommended frequency derived from the FDA approved label (available at www.accessdata.fda.gov/drugsatfda_docs/label/2017/125156s111lbl.pdf under Reference ID 4037547 herein incorporated by reference) for ranibizumab (Lucentis®) for neovascular (wet) AMD is one intravitreal injection per month (approximately 28 days). Although not as effective, patients may be treated according to label with 3 monthly doses followed by less frequent dosing with regular assessment. In the nine months after 3 initial monthly doses, less frequent dosing with 4-5 doses on average is expected to maintain visual acuity while monthly dosing may be expected to result in an additional average 1-2 letter gain. Per the label, although not as effective, patients may also be treated with one dose every 3 months after 4 monthly doses. Compared with continued monthly dosing, dosing every 3 months over the next 9 months will lead to an approximate 5-letter (1-line) loss of visual acuity benefit, on average.

For macular edema following retinal vein occlusion (RVO), 0.5 mg (0.05 mL of Lucentis solution) is recommended IVT once per month (approximately 28 days). In Studies RVO-1 and RVO-2, patients received monthly injections of LUCENTIS for 6 months. In spite of being guided by optical coherence tomography and visual acuity re-treatment criteria, patients who were then not treated at Month 6 experienced on average, a loss of visual acuity at Month 7, whereas patients who were treated at Month 6 did not. Patients with RVO should be treated monthly.

For diabetic macular edema (DME), 0.3 mg of Lucentis is recommended to be administered by IVT once per month (approximately 28 days). For diabetic retinopathy 0.3 mg of Lucentis solution is recommended to be administered by IVT once per month (approximately 28 days). For myopic choroidal neovascularization (mCNV), 0.5 mg Lucentis is recommended to be administered by IVT once per month (approximately 28 days) for up to three months with patients being retreated if needed.

For the most common uses of ranibizumab, the labeled dose would result in 12 doses per year (1 dose per month). As mentioned in the introduction, the labeled use of anti-VEGF agents does not always tie to the use of these agents in practice due to the burden of use. Two retrospective analyses assessed two large databases of treatment-naïve neovascular AMD patients treated with IVT anti-VEGF. The intensity of anti-VEGF therapy and its relationship with visual acuity change in nAMD patients was assessed. The mean number of injections per patient per year for the first year of treatment with ranibizumab was 4.9 (0.41) to 7.3 (0.61 per month, with the median being 7 (0.58 per month), reflecting the burden of treatment and the desire to extend treatment duration. In the second year, it was 4.5 injections (0.38 per month) yet vision still decreased. MacCumber M, Yu, J S, Sagkriotis A, et al. injection intervals in treatment-naïve neovascular AMD patients who received anti-VEGF agents: An analysis of the IRIS Registry. American Academy of Ophthalmology, San Francisco, 2019:PO471. It was determined that patients who received fewer anti-VEGF injections experience worse visual outcomes compared with those receiving fixed, frequent anti-VEGF therapy. (Ciulla T A et al., Ophthalmology Retina, 4:19-30 (2020)).

Brolucizumab

The recommended frequency derived from the FDA approved label (available at www.accessdata.fda.gov/drugsatfda_docs/label/2019/761125s000lbl.pdf under BLA reference ID 761125 herein incorporated by reference) for brolucizumab (Beovu®) for neovascular (wet) age-related macular degeneration (wAMD) is 6 mg (0.05 mL of 120 mg/mL solution) monthly (approximately every 25-31 days) for the first three doses (loading dose), followed by one dose of 6 mg (0.05 mL) every 8-12 weeks (determined by the physician). Brolucizumab is a human vascular endothelial growth factor (VEGF) inhibitor administered by intravitreal injection in a single-dose vial. Brolucizumab binds to the three major isoforms of VEGF-A (e.g., VEGF110, VEGF121, and VEGF165) which prevents interaction with receptors VEGFR-1 and VEGFR-2. This inhibits endothelial cell proliferation, neovascularization, and vascular permeability. Brolucizumab is also being investigated for use as a treatment for diabetic macular edema (DME) and macular edema secondary to retinal vein occlusion. For DME, trials have used 6 mg/0.05 mL every 4 weeks for 12 months (available at www.clinicaltrials.gove/ct2/show/NCT03917472 Accession No. NCT03917472 herein incorporated by reference). It is also being investigated for a treatment for diabetic retinopathy (DR) with a dose of 6 mg three times, 6 weeks apart (3×q6 w) and then once every 12 weeks for a total of 93 weeks (www.clinicaltrials.gov/ct2/show/NCT04278417 Accession No. NCT04278417 herein incorporated by reference). Brolucizumab has also been studied as a treatment for retinal vein occlusion, both branched (BRVO) and central (CRVO). For BRVO, treatment is 6 mg every 4 weeks for a total of 6 injections, follow by 48 weeks of individual flexible treatment (IFT) (www.clinicaltrials.gov/ct2/show/NCT03802630 Accession No. NCT03802630 herein incorporated by reference). For CRVO, treatment is also 6 mg every 4 weeks for a total of 6 injections, followed by 48 weeks of individual flexible treatment (IFT) (www.clinicaltrials.gov/ct2/show/NCT03810313 Accession No. NCT03810313 herein incorporated by reference).

Thus, "at a frequency less than the recommended frequency" or "at a frequency less than the frequency given in standard practice" means, in various aspects of the disclosure, that the subsequent administrations of the anti-VEGF agent are administered at a timing interval that is longer than the time between doses employed by recommended frequency of doses or frequency of doses given in standard practice. In various aspects, the time between doses is at least 30 days longer than the time between doses in the recommended frequency of dosing of the anti-VEGF agent. For example, the time between doses is optionally at least (or greater than) four weeks, at least (or greater than) six weeks, at least (or greater than) eight weeks, at least (or greater than) 10 weeks, at least (or greater than) 12 weeks, at least (or greater than) 14 weeks, or at least (or greater than) 16 weeks. In various aspects, the time between doses is optionally at least four weeks longer than the recommended frequency of dosing, at least six weeks longer than the recommended frequency of dosing, at least eight weeks longer than the recommended frequency of dosing, at least 10 weeks longer than the recommended frequency of dosing, at least 12 weeks longer than the recommended frequency of dosing, at least 14 weeks longer than the recommended frequency of dosing, or at least 16 weeks longer than the recommended frequency of dosing. Thus, for illustration only, the FDA's recommended dosing regimen for brolucizumab is one dose of 6 mg (0.05 mL) every 8-12 weeks, and the instant method comprises administering a CCR3 inhibitory agent, administering brolucizumab to the subject after the administering of the CCR3 inhibitory agent, and then administering additional subsequent doses of brolucizumab such that the time between doses is, e.g., more than 12 weeks (resulting in a frequency of dosing that is less than the recommended frequency).

As used herein, the term "refractory" in relation to anti-VEGF treatment refers to a subject who exhibits an incomplete, poor, or declining response to persistent IVT administration of anti-VEGF agents or who is resistant to treatment despite aggressive therapy over an extended period of time. The term also includes subjects classified as nonresponsive, unresponsive, recalcitrant, or resistant to anti-VEGF or who exhibit tolerance to anti-VEGF, exhibit tachyphylaxis to anti-VEGF treatment or are recalcitrant to anti-VEGF treatment. The term also includes, for example, the eye(s) of subjects who are affected by nAMD show persistent fluid collection despite at least three to five monthly consecutive anti-VEGF injections, persistent exudation after at least 6-month regular anti-VEGF therapy, persistent fluid on spectral-domain OCT (SD-OCT) at greater than 30 days after the last of six IVT injections of an anti-VEGF agent at monthly intervals, and persistent exudation as evident on clinical examination and also imaging studies (leakage on fluorescein angiography, or fibrovascular pigment epithelial detachment (PED) with intraretinal fluid (IRF) or subretinal fluid (SRF) on SD-OCT) or increasing hemorrhage compared to baseline after six consecutive injections at monthly intervals. (See, e.g. Yang S et al., Drug Design, Development and Therapy, 10:1857-67 (2016)).

D. RETINA-ASSOCIATED DISEASE INDICATIONS i. Macular Degeneration

Macular degeneration is a clinical term that is used to describe a family of disease that are all characterized by a progressive loss of central vision associated with abnormalities of the choroid, Bruch's membrane, the retinal pigmental epithelium and/or the neural retinalium. These disorders include very common conditions that affect older subjects—such as age-related macular degeneration (AMD) as well as rarer, earlier-onset dystrophies that in some cases can be detected in the first decade of life. Other maculopathies include North Carolina macular dystrophy, Best disease, and Malattia leventinese.

AMD is the leading cause of permanent vision loss for individuals over the age of 65, currently affecting approximately 15 million Americans. AMD affects light-sensitive photoreceptor cells and pigmented epithelial cells in the macula, the center of the retina of the eye. While early cases may not cause total blindness, the disease destroys central vision, making reading, watching electronic monitor screens, and driving difficult to impossible. It has no documented cure, has never demonstrated spontaneous remission, and effective treatments are limited with substantial burden upon patient and caregiver as well as side effects, and must be continued for the duration of the life of the individual.

The retina is a complicated network of nerve cells that changes light into nerve impulses that travel to the brain where they are interpreted as visual images. The central part of the retina, called the macula, is responsible for vision that is needed for reading and other detailed work. Damage to the macula results in poor vision. The most common disease process that affects the macula is AMD. In patients with AMD, retinal photoreceptor and pigment epithelial cells in the macula die over the course of several years. The cell death and gradual visual loss usually do not begin until age 60 or older, thus the name, age-related macular degeneration.

There are two types of AMD: dry macular degeneration and wet macular degeneration. Dry macular degeneration, although more common, typically results in a less severe, more gradual loss of vision. Patients who are affected by early or intermediate dry AMD have gradual loss of central vision due to the death of photoreceptor cells and their close associates, retinal pigmented epithelial (RPE) cells, with deposition of a complex waxy amyloid mixture, termed 'drusen'. Photoreceptors, the cells in the retina that actually 'see' light, are essential for vision. Macrophagic RPE cells are necessary for photoreceptor survival, function and renewal. The advanced form of dry AMD, called geographic atrophy, represents about 10-15% of AMD. Geographic Atrophy (GA) causes atrophy of photoreceptors, RPE and the underlying choriocapillaris. These atrophic scotoma typically start in the periphery, but over time form a ring around, and eventually can close around the fovea leading to complete blindness. Patients initially present with a blind spot in their peripheral vision which gradually grows, causing profound visual impairment. GA can lead to blindness without ever developing into neovascular or wet AMD. There is currently no treatment for Geographic Atrophy. Patients with wet macular degeneration develop new blood vessels under the retina. As the photoreceptor and RPE cells slowly degenerate, there is a tendency for blood vessels to grow from their normal location in the choroid into an abnormal location beneath the retina. This abnormal new blood vessel growth is called choroidal neovascularization (CNV). The abnormal blood vessels leak and bleed, causing hemorrhage, swelling, scar tissue, and severe loss of central vision. Only 10% of patients with AMD have the wet or exudative type, but it is responsible for 90% of all blindness resulting from AMD. One of the utilities of CCR3 inhibitory agents is the treatment of the inflammation and neovascularization (through a specific mechanism) resulting from disorders such as wAMD, dAMD, and Geographic Atrophy.

ii. Retinal Vein Occlusion (RVO)

Retinal Vein Occlusion, also known as RVO, occurs when venous occlusion prevents oxygen-depleted blood from flowing out of the eye's vasculature. As a result of reduced flow of oxygen-depleted blood in the eye, oxygen-rich blood is inhibited from reaching the retina's surface layers, resulting in a hypoxic state. In response, the surface layers of the retina produce pro-angiogenic factors which contribute to the development of abnormal macular edema and neovascularization. RVO can be termed either CRVO (central) or BRVO (branch) for the location of the venous occlusion. One of the utilities of CCR3 inhibitory agents is the treatment of the macular edema and neovascularization resulting from RVO.

iii. Diabetic Retinopathy

Diabetic Retinopathy is a complication from diabetes that can cause blindness. Diabetic Retinopathy can develop in subjects with either Type 1 or Type 2 diabetes, which is associated with loss of control of blood sugar content. Long term lack of glycemic control causes damage to the blood vessels of the retina, eventually causing damage to the retinal tissue via the signaling of neovascularization, which can lead to inflammation, scarring, and edema. Improper regulation of the growth of these blood vessels ensues, resulting in vessels that leak readily. Symptoms, which may be subtle in early forms the disease, include spots or floaters in the subject's vision, blurred vision, fluctuating vision, impaired color vision, dark/empty areas of vision, and vision loss, usually affecting both eyes.

Two types of Diabetic Retinopathy exist: Early Diabetic Retinopathy, or Non-proliferative Diabetic Neuropathy (NPDR) and Advanced Diabetic Retinopathy, or Proliferative Diabetic Retinopathy. NPDR is marked by less pronounced neovascularization and vessel growth; however the walls of the retinal blood vessels weaken and the occurrence of microaneurysms can be present. These microaneurysms can protrude and leak fluid and blood into the retina. As more blood vessels are blocked, the NPDR gets more severe. Retinal nerve fibers as well as the macula (central part of the retina) can swell, a condition known as macular edema. In Advanced Diabetic Retinopathy (or Proliferative Diabetic Retinopathy), blood vessels that have been damaged close off, which causes new, abnormal blood vessel growth, and hemorrhage and leakage into the vitreous of the eye becomes more common. Scar tissue that results from the new blood vessel growth can cause retinal detachment as well as increased eye pressure—ultimately causing damage to the optic nerve and glaucoma. When there is leakage of fluid within the retina, this is called Diabetic Macular Edema (DME), a sequelae of PDR which accumulates fluid underneath or within the retina leading to a loss of vision.

DME although late in the DR cascade, can often be the first symptom noticed diabetic retinopathy. It is a frequent symptom that brings patients to the physician since it is an acute, common manifestation of diabetic retinopathy. Current Anti-VEGF medications have labeled indications for both DME and/or Diabetic Retinopathy. Although the two terms are sometimes used interchangeably in discussing the underlying disease of DR, DR encompasses a much wider range of symptomless to very severe and immediately vision threatening disease, similar to the term AMD. One of the utilities of CCR3 inhibitory agents is the treatment of the macular edema and neovascularization resulting from DR and DME.

iv. Myopic CNV

Pathological Myopia, or nearsightedness, can cause choroidal neovascularization due to a stretching of the layers of the retina, resulting in the creation of new blood vessels. The disease can happen in younger patients but is more common in elderly patients. Raecker M E et al., *Diagnosis and Treatment of CNV in Myopic Macular Degeneration*, EyeNet Mag, (April 2015):35-37. One of the utilities of CCR3 inhibitory agents is the treatment of the neovascularization resulting from CNV.

v. Retinopathy of Prematurity

Affecting prematurely born babies, Retinopathy of Prematurity (ROP) is an eye disease associated with both oxygen toxicity and local hypoxia. These conditions are thought to contribute to the development of ROP. The underlying pathophysiology of the disease is that hypoxic conditions lead to stimulation of pro-angiogenic factors that cause disorganized growth of blood vessels with result in scarring and retinal detachment. Some patients with ROP can have it in a mild form and fully recover without therapeutic intervention, but in others it can lead to permanent blindness. The exact cause of the disease is unknown but leading hypotheses are that supplemental oxygen either causes local retinal hypoxia through vasoconstriction which triggers neovascularization, or that normal vascular processes are blunted by supplemental oxygen, but when it is suddenly removed results a rapid proliferation of vascular and fibrovascular disease. Surgery and therapeutic intervention are current therapies to treat the disease in its severe form. Surgical therapy can include sclera buckling and/or vitrectomy for retinal detachment, and some experiment with low dose anti-VEGF therapy, although the long-term impact of inhibiting VEGF in infants is unknown given its broad role in angiogenic growth throughout the quickly growing body of an infant. Laser induced photocoagulation is however the mainstay of ROP treatment currently. The CCR3 inhibitory agents have utility in the prevention of neo-vascularization associated with ROP.

E. METHODS OF DIAGNOSING AND MONITORING FOR IMPROVEMENT OF RETINA-ASSOCIATED DISEASE i. Introduction

The disclosure further provides methods of diagnosing retina-associated disease. Such methods may include, by way of example, and not limitation, visual acuity (VA) tests including but limited to best corrected visual acuity (BCVA), macular degeneration or Amsler grids, retina examination with dilated pupils, fundus photography, fluorescein angiography, or optical coherence tomography (OCT) which can determine such endpoints as central retinal thickness (CRT). Any of the techniques described herein may be employed to examine the eye of a subject to determine whether treatment with an anti-VEGF agent is warranted.

ii. Visual Acuity (VA)

One method that can diagnose or determine disease progression/improvement is testing for visual acuity. Methods for testing for visual acuity are well-known to those having ordinary skill in the art. Visual acuity tests the sharpness of the subject's vision, often using an "eye chart" the most common of which is the Snellen eye chart. Other methods of testing for visual acuity include use of the Early Treatment Diabetic Retinopathy Study (ETDRS) chart, which, as with other VA tests, can be used to diagnose and measure progression/improvement in visual acuity of subjects with retina-associated diseases such as, by way of example and not limitation, macular degeneration, central retinal vein occlusion, retinopathy of prematurity, and diabetic retinopathy. (See Bokinni, Y, et al., Eye 29:1085-91 (2015)).

A preferred method of determining improvement in visual acuity in a patient is determining whether the subject, after treatment, is able to identify more letters on the Snellen, ETDRS, or other similar charts than they were able to before treatment. Since such visual acuity tests require communication between the subject and the medical professional (e.g., reading letters out loud), it is difficult to get analogous readouts in visual acuity when testing on animal models in pre-clinical studies. Visual acuity tests used in clinical retinal practice typically test for best corrected visual acuity (BCVA) or the visual acuity obtained with correction (which can be glasses, contact lenses, etc.) as the testing is not concerned with underlying refractive correction, but the underlying health of the retina.

Visual acuity has the advantage of being a clinical endpoint that can be independent of other visual tests that depend upon observation of retinal vascularization or neovascularization such as fundus photography/observation, fluorescein angiography, or even optical coherence tomography. That is, if an improved effect on visual acuity is due not to a mechanism affecting the retinal vasculature, then this test can still reveal the efficacy of a treatment and is an important and real-world measurement of patient function.

iii. Macular Degeneration/Amsler Grids

One method that is commonly used to diagnose macular degeneration and to determine disease progression is the use Amsler (macular degeneration) grids, the methods of which are well known to those having ordinary skill in the art. The grid comprises a square similar in appearance to graph paper, with dark lines forming a square grid and a dark dot in the middle of the square. Covering each eye in succession, the subject focuses each individual eye on the dark dot and takes note if any of the lines of the grid are broken, distorted, wavy, or blurry.

iv. Comprehensive Retinal Examination with Pupil Dilation

Comprehensive retinal examination with pupil dilation is a method through which the retina may be observed directly by a practitioner such as an optometrist or ophthalmologist and is well-known to those having ordinary skill in the art. The practitioner administers dilating eye drops to the subject. The drops can be of two types of mydriatic medications, either administered together or separately. One stimulates contraction of the muscles that dilate the pupil (e.g., phenylephrine), and the other type relaxes the muscles that make the pupil constrict (e.g., cyclopentolate). Pupil dilation allows the practitioner to better observe a larger field of the retina during eye examination.

Comprehensive retinal examination with pupil dilation allows ophthalmologists to diagnose and determine disease progression of various eye and retina-associated diseases such as, by way of example and not limitation, glaucoma, diabetic retinopathy, retinopathy of prematurity, retinal vein occlusion, and age-related macular degeneration. Telltale signs of these diseases that can be determined by fundus photography include swell or leaking of blood vessels in the retina, abnormal growth of blood vessels in or beneath the retina, and deterioration of the macula of the retina.

v. Fundus Photography

Similar to retinal examination with pupil dilation, fundus photography is a method through which the retina may be photographed directly and is well-known to those having ordinary skill in the art. (Saine, P J, et al., *Fundus Photography Overview*, Ophthalmic Photography: Retinal Photography, Angiography, and Electronic Imaging, Butterworth-Heinemann Medical (2nd ed.)). The procedure includes pupil dilation, with the patient sitting before the fundus camera. A flash sends light into the patient's eye, creating a fundus photograph or image of the retina. The photography can be performed with various colored filters, or the patient can be administered dues such as fluorescein to aid in imaging.

A fundus camera is a specialized, low power microscope attached to a camera. The angle of acceptance of the lens can create different outputs. A 30-degree angle is considered by those having ordinary skill in the art to be the normal view of the retina. Wide angle fundus cameras are capable of capturing images between 45 and 140 degrees, and narrow angle fundus cameras have angle views of 20 degrees or less.

As with comprehensive retinal examination with pupil dilation, fundus photography allows ophthalmologists to diagnose and determine disease progression of various eye and retina-associated diseases such as, by way of example and not limitation, glaucoma, retinopathy of prematurity, diabetic retinopathy, retinal vein occlusion and age-related macular degeneration. Telltale signs of these diseases that can determined by fundus photography include swell or leaking of blood vessels in the retina, abnormal growth of blood vessels in or beneath the retina, scotomas or fibrotic scarring and deterioration of the macula of the retina.

vi. Fluorescein Angiography

Fluorescein angiography is a method through which the blood vessels of the retina can be evaluated and is well-known to those having ordinary skill in the art. It is used most commonly for diagnosing or measuring progression of choroidal neovascularization in any of the retinal diseases marked by new vessel growth, including but not limited to wAMD, DME, RVO, and ROP.

Fluorescein dye is injected into the vein of a subject (whose eyes have been dilated prior) in order for the dye to travel to the eye and the vasculature of the retina. Before the dye is injected, baseline photos of the retina are taken. When it is determined that the dye has entered retinal vasculature, additional photos are taken of the retina over the span of one to several minutes. Viewing the photographs, the ophthalmologist can determine if any vessel growth has occurred and whether any of the dye leaked from the vessels, which helps them understand where new and fragile blood vessels have developed, and if leakage into the retina is occurring.

vii. Optical Coherence Tomography (OCT)

OCT is a non-invasive test that provides high-resolution cross-sectional images of a retina and employs light waves to produce the images. (Fujimoto, J G, et al., *Neoplasia,* 2(1-2):9-25 (January. 2000)). OCT allows for each of the distinctive layers of the retina to be imaged. Accordingly, an ophthalmologist is given the means through which they can map the retina and determine its thickness. Central thickness of the retina, if increased, can represent fluid accumulation under or within the central retina, 'retinal swelling,' and can be measured by OCT. The value obtained is often the CSF thickness, which refers to the retinal thickness in the central 1 mm subfield of the retina. By way of example, and not limitation, OCT allows for: the central retinal thickness (CRT) of the subject's retina to be precisely measured anywhere in the retina; the central macular thickness (CMT) of the subject's retina to be precisely measured in the central part of the retina (macula); and the central subfield thickness (CSF or CSFT or CST) of the subject's retina to be precisely measured in the central 1 mm subfield of the retina. The methods of performing an OCT test as well as determining CRT, CMT, and CST are well-known to those of skill in the art.

OCT can be performed using eye drops which dilate the pupils and allow better examination of the subject's retinas. Once the pupils are fully dilated, the subject the OCT scanner may scan the subject's eyes in a non-invasive fashion. OCT can help to diagnose many retina-associated conditions/diseases including macular edema, age-related macular degeneration, glaucoma, diabetic retinopathy, and retinopathy of prematurity.

viii. Angiography OCT (angio-OCT/aOCT/OCT-A)

Angiography OCT is a non-invasive technique that images retinal and choroidal microvasculature. (Fingler J et al., Investig Ophthalmol Vis Sci, 49(11):5055-59 (2008)). Laser light reflectance is used on the surface of the moving red blood cells which results in a depiction of microvessels. Thus, injectable dyes are unnecessary in order to obtain a scan of the subject's retina. Multiple scans are taken over time which allows detection of areas with high, medium, and low to no blood flow rates.

Angio-OCT has been useful in diagnosing and researching several retinal conditions. (See Sousa D C et al., *Optical Coherence Tomography Angiography*, EyeWiki, American Academy of Ophthalmology, (2019) (available at eyewiki-.aao.org/Optical_Coherence_Tomography_Angiography). These include both dry and wet age-related macular degeneration (Waheed N K et al., Developments in Ophthalmology 56:91-100 (2016) and de Carlo T E et al. Int J Rein Vitr. 1(1):5 (2015)), diabetic retinopathy (Samara W A et al., Ophthalmology, 124(2):235-44 (2017)), central serous chorioretinopathy (de Carlo T E et al., Ophthalmic Surgery, Lasers Imaging Rein. 47(2):128-33 (2016)), central retinal vein occlusion (Wakabayashi T et al., Investig Ophthalmology Vis Sci, 58(4):2087 (2017)), macular telangiectasia (Zhang Q et al., Retina, 35(11):2285-99 (2015)), choroidal neovascular membranes (Querques L et al., Br J Ophthalmol, 309162 (2016)), glaucoma (de Carlo T E et al. Int J Rein Vitr. 1(1):5 (2015)), and uveitis (Kim A Y et al., Am J Ophthalmol, 171:101-12 (2016)). Both Angio-OCT and OCT can also be utilized to detect subretinal fluid (SRF), intra-retinal fluid (IRF), choroidal neovascularization (CNV), and retinal pigmental epithelium (RPE) thickness and detachment (Faridi A et al., Ophthalmol Retina, 1(4): 294-303 (2017)) which may be used to monitor morphological characteristics of a subject's retina. Angio-OCT is rapidly developing, and wide-field aOCT can provide an even larger cross section of the retina, and various types of OCT and aOCT can provide higher levels of detail for better resolution of images.

F. METHODS OF DETERMINING WHETHER TREATMENT OR RETREATMENT WITH ANTI-VEGF THERAPY IS WARRANTED

The methods of the disclosure optionally further comprise examining the eye of the subject to determine whether a subject who has been treated with a CCR3 inhibitory agent should be treated with an anti-VEGF therapy. A determination step may be included in the method regardless of whether the subject is naïve (i.e., not previously treated with an anti-VEGF agent), has been treated previously and responded to anti-VEGF therapy, or is refractory to anti-VEGF therapy. In various aspects, the method further comprises administering anti-VEGF therapy to the subject based on the determination of whether the subject should be treated. Methods of determining whether a subject should be treated with an anti-VEGF agent involve examination of the eye of the subject using any one or more suitable techniques, such as the techniques described herein.

For example, the method may comprise determining whether the central retinal thickness (CRT) of the eye with the retinal disorder/condition has increased using, e.g., OCT. In an aspect of the disclosure, an additional dose of anti-VEGF agent is provided in response to increased CRT of 50 μm, 100 μm, 150 μm, 200 μm or more. (See e.g., Patel A V et al., Int Ophthalmol Clin, 55(4):103-12 (2015) which is incorporated herein by reference in its entirety). Alternatively or in addition, the method may comprise determining whether an anti-VEGF therapy should be administered based on a decrease in visual acuity or best corrected visual acuity by 1 letter, 2 letters, 3 letters, 4 letter, 5 letters, or more. (See e.g., Id. and Martin D F et al., Ophthalmology, 119(7):1388-98 (2012) which are incorporated herein by reference in their entirety). Alternatively or in addition, the method may comprise determining whether an anti-VEGF therapy should be administered based on new persistent hemorrhage, increased fluid on OCT, dye leakage on leakage on fluorescein angiography, reports of metamorphopsia (distorted images) or scotoma (blind spots) or other changes in vision reported by the subject. Alternatively or in addition, the method may comprise determining whether there are signs of active choroidal neovascularization, the presence of subretinal, intraretinal, or sub-RPE fluid on OCT, the presence of subretinal or intraretinal hemorrhage, the presence of persistent subretinal or intraretinal hemorrhage, decreased visual acuity relative to the last visit without another explanation, increased lesion size on fluorescein angiography relative to the last angiogram, or leakage on fluorescein angiogram. (See Martin supra and the CATT Manual of Procedures, 2011 available at www.med.upenn.edu/cpob/assets/user-content/documents/CATTManualofProceduresJan2011.pdf which is herein incorporated by reference in its entirety.). The method may then comprise administering one or more subsequent doses of anti-VEGF agent.

Determining whether the subject should be treated with the anti-VEGF agent can, for example, be performed at follow-up visits to a physician, ophthalmologist, or other qualified healthcare professional. Such visits may be regular (e.g., monthly), as requested by the patient, or otherwise as needed.

G. REAGENTS, DEVICES, AND KITS

Also provided are reagents, devices, and kits thereof for practicing one or more of the above-described methods. The subject reagents, devices, and kits thereof may vary greatly. Reagents and devices of interest include those mentioned above with respect to the methods of administering the CCR3 inhibitory agents in the subject.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g. diskette, CD, portable flash drive, etc., on which the information has been recorded. Yet another means that may be present is a website address which may be used via the internet to access the information at a remote site. Any convenient means may be present in the kits.

The following examples are provided by way of illustration and not by way of limitation.

H. EXAMPLES i. Pharmaceutical Preparation

The pharmaceutical compositions that are administered to subjects with retina-associated disease that are comprised of the compounds, co-crystals, and salts described above can be synthesized, made, and formulated using the examples disclosed in U.S. Patent Application Publication Nos. 2013/0266646, 2016/0081998, U.S. Pat. Nos. 8,278,302, 8,653,075, RE 45323, 8,742,115, 9,233,950, and 8,680,280, which are herein incorporated by reference in their entirety. Additional CCR3 inhibitory agents are also described in detail in Section 0 above.

ii. The Investigational Product

The investigational product of the invention ("Compound 1") conforms to the following chemical structure:

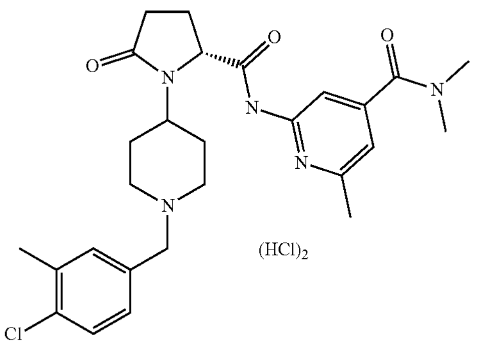

$(HCl)_2$

Those having ordinary skill in the relevant art would recognize that the compounds, co-crystals, salts, and formulations described previously in U.S. patent application Ser. Nos. 12/727,318, 13/596,225, 14/175,082, 13/267,417, 14/160,646, 14/572,889, 13/851,547, 13/851,564, 13/851,538 and PCT patent application number WO2018/187473 can also be used in these examples. Those having ordinary skill in the relevant art would also recognize that any CCR3 antagonists described previously above can also be used in these examples.

The investigational product of the invention was made available as 100 mg, 200 mg, and 400 mg film-coated tablets with a biconvex, round or oval shape and a dull red color. The tablets were produced by a dry granulation process and contained microcrystalline cellulose, hydrogen phosphate, croscarmellose sodium, magnesium stearate, polyvinyl alcohol, titanium dioxide, polyethylene glycol, talc, iron oxide red and iron oxide yellow as inactive ingredients. Placebo tablets matching the investigational product were produced by a direct compression process and contained the same inactive ingredients.

I. CLINICAL EXAMPLES i. Refractory Subject Eyes

Subjects with refractory wet Age-Related Macular Degeneration (wAMD) were administered 400 mg of Compound 1 CCR antagonist orally twice per day (BID) for a total dose of 800 mg per day. The treatment regimen of Compound 1 lasted 6-weeks. Refractory subjects for this 6-week regimen were described as having persistent subretinal fluid, intraretinal fluid, and absence of improvement in visual acuity after at least 3 consecutive (approximately 4-6 weeks apart) IVT anti-VEGF injections.

After the end of a clinical trial consisting of 6-weeks of Compound 1 CCR antagonist treatment, and four weeks of clinical trial follow up with no additional treatment, a subject with heavily pre-treated bilateral disease entered back into normal treatment with their physician and was treated or re-treated with α-VEGF agents per physician judgment guided by standard criteria such as new CNV activity on OCT/angiography OCT (angio-OCT or aOCT) or foveal subretinal fluid (SRF)/intra-retinal fluid (IRF) or PED. Different α-VEGF agents (described in FIGS. 4-5, 9-10, 14-15, 19-21 and Tables D and H) were administered by intra-vitreal injection. For aflibercept, 2 mg in 0.05 mL was given per single intravitreal injection. For bevacizumab, 1.25 mg in 0.05 mL was given per single intravitreal injection. For ranibizumab, 0.5 mg in 0.05 mL was given per single intravitreal injection. Brolucizumab was not approved at the time and was not used in these clinical examples.

All OCT tests were performed using REVO NX (Optopol Technology, Poland). A 3-dimensional (3D) scanning protocol covering a 7×7 mm area was used (1024 A-scans×64 tomograms). The central retinal thickness (CRT) was measured automatically (software version 9.6). The detection of the fovea and the accuracy of layers segmentation was checked by the operator. If necessary, the fovea location and the outer retinal boundaries were corrected manually by moving the pointer to the desired position. In such cases, the central macular thickness value was recalculated. Subretinal and intraretinal fluid presence was assessed manually. SRF was defined as a hyporeflective space between retinal pigment epithelium and the sensory retina, whereas IRF as hyporeflective ovoid or round spaces within the retina. SRF and IRF was distinguished from the outer retinal tubulations (ORTs) and degenerative IRF. The latter were not recognized as a CNV activity sign. CNV activity signs such as neovascular vasculature seen on OCT angiography were monitored. Additionally, lipid exudates and enlargement of RPE elevation were noted.

Different methods are currently being explored to overcome refractory nAMD. These include switching anti-VEGF agents resulting in very limited success in resensitization, increasing anti-VEGF dose resulting in only modest improvement in resensitization, and increasing anti-VEGF dosing frequency resulting in improved resolution of SRF but limited functional improvement. (Fowler S C and Schneider E W, *More frequent dosing for refractory nAMD?*, Retina Specialist, May 13, 2020).

Figure 9:
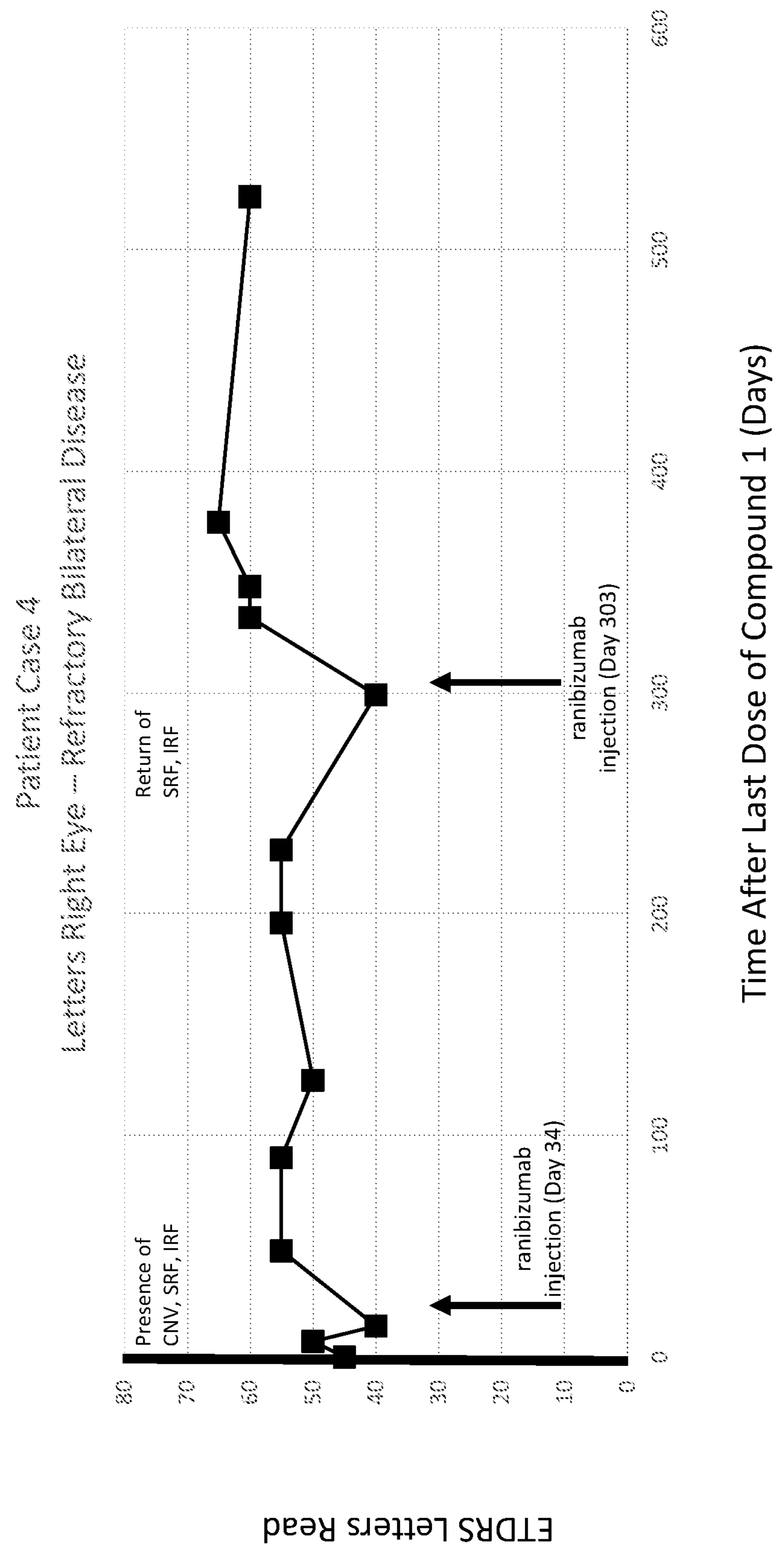
FIG. 9 and FIG. 10 report the number of ETDRS letters read in the two eyes of the subject with refractory, bilateral wAMD. The x-axis depicts time after the last dose of Compound 1 had been administered. Arrows report when an anti-VEGF agent was administered intravitreally (IVT). Notes at the top of the graph annotate changes to morphological features of the retina, particularly the fovea, leading to decision to retreat with an anti-VEGF agent.
Figure 10:
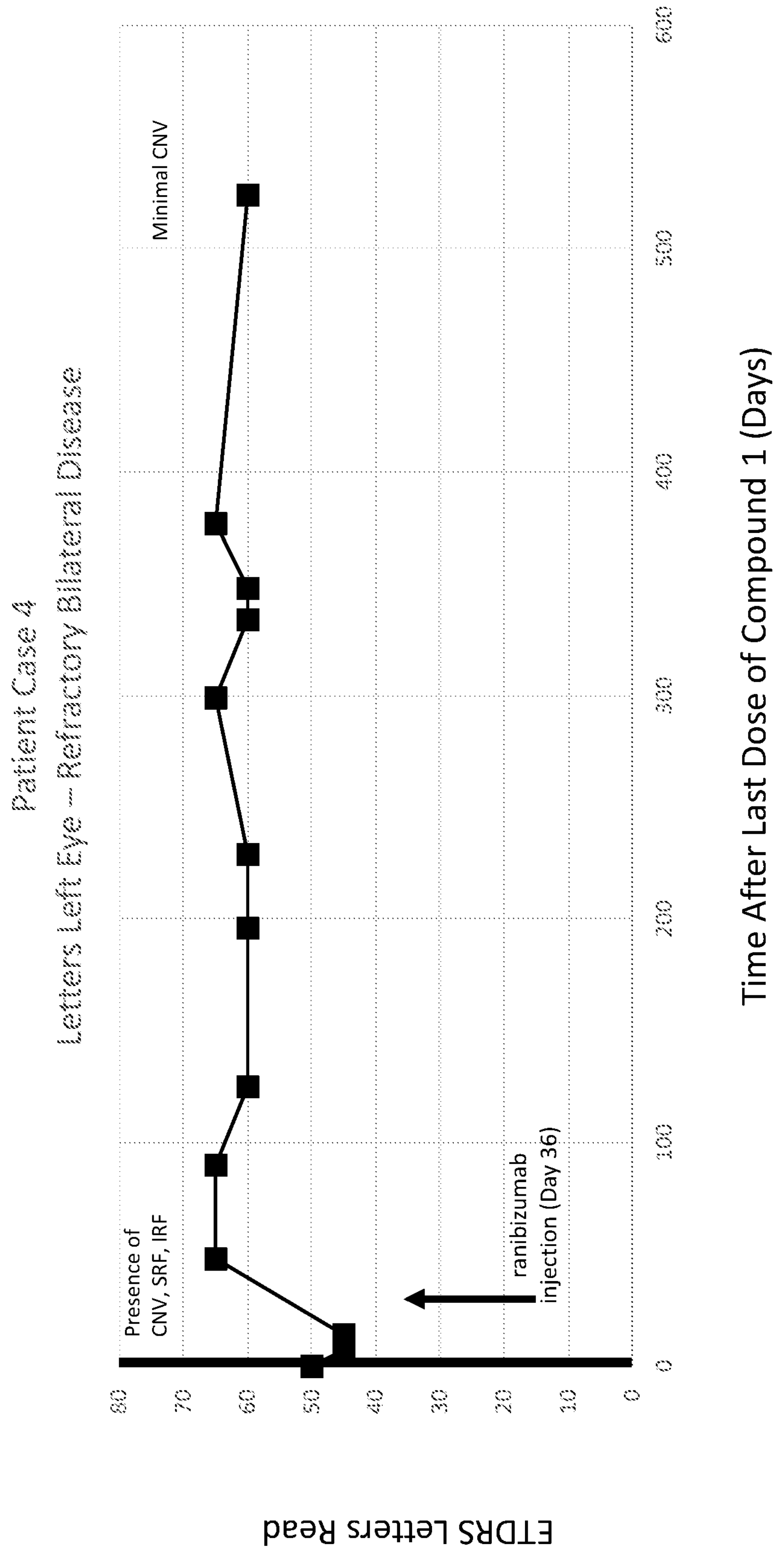
Figure 11:
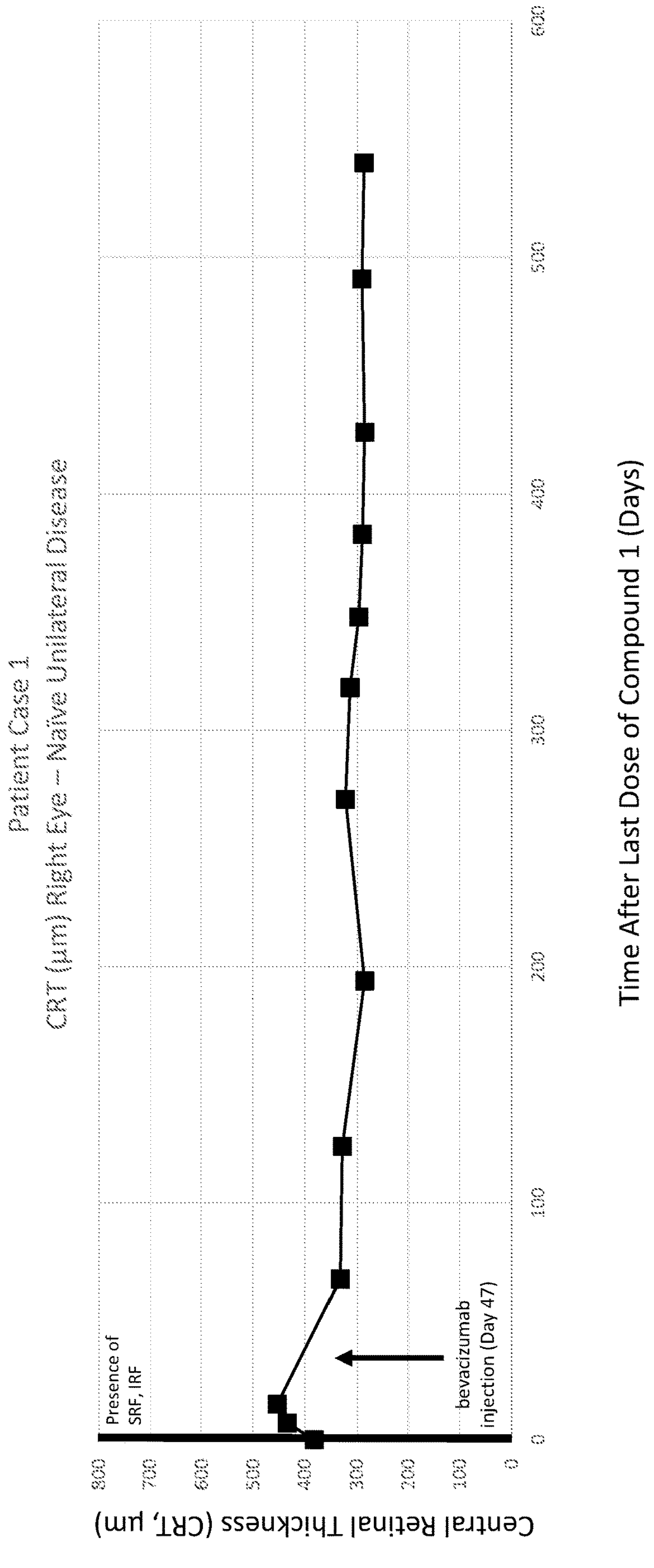
FIG. 11, FIG. 12 and FIG. 13 report central retinal thickness (CRT) in the three subjects with naïve unilateral wAMD. The x-axis depicts time after the last dose of Compound 1 CCR3 antagonist had been administered. Arrows report when an anti-VEGF agent was administered intravitreally (IVT). As with the preceding figures, status of subretinal fluid, intraretinal fluid and choroidal neovascularization (CNV) are also noted over time.
Figure 12:
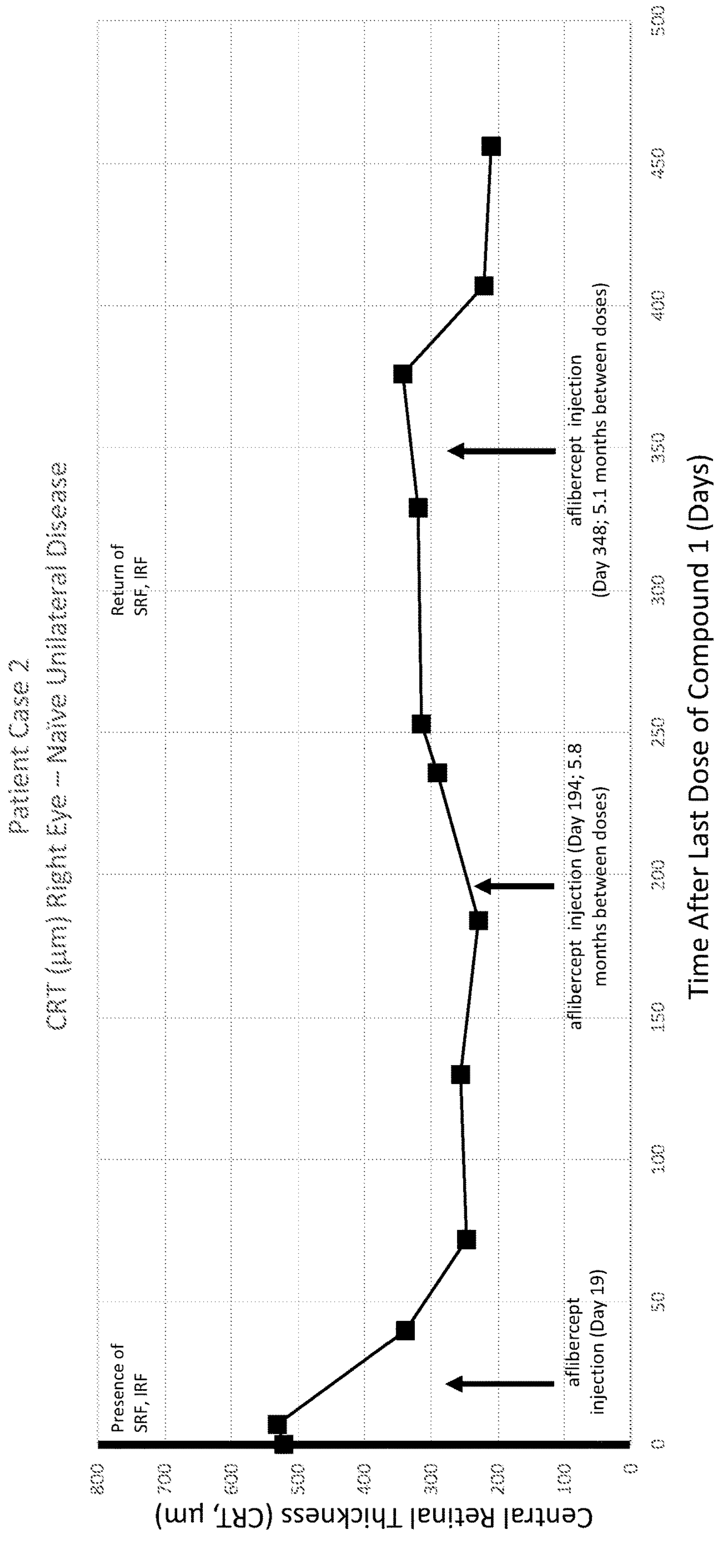
Figure 13:
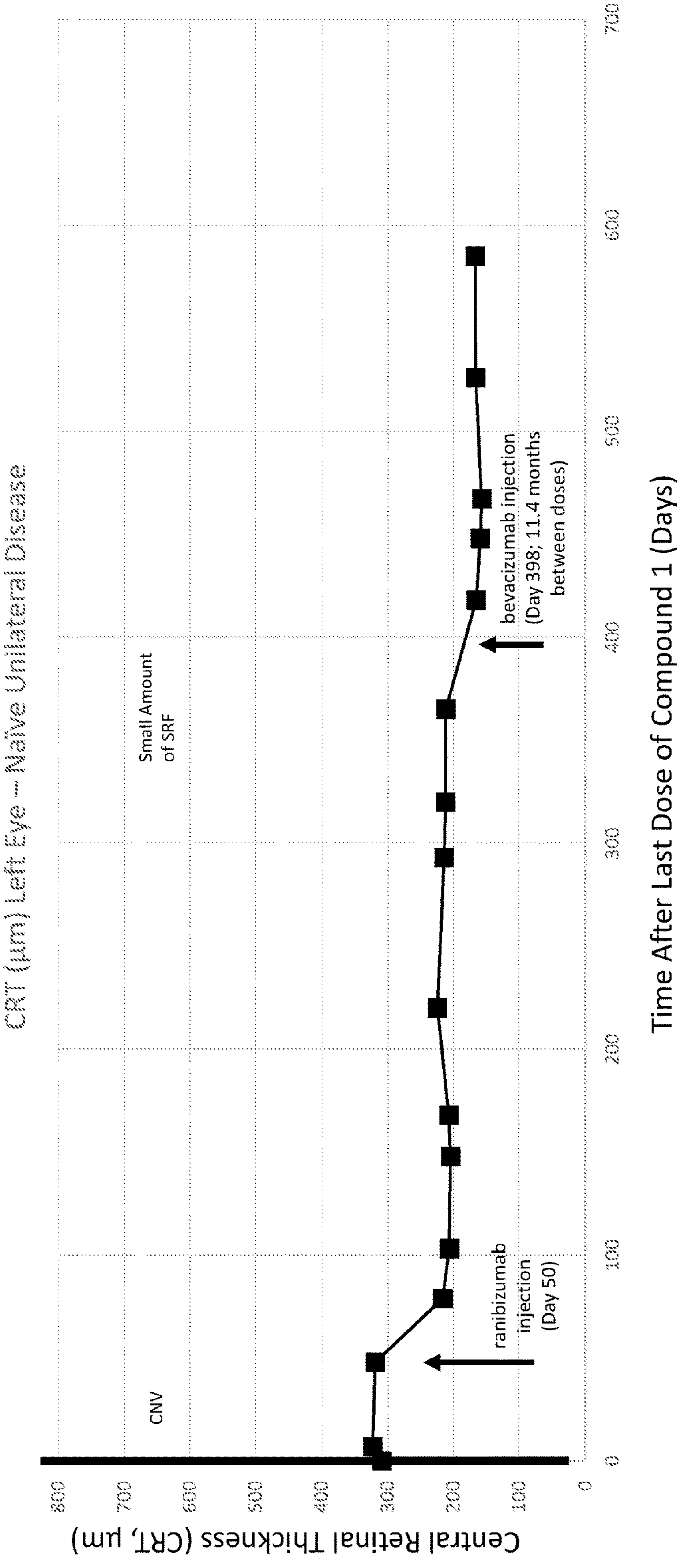

Despite clear data highlighting the value of standardized dosing or frequency of dosing, the results described in FIGS. 4-5, 9-10, 14-15, 19-21 and Tables D and H were completely unexpected and surprising. The dose amounts for anti-VEGF agents used in these examples were unchanged, but resolution of SRF, IRF, and CNV was more pronounced. More surprisingly refractory eyes required a significantly decreased frequency of IVT anti-VEGF administrations (e.g., 0.69 to 1.37 doses required per year compared to a standard medium of 7.3 across all eyes, and a likely higher frequency of dosing per year in practice of these non-responsive patients. (See FIGS. 21 and 22 and the retrospective analysis of Jang L et al., Graefes Arch Clin Exp Ophthalmol, 253(8):1211-16 (2015), see also Fowler S C and Schneider E W, More frequent dosing for refractory nAMD?, Retina Specialist, May 13, 2020). Further, resensitization of refractory eyes was achieved to an unexpected degree. For example, the numbers of ETDRS letters read improved and stabilized (FIGS. 9-10 and Table D). This was unexpected as well as refractory patients tend not to show improvement with the standard of care, rather they typically require monthly (or more frequent) injection merely to maintain their visual or anatomic status, plus these particular subjects were already severely impaired.

Figure 14:
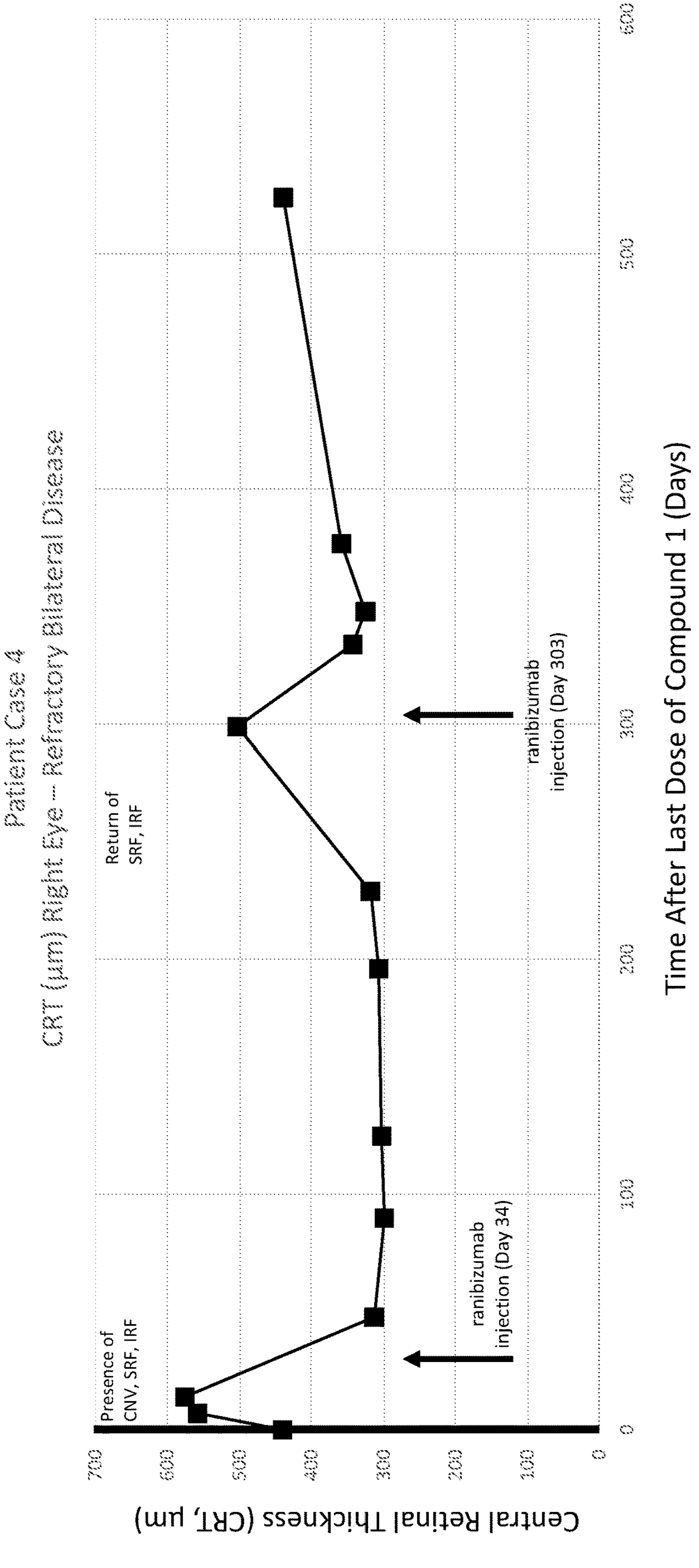
FIG. 14 and FIG. 15 report central retinal thickness in the subject with refractory, bilateral wAMD. The x-axis depicts time after the last dose of Compound 1 had been administered. Arrows report when an anti-VEGF agent was administered intravitreally (IVT). The status of subretinal fluid, intraretinal fluid and choroidal neovascularization (CNV) are also noted over time.
Figure 15:
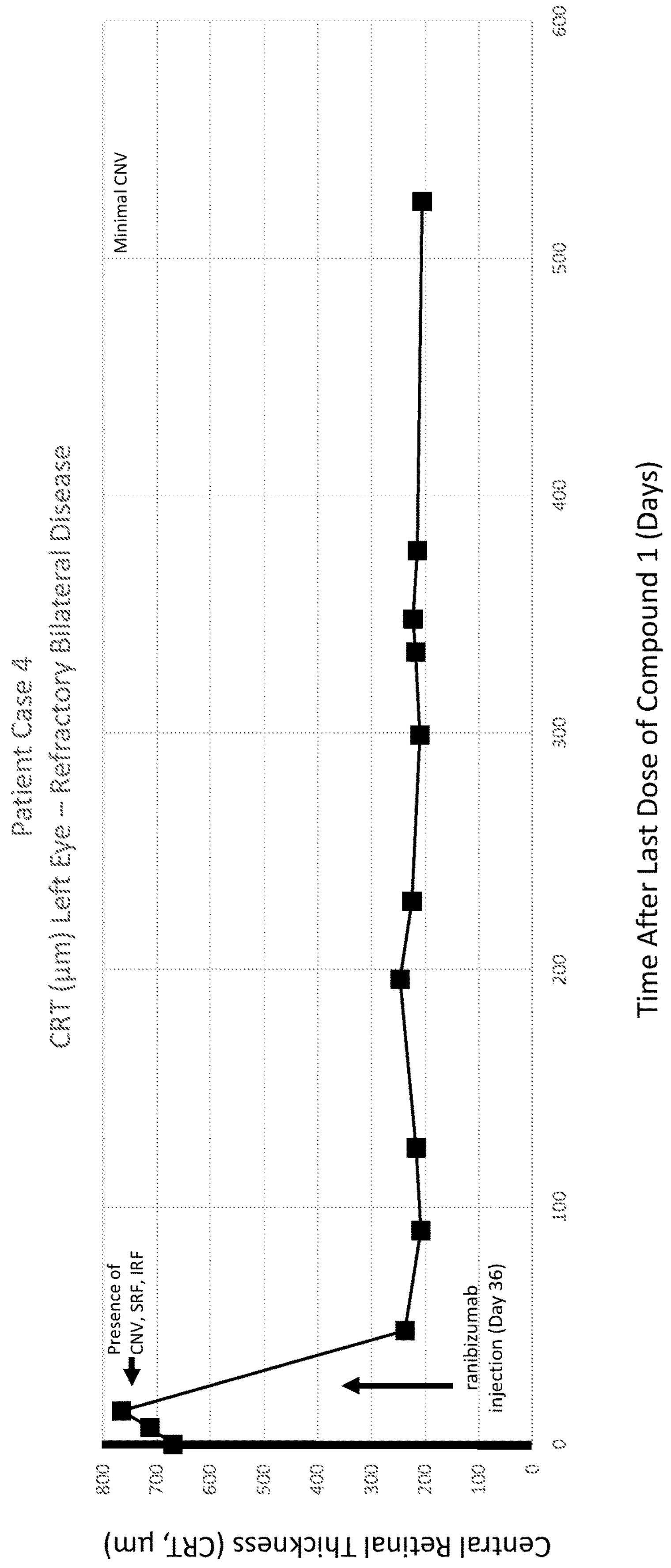
Figure 16:
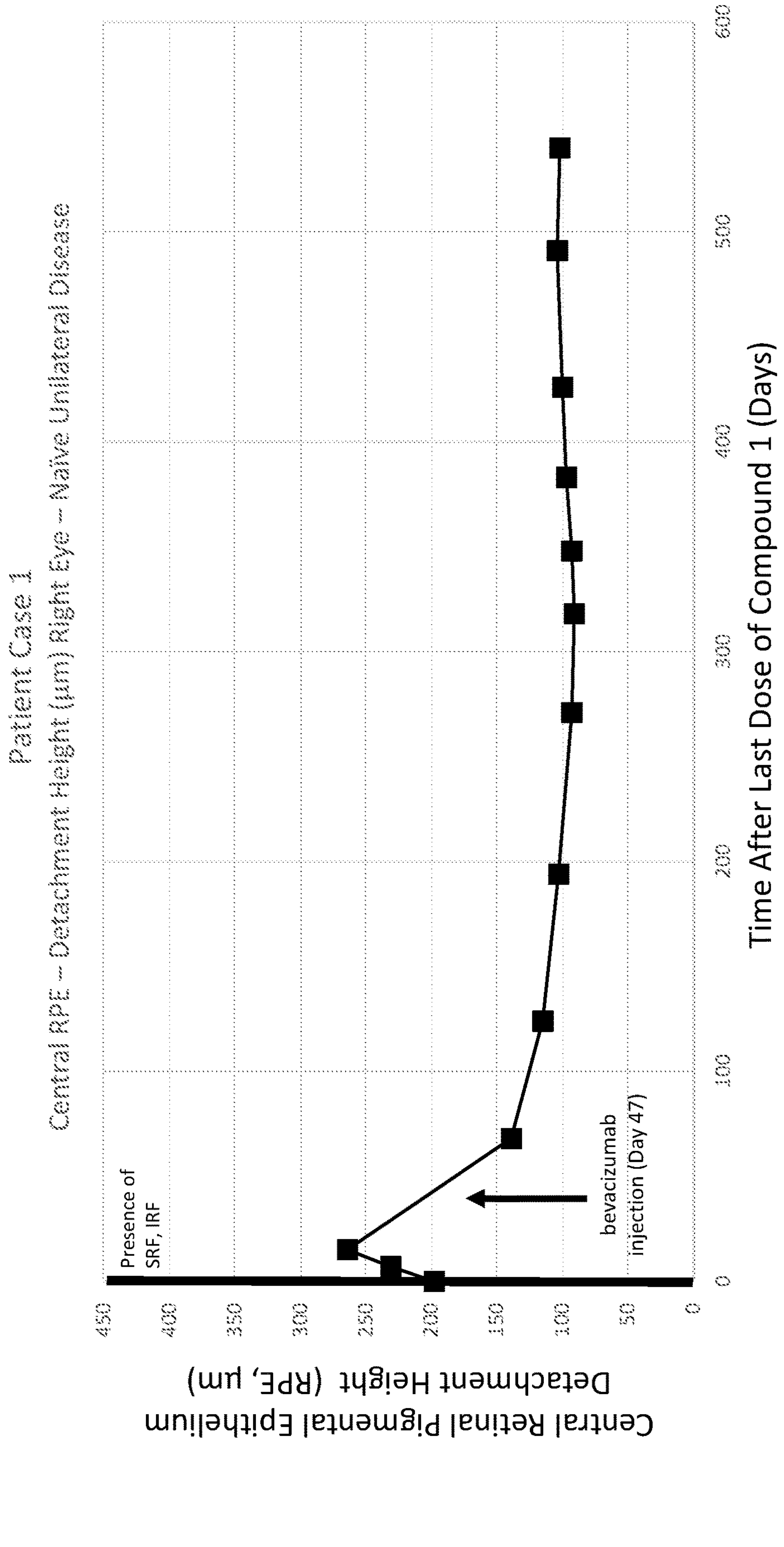
FIG. 16, FIG. 17 and FIG. 18 report central retinal pigmental epithelium (RPE) detachment height in the three subjects with naïve unilateral wAMD. The x-axis depicts time after the last dose of Compound 1 CCR3 antagonist had been administered. Arrows report when an anti-VEGF agent was administered intravitreally (IVT). As with the preceding figures, status of subretinal fluid, intraretinal fluid and choroidal neovascularization (CNV) are also noted over time.
Figure 17:
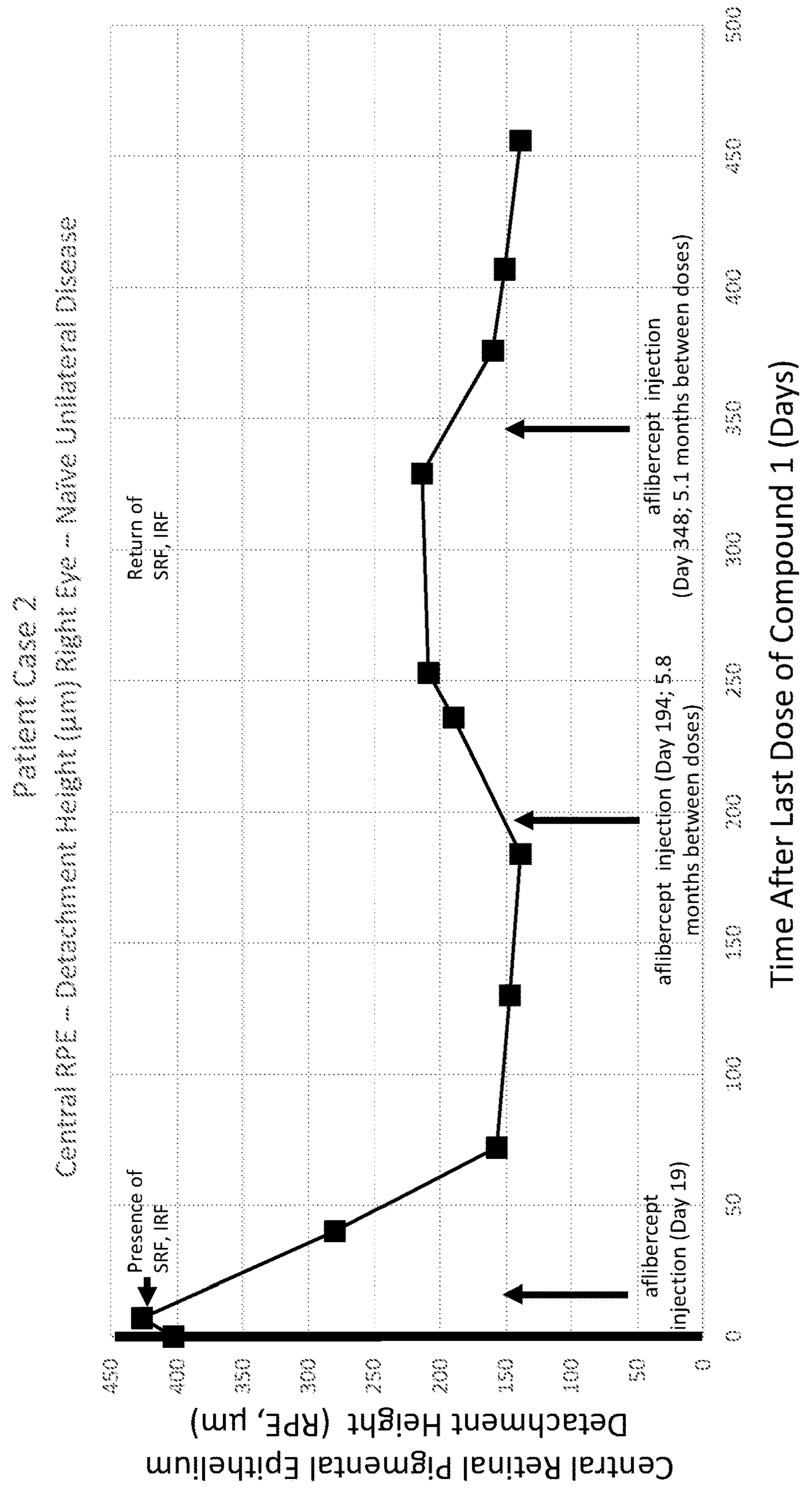
Figure 18:
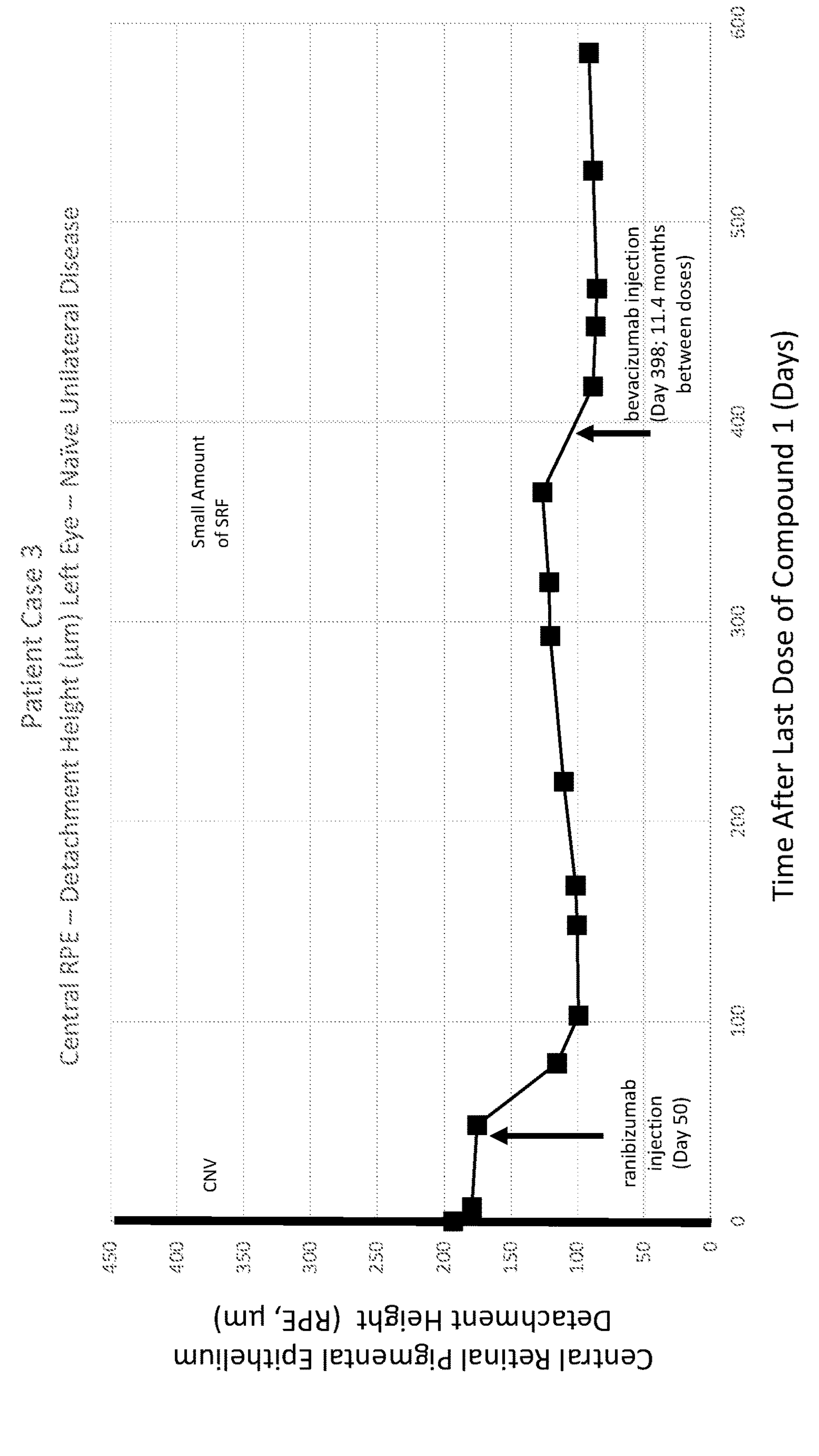
Figure 19:
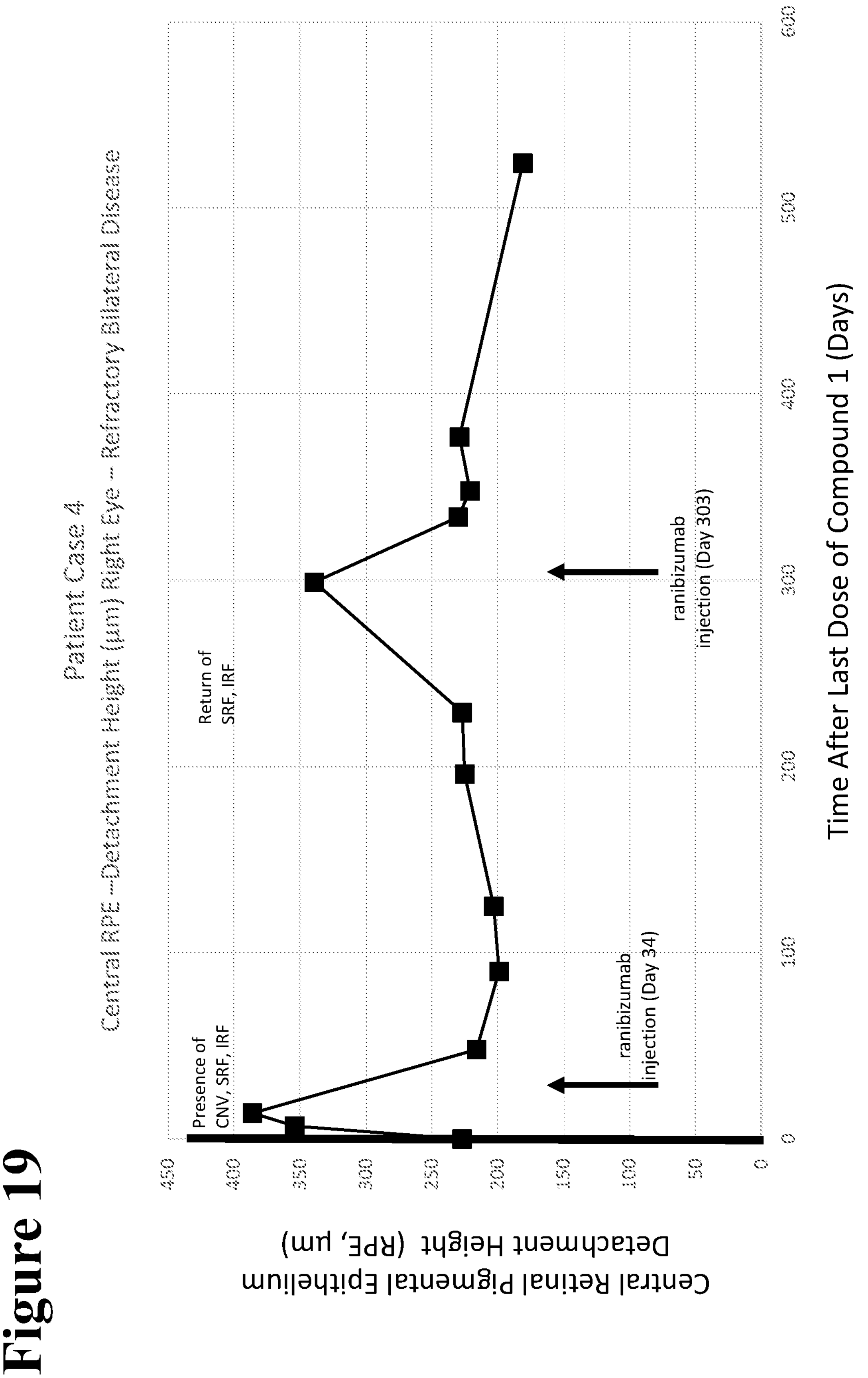
FIG. 19 and FIG. 20 report central retinal pigmental epithelium (RPE) detachment height in the subject with refractory, bilateral wAMD. The x-axis depicts time after the last dose of Compound 1 CCR3 antagonist had been administered. Arrows report when an anti-VEGF agent was administered intravitreally (IVT). As with the preceding figures, status of subretinal fluid, intraretinal fluid and choroidal neovascularization (CNV) are also noted over time.
Figure 20:
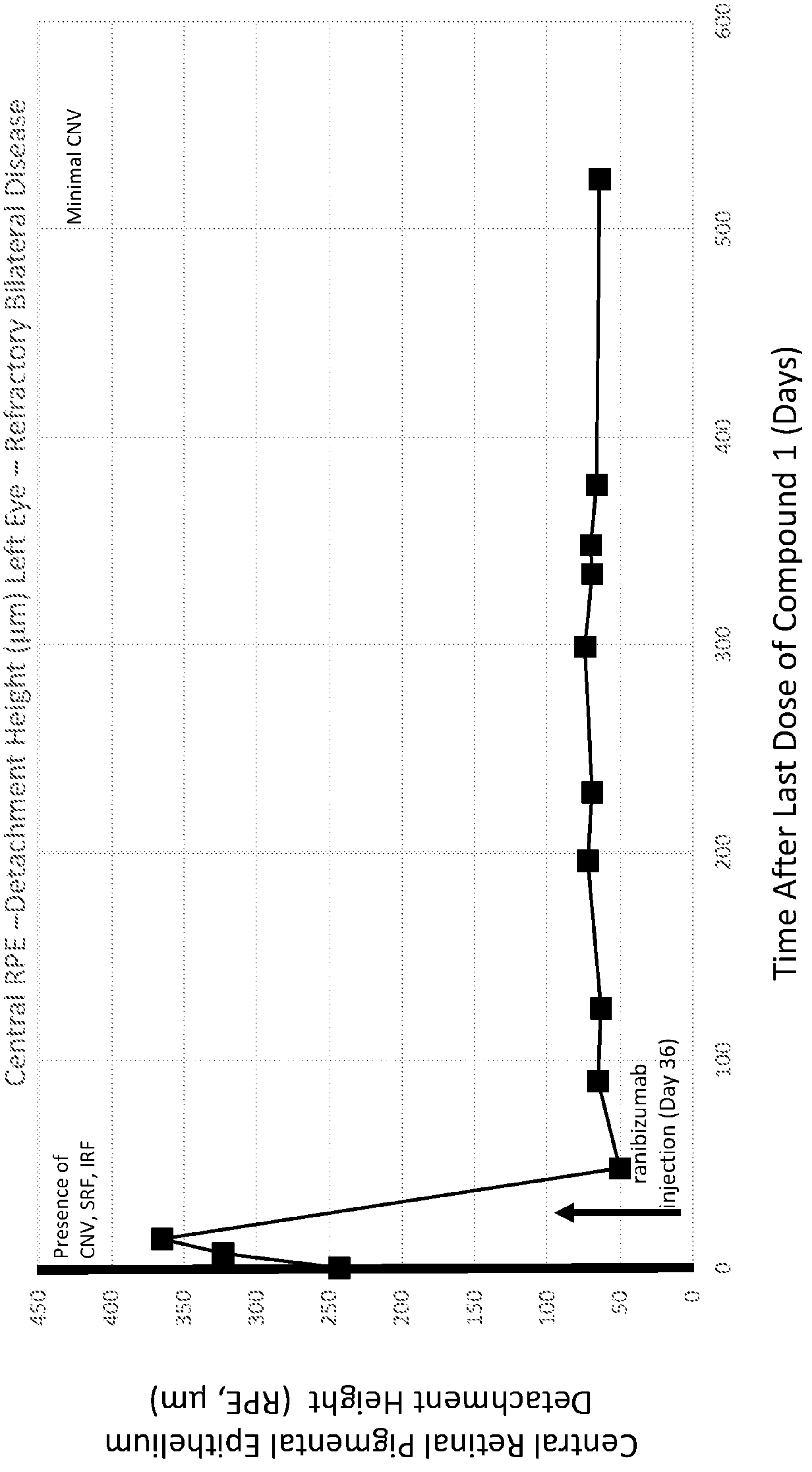
Figure 21:
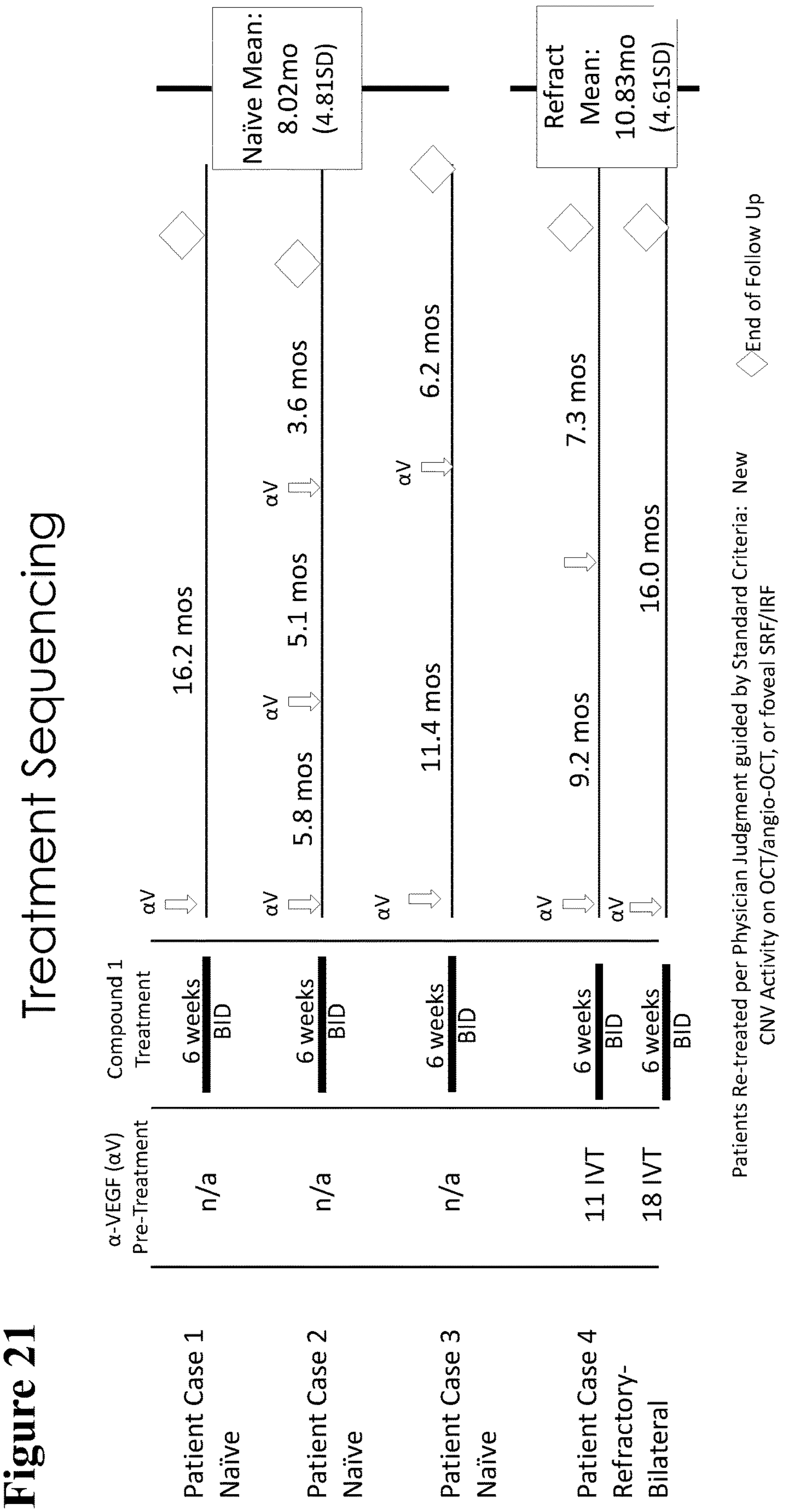
FIG. 21 is a chart depicting the sequencing of treatment for each subject. Patient Cases 1 through 3 (naïve unilateral subjects) received oral Compound 1 twice per day (BID) for 6 weeks prior to anti-VEGF IVT injections. The time between doses of anti-VEGF agents is shown in months ("mo" or "mos"). The mean months between doses of anti-VEGF agents is reported in the box labeled "Naïve Mean" with standard deviations (SD) shown in parentheses.

The CRT stabilized and become responsive once again to anti-VEGF IVT injections (FIGS. 14-15 and Table D). Central retinal pigmental epithelium detachment height was also reduced and could be maintained with infrequent anti-VEGF IVT injections (FIGS. 19-21 and Table D). Additionally, fluid exudation as determined by the presence of IRF and SRF as well as presence of CNV were once again responsive and successfully managed by anti-VEGF IVT administration even with a significantly reduced frequency of dosing (Table H). The combination of a regimen of Compound 1 CCR3/Eotaxin-1 pathway antagonist followed by IVT anti-VEGF appeared to be complimentary and function in a synergistic manner. It is unusually surprising that a selective anti-inflammatory agent administered prior to anti-VEGF injection produced a significantly more pronounced and durable effect.

ii. Naïve Subject Eyes

Newly diagnosed subjects with choroidal neovascularization (CNV) secondary to wAMD were administered 400 mg of Compound 1 CCR antagonist orally twice per day (BID) for a total dose of 800 mg per day. The clinical trial treatment regimen included 6 weeks of Compound 1 followed by 4 weeks of safety follow up (weeks 7 and 8 as in office visits and follow up by phone at week 10) with no additional Compound 1 treatment. Subject treatment visits took place once per week where mean changes in BCVA as measured by ETDRS were noted, slit lamp and SD-OCT performed, and intraocular pressure taken. Subjects then returned to routine treatment with their physician post clinical trial and were treated or re-treated with α-VEGF agents per physician judgment guided by standard criteria such as new CNV activity on OCT/angio-OCT (aOCT) or increased foveal subretinal fluid (SRF)/intra-retinal fluid (IRF). Different α-VEGF agents (described in FIGS. 1-3, 6-8, 11-13, and 16-18, 21 and Tables A-C and E-G) were administered by intra-vitreal injection. For aflibercept, 2 mg in 0.05 mL was given per single intravitreal injection. For bevacizumab, 1.25 mg in 0.05 mL was given per single intravitreal injection. For ranibizumab, 0.5 mg in 0.05 mL was given per single intravitreal injection.

All OCT tests were performed using REVO NX (Optopol Technology, Poland). A 3-dimensional (3D) scanning protocol covering a 7×7 mm area was used (1024 A-scans×64 tomograms). The central retinal thickness (CRT) was measured automatically (software version 9.6). The detection of the fovea and the accuracy of layers segmentation was checked by the operator. If necessary, the fovea location and the outer retinal boundaries were corrected manually by moving the pointer to the desired position. In such cases, the central macular thickness value was recalculated. Subretinal and intraretinal fluid presence was assessed manually. SRF was defined as a hyporeflective space between retinal pigment epithelium and the sensory retina, whereas IRF as ovoid or round spaces within the retina, with a low reflectivity content. SRF and IRF was distinguished from the outer retinal tubulations (ORTs) and degenerative IRF. The latter were not recognized as a CNV activity sign. CNV activity signs such as neovascular vasculature seen on OCT angiography were monitored. Additionally, lipid exudates and enlargement of RPE elevation were noted.

In real-world studies, the average number of injections per patient per year in initial anti-VEGF IVT therapy is 7.3 for bevacizumab, aflibercept, and ranibizumab, or per-label would be 12 injections for bevacizumab or ranibizumab. (Ciulla T A et al., Ophthalmology Retina, 4:19-30 (2020)). In comparison, the combination of Compound 1 CCR3/Eotaxin-1 pathway antagonist and subsequent anti-VEGF IVT treatment produced a markedly lower average number of injections, independent of the identity of the agent (i.e., aflibercept, bevacizumab, or ranibizumab). Patient Case 1, treated with bevacizumab required an average of less than one dose per year (0.667) (See FIGS. 1, 6, 11, 16, and 22 plus Tables A and E). Patient Case 2, treated with aflibercept required an average of at most, less than 3 doses per year (2.36). (See FIGS. 2, 7, 12, 17, and 22 plus Tables B and F). Patient Case 3 treated once with ranibizumab and subsequently with bevacizumab required an average of approximately 1 dose per year (1.23). (See FIGS. 3, 8, 13, 18, and 22 plus Tables C and G).

The required frequency of IVT anti-VEGF injections is dramatically reduced in these naïve patients, compared to retrospective analysis. (Ciulla, supra). In another retrospective study, even when the timing of IVT anti-VEGF injection was to a PRN dosing regimen (pro re nata, PRN, or "as needed" dosing), dosing averages ranged from 4.9 to 8 doses per year (Wykof C C et al., JMCP, 24(2-a):S3-S15 (2018)). Thus, the effect of this combination of the CCR3/Eotaxin-1 pathway antagonist (Compound 1) and various anti-VEGF agents was to unexpectedly reduce the recommended frequency of anti-VEGF IVT injections to a dramatic degree. Such a drop in the frequency of IVT injections will result in significantly less cost, physician visits, and unpleasant and invasive procedures for patients.

In retrospective analyses where anti-VEGF agents are administered less frequently, CRT, intraretinal and subretinal fluid occurrence as well as pigment epithelial detachment tend to produce a sawtooth curve over time. That is, a semi-regular pattern of peaks and troughs as opposed to a smoother curve produced in populations receiving more frequent dosing. (See, Waldstein S M et al., Ophthalmology 123:1521-29 (2016) and Jaffe G J, et al., Ophthalmology, 123:1856-64 (2016)). Unexpectedly, the naïve patients from Patient Cases 1 through 3 all experienced a relatively flattened visual and anatomic pattern in comparison to the commonly observed semi-regular sawtooth patterns of standard of care anti-VEGF treatment in these measures despite a significantly greater reduction in frequency of anti-VEGF IVT treatment.

iii. Tables

TABLE A

| Patient Case 1<br>Naïve Unilateral Disease | | | | | |
|---|---|---|---|---|---|
| Days After Last Dose of Compound 1 | Drug Treatment | Snellen Ratio (Right Eye) | ETDRS Letters Read (Right Eye) | Central Retinal Thickness (CRT; μm) (Right Eye) | Central Retinal Pigmental Epithelium (RPE; μm) (Right Eye) |
| −44 | Compound 1 | 0.125 | 40 | 374 | 148 |
| −41 | Compound 1 | 0.125 | 40 | 349 | 150 |
| −35 | Compound 1 | 0.125 | 40 | 329 | 143 |
| −28 | Compound 1 | 0.2 | 50 | 323 | 140 |
| −21 | Compound 1 | 0.125 | 40 | 360 | 153 |
| −14 | Compound 1 | 0.1 | 35 | 375 | 174 |
| −8 | Compound 1 | 0.1 | 35 | 401 | 189 |
| 0 | Compound 1 | 0.08 | 30 | 382 | 198 |
| 7 | | 0.0625 | 25 | 434 | 231 |
| 15 | | 0.08 | 30 | 453 | 264 |
| 47 | bevacizumab (right eye) | | | | |
| 68 | | 0.2 | 50 | 332 | 139 |
| 124 | | 0.16 | 45 | 328 | 115 |
| 194 | | 0.16 | 45 | 285 | 103 |
| 271 | | 0.16 | 45 | 322 | 93 |
| 318 | | 0.16 | 45 | 313 | 91 |
| 348 | | 0.2 | 50 | 296 | 93 |
| 383 | | 0.2 | 50 | 289 | 97 |
| 426 | | 0.25 | 55 | 285 | 100 |
| 491 | | 0.2 | 50 | 290 | 104 |
| 540 | | 0.2 | 50 | 286 | 102 |

TABLE B

| Patient Case 2<br>Naïve Unilateral Disease | | | | | |
|---|---|---|---|---|---|
| Days After Last Dose of Compound 1 | Drug Treatment | Snellen Ratio (Right Eye) | ETDRS Letters Read (Right Eye) | Central Retinal Thickness (CRT; μm) (Right Eye) | Central Retinal Pigmental Epithelium Detachment Height (RPE; μm) (Right Eye) |
| −42 | Compound 1 | 0.200 | 50 | 517 | 413 |
| −35 | Compound 1 | 0.160 | 45 | 489 | 400 |
| −28 | Compound 1 | 0.160 | 45 | 509 | 395 |
| −21 | Compound 1 | 0.200 | 50 | 501 | 397 |
| −14 | Compound 1 | 0.200 | 50 | 520 | 409 |
| −7 | Compound 1 | 0.200 | 50 | 530 | 425 |
| 0 | Compound 1 | 0.160 | 45 | 521 | 403 |
| 7 | | 0.160 | 45 | 531 | 427 |
| 19 | aflibercept (right eye) | | | | |
| 40 | | 0.320 | 50 | 339 | 280 |
| 72 | | 0.250 | 55 | 247 | 157 |
| 130 | | 0.317 | 60 | 256 | 147 |
| 184 | | 0.317 | 60 | 229 | 139 |
| 194 | aflibercept (right eye) | | | | |
| 236 | | 0.200 | 50 | 291 | 190 |
| 253 | | 0.200 | 50 | 315 | 209 |
| 329 | | 0.160 | 45 | 320 | 214 |
| 348 | aflibercept (right eye) | | | | |
| 376 | | 0.200 | 50 | 343 | 160 |
| 407 | | 0.200 | 50 | 221 | 151 |
| 456 | | 0.250 | 55 | 210 | 139 |

TABLE C

Patient Case 3
Naïve Unilateral Disease

| Days After Last Dose of Compound 1 | Drug Treatment | Snellen Ratio (Left Eye) | ETDRS Letters Read (Left Eye | Central Retinal Thickness (CRT; µm) (Left Eye) | Central Retinal Pigmental Epithelium Detachment Height (RPE; µm) (Left Eye) |
|---|---|---|---|---|---|
| −41 | Compound 1 | 0.080 | 30 | 398 | 210 |
| −35 | Compound 1 | 0.080 | 30 | 392 | 208 |
| −28 | Compound 1 | 0.050 | 20 | 357 | 194 |
| −20 | Compound 1 | 0.063 | 25 | 450 | 267 |
| −13 | Compound 1 | 0.087 | 25 | 353 | 235 |
| −6 | Compound 1 | 0.080 | 30 | 315 | 192 |
| 0 | Compound 1 | 0.063 | 25 | 309 | 193 |
| 7 | | 0.100 | 35 | 323 | 179 |
| 48 | | 0.100 | 35 | 319 | 175 |
| 50 | ranibizumab (left eye) | | | | |
| 79 | | 0.125 | 40 | 216 | 115 |
| 103 | | 0.160 | 45 | 206 | 99 |
| 148 | | 0.160 | 45 | 204 | 100 |
| 168 | | 0.160 | 45 | 207 | 101 |
| 220 | | 0.125 | 40 | 224 | 110 |
| 293 | | 0.125 | 40 | 214 | 120 |
| 320 | | 0.125 | 40 | 212 | 121 |
| 365 | | 0.125 | 40 | 211 | 126 |
| 398 | bevacizumab (left eye) | | | | |
| 418 | | 0.125 | 40 | 165 | 88 |
| 448 | | 0.125 | 40 | 159 | 86 |
| 467 | | 0.125 | 40 | 157 | 85 |
| 526 | | 0.125 | 40 | 166 | 88 |
| 585 | | 0.160 | 45 | 167 | 91 |

TABLE D

Patient Case 4
Refractory Bilateral Disease

| Days After Last Dose of Compound 1 | Drug Treatment* | Snellen Ratio (Right Eye) | Snellen Ratio (Left Eye) | ETDRS Letters Read (Right Eye) | ETDRS Letters Read (Left Eye) | Central Retinal Thickness (CRT; µm) (Right Eye) | Central Retinal Thickness (CRT; µm) (Left Eye) | Central Retinal Pigmental Epithelium (RPE; µm) (Right Eye) | Central Retinal Pigmental Epithelium Detachment Height (RPE; µm) (Left Eye) |
|---|---|---|---|---|---|---|---|---|---|
| −49 | | 0.160 | 0.200 | 45 | 50 | 471 | 655 | 253 | 291 |
| −42 | Compd 1 | 0.125 | 0.250 | 40 | 55 | 598 | 715 | 355 | 347 |
| −34 | Compd 1 | 0.160 | 0.200 | 45 | 50 | 445 | 694 | 231 | 277 |
| −28 | Compd 1 | 0.160 | 0.250 | 45 | 55 | 446 | 677 | 226 | 291 |
| −22 | Compd 1 | 0.125 | 0.250 | 40 | 55 | 407 | 672 | 203 | 299 |
| −14 | Compd 1 | 0.125 | 0.250 | 40 | 55 | 426 | 665 | 205 | 275 |
| −7 | Compd 1 | 0.160 | 0.200 | 45 | 50 | 395 | 663 | 207 | 253 |
| 0 | Compd 1 | 0.160 | 0.200 | 45 | 50 | 440 | 670 | 227 | 243 |
| 7 | | 0.200 | 0.160 | 50 | 45 | 558 | 713 | 354 | 323 |
| 1 | | 0.125 | 0.160 | 40 | 45 | 576 | 766 | 386 | 365 |
| 34 | ranibizumab (right eye) | | | | | | | | |
| 36 | ranibizumab (left eye) | | | | | | | | |
| 48 | | 0.250 | 0.400 | 55 | 65 | 313 | 238 | 216 | 50 |
| 90 | | 0.250 | 0.400 | 55 | 65 | 299 | 208 | 199 | 65 |
| 125 | | 0.200 | 0.317 | 50 | 60 | 303 | 217 | 203 | 63 |
| 196 | | 0.250 | 0.317 | 55 | 60 | 307 | 247 | 225 | 72 |
| 229 | | 0.250 | 0.317 | 55 | 60 | 318 | 225 | 227 | 69 |
| 299 | | 0.125 | 0.400 | 40 | 65 | 503 | 210 | 339 | 74 |
| 303 | ranibizumab | | | | | | | | |

TABLE D-continued

| Patient Case 4 Refractory Bilateral Disease | | | | | | | | | | |
|---|---|---|---|---|---|---|---|---|---|---|
| Days After Last Dose of Compound 1 | Drug Treatment* | Snellen Ratio (Right Eye) | Snellen Ratio (Left Eye) | ETDRS Letters Read (Right Eye) | ETDRS Letters Read (Left Eye) | Central Retinal Thickness (CRT; μm) (Right Eye) | Central Retinal Thickness (CRT; μm) (Left Eye) | Central Retinal Pigmental Epithelium (RPE; μm) (Right Eye) | Central Retinal Pigmental Epithelium Detachment Height (RPE; μm) (Left Eye) |
| | (right eye) | | | | | | | | |
| 334 | | 0.250 | 0.317 | 55 | 60 | 342 | 218 | 230 | 69 |
| 348 | | 0.250 | 0.317 | 55 | 60 | 325 | 223 | 221 | 70 |
| 377 | | 0.250 | 0.400 | 50 | 65 | 358 | 215 | 229 | 66 |
| 524 | | 0.200 | 0.317 | 50 | 60 | 439 | 206 | 181 | 64 |

*Prior to treatment with Compound 1 (Compd 1), the subject's right eye had received 11 injections of ranibizumab, and the left eye received 18 injections of ranibizumab.

TABLE E

Patient Case 1
Naïve Unilateral Disease
Presence of Sub-retinal fluid (SRF), Intraretinal Fluid (IRF), or Choroidal Neovascularization (CNV)

| Days After Last Dose of Compound 1 | Drug Treatment* | Presence of SRF or IRF (Right Eye) | Presence of Other CNV Activity (Right Eye) | Atrophy/Fibrosis Noted (Right Eye) |
|---|---|---|---|---|
| −44 | Compound 1 | SRF | | Some atrophy and fibrosis |
| −41 | Compound 1 | | | |
| −35 | Compound 1 | | | |
| −28 | Compound 1 | slightly less SRF | | |
| −21 | Compound 1 | | | |
| −14 | Compound 1 | | | |
| −8 | Compound 1 | | | |
| 0 | Compound 1 | less SRF | | |
| 7 | | no SRF | | |
| 15 | | Extra-foveal SRF only, IRF | | |
| 47 | bevacizumab (right eye) | | | |
| 68 | | | | |
| 124 | | | | |
| 194 | | | | |
| 271 | | | | |
| 318 | | | | |
| 348 | | | | |
| 383 | | | | |
| 426 | | | | |
| 491 | | | | |
| 540 | | | | |

*Angio-OCT performed these visits only, remainder ETDRS, OCT, Clinical Exam only

TABLE F

Patient Case 2
Naïve Unilateral Disease
Presence of Sub-retinal fluid (SRF), Intraretinal Fluid (IRF), or Choroidal Neovascularization (CNV)

| Days After Last Dose of Compound 1 | Drug Treatment | Presence of SRF or IRF (Right Eye) | Presence of Other CNV Activity (Right Eye) | Atrophy/Fibrosis Noted (Right Eye) |
|---|---|---|---|---|
| −42 | Compound 1 | SRF, extensive IRF | | |
| −35 | Compound 1 | | | |
| −28 | Compound 1 | | | |
| −21 | Compound 1 | | | |
| −14 | Compound 1 | | | |
| −7 | Compound 1 | | | |
| 0 | Compound 1 | | | |
| 7 | | SRF, IRF | | |
| 19 | aflibercept (right eye) | | | |
| 40 | | no SRF, few small IRF, scaring in the fovea | | Scarring in the fovea |
| 72 | | no SRF, no IRF, smaller scaring in the fovea | | Smaller scarring in the fovea |
| 130 | | no SRF, no IRF | | |
| 184* | | no SRF, no IRF | CNV vessels visible in angio-OCT, no activity in OCT | |
| 194 | aflibercept (right eye) | | | |
| 236* | | few cysts of IRF, shallow extra-foveal SRF | small CNV vessels visible in angio-OCT - no injection (patient did not want to have injection | |
| 253* | | more cysts of IRF, SRF | small CNV vessels visible in angio-OCT - no injection | |
| 329* | | IRF, SRF | small CNV vessels visible in angio-OCT - no injection | |
| 348 | aflibercept (right eye) | | | |
| 376 | | no SRF, no IRF | | |
| 407 | | no SRF, few extra-foveal IRF cysts | | |
| 456 | | no SRF, few cysts of IRF outside the fovea | | |

*Angio-OCT performed these visits only, remainder ETDRS, OCT, Clinical Exam only

TABLE G

Patient Case 3
Naïve Unilateral Disease
Presence of Sub-retinal fluid (SRF), Intraretinal Fluid (IRF), or Choroidal Neovascularization (CNV)

| Days After Last Dose of Compound 1 | Drug Treatment | Presence of SRF or IRF (Left Eye) | Presence of Other CNV Activity (Left Eye) | Atrophy/Fibrosis Noted (Left Eye) |
|---|---|---|---|---|
| −41 | Compound 1 | SRF, IRF | | |
| −35 | Compound 1 | SRF, IRF | | |
| −28 | Compound 1 | SRF, IRF | | |

TABLE G-continued

Patient Case 3
Naïve Unilateral Disease
Presence of Sub-retinal fluid (SRF), Intraretinal Fluid (IRF), or Choroidal Neovascularization (CNV)

| Days After Last Dose of Compound 1 | Drug Treatment | Presence of SRF or IRF (Left Eye) | Presence of Other CNV Activity (Left Eye) | Atrophy/Fibrosis Noted (Left Eye) |
|---|---|---|---|---|
| −20 | Compound 1 | SRF, IRF | | |
| −13 | Compound 1 | no IRF, less SRF | | |
| −6 | Compound 1 | no IRF, less SRF | | |
| 0 | Compound 1 | no SRF, two small cysts of IRF | | |
| 7 | | no SRF, less IRF | | |
| 48* | | no SRF, less IRF | CNV vessels visible in angio-OCT, no new activity in OCT | |
| 50 | ranibizumab (left eye) | | | |
| 79 | | no SRF, no IRF | | |
| 103 | | no SRF, no IRF | | |
| 148 | | no SRF, no IRF | | |
| 168* | | no SRF, no IRF | only few larger CNV vessels (with fibrosis) | only few larger CNV vessels (with fibrosis) |
| 220 | | no SRF, no IRF | | |
| 293 | | no SRF, no IRF | | |
| 320 | | no SRF, no IRF | | |
| 365 | | very small amount of SRF outside the fovea, no IRF | | |
| 398 | bevacizumab (left eye) | | | |
| 418 | | no SRF, no IRF | | |
| 448 | | no SRF, no IRF | | |
| 467 | | no SRF, no IRF | | |
| 526 | | no SRF, no IRF | | |
| 585 | | no SRF, no IRF | | |

TABLE H

Patient Case 4
Refractory Bilateral Disease
Presence of Sub-retinal fluid (SRF), Intraretinal Fluid (IRF), or Choroidal Neovascularization (CNV)

| Days After Last Dose of Compound 1 | Drug Treatment * | Presence of SRF or IRF (Right Eye) | Presence of SRF or IRF (Left Eye) | Presence of Other CNV Activity (Right Eye) | Presence of Other CNV Activity (Left Eye) | Atrophy/ Fibrosis (Right Eye) | Atrophy/ Fibrosis (Left Eye) |
|---|---|---|---|---|---|---|---|
| −49 | | large amount of SRF, IRF | SRF, Large foveal IRF space | | | | |
| −42 | Compound 1 | large amount of SRF, IRF | SRF, Large foveal IRF space | | | | |
| −34 | Compound 1 | SRF, IRF | SRF, Large foveal IRF space | | | | |
| −28 | Compound 1 | SRF, IRF | | | | | |

TABLE H-continued

Patient Case 4
Refractory Bilateral Disease
Presence of Sub-retinal fluid (SRF), Intraretinal Fluid (IRF), or Choroidal Neovascularization (CNV)

| Days After Last Dose of Compound 1 | Drug Treatment * | Presence of SRF or IRF (Right Eye) | Presence of SRF or IRF (Left Eye) | Presence of Other CNV Activity (Right Eye) | Presence of Other CNV Activity (Left Eye) | Atrophy/ Fibrosis (Right Eye) | Atrophy/ Fibrosis (Left Eye) |
|---|---|---|---|---|---|---|---|
| −22 | Compound 1 | SRF, IRF | | | | | |
| −14 | Compound 1 | SRF, IRF | Decreased Foveal IRF | | | | |
| −7* | Compound 1 | SRF, IRF | | CNV vessels in angio-OCT | CNV vessels in angio-OCT | | |
| 0 | Compound 1 | SRF, IRF | Decreased Foveal IRF | | | | |
| 7 | | SRF, IRF | SRF, IRF | | | | Large Atrophic IRF |
| 14 | | SRF, IRF | SRF, IRF | | | | Large Atrophic IRF |
| 34 | ranibizumab (right eye) | | | | | | |
| 36 | ranibizumab (left eye) | | | | | | |
| 48 | | no SRF, no IRF | no SRF, no IRF | no activity in OCT | no activity in OCT | | |
| 90* | | no SRF, no IRF | no SRF, no IRF, single central atrophic space | small CNV vessels in angio-OCT, no activity in OCT | no activity in angio-OCT | | Single central atrophic space |
| 125 | | no SRF, no IRF | no SRF, no IRF, single central atrophic space | | | | Single central atrophic space |
| 196 | | no SRF, no IRF | no SRF, no IRF, single central atrophic space | | | | Single central atrophic space |
| 229 | | no SRF, no IRF | no SRF, no IRF, single central atrophic space | | | | Single central atrophic space |
| 299 | | SRF, IRF | no SRF, no IRF, single central atrophic space | | | | Single central atrophic space |

TABLE H-continued

Patient Case 4
Refractory Bilateral Disease
Presence of Sub-retinal fluid (SRF), Intraretinal Fluid (IRF), or Choroidal Neovascularization (CNV)

| Days After Last Dose of Compound 1 | Drug Treatment * | Presence of SRF or IRF (Right Eye) | Presence of SRF or IRF (Left Eye) | Presence of Other CNV Activity (Right Eye) | Presence of Other CNV Activity (Left Eye) | Atrophy/ Fibrosis (Right Eye) | Atrophy/ Fibrosis (Left Eye) |
|---|---|---|---|---|---|---|---|
| 303 | ranibizumab (right eye) | | | | | | |
| 334 | | no SRF, no IRF | no SRF, no IRF, single central atrophic space | | | | Single central atrophic space |
| 348 | | | no SRF, no IRF, single central atrophic space | | | | Single central atrophic space |
| 377 | | | no SRF, no IRF, single central atrophic space | | | | Single central atrophic space |
| 524 | | no SRF, IRF | no SRF, small IRF, single central atrophic space | | minimal activity of CNV | | |

* Angio-OCT performed these visits only, remainder ETDRS, OCT, Clinical Exam only

What is claimed:

1. A method of reducing the frequency of administration of an anti-VEGF agent to a subject diagnosed with wet age-related macular degeneration, the method comprising: administering a CCR3 inhibitory agent to the subject; administering the anti-VEGF agent to the subject after the administering of the CCR3 inhibitory agent; and administering additional subsequent doses of the anti-VEGF agent to the subject at a frequency less than the recommended frequency, wherein the subject is refractory to the anti-VEGF agent; wherein the CCR3 inhibitory agent is represented by the compound 1, (Compound 1)

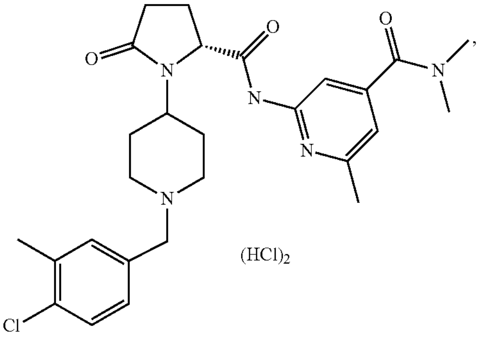

administered orally, wherein the anti-VEGF is selected from the group consisting of aflibercept, ranibizumab, and bevacizumab, and is administered intravitreally.

2. The method of claim 1 wherein the frequency less than the recommended frequency is less than seven doses every twelve months.

3. The method of claim 1 wherein the administering of an anti-VEGF agent to a subject is performed intravitreally.

4. A method of reducing the frequency of administration of an anti-VEGF agent to a subject diagnosed with wet age-related macular degeneration, the method comprising: administering a CCR3 inhibitory agent to the subject; administering the anti-VEGF agent to the subject after the administering of the CCR3 inhibitory agent; administering additional subsequent doses of the anti-VEGF agent to the subject at a frequency less than the recommended frequency; and determining whether to administer the additional subsequent doses of the anti-VEGF agent by diagnosing a morphological change in an eye of the subject diagnosed with wet age-related macular degeneration, wherein the subject is refractory to the anti-VEGF agent and the morphological change is selected from clinically relevant increased intraretinal fluid, clinical-relevant increased intraretinal fluid, clinically relevant increased choroidal neovascularization, and clinically relevant increased central retinal pigmental epithelium detachment height; wherein the CCR3 inhibitory agent is represented by the compound 1, (Compound 1)

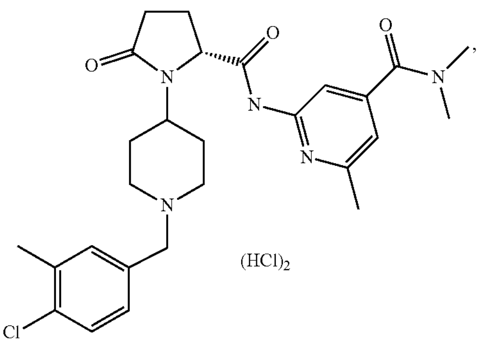

administered orally, wherein the anti-VEGF is selected from the group consisting of aflibercept, ranibizumab, and bevacizumab, and is administered intravitreally.

5. The method of claim 1 wherein the administering the anti-VEGF agent to the subject after the administering of the CCR3 inhibitory agent commences with administration of a loading dose of the anti-VEGF agent.

6. A method of treating a subject suffering from a retina-associated disease, the method comprising administering an anti-VEGF agent to a subject suffering from a retina-associated disease and previously treated with a CCR3 inhibitory agent, wherein the anti-VEGF agent is administered at a frequency less than the recommended frequency for the anti-VEGF agent and the subject is refractory to the anti-VEGF agent; wherein the CCR3 inhibitory agent is represented by the compound 1, (Compound 1)

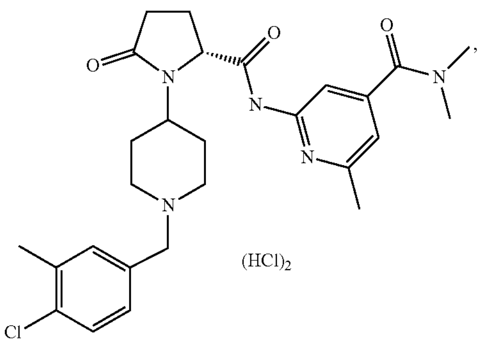

administered orally, wherein the anti-VEGF is selected from the group consisting of aflibercept, ranibizumab, and bevacizumab, and is administered intravitreally.

7. The method of claim 6 wherein the subject was treated with the CCR3 inhibitory agent within six months of administration of the anti-VEGF agent.

8. The method of claim 6 wherein the frequency less than the recommended frequency is less than seven doses every twelve months.

9. The method of claim 6 wherein the administering of an anti-VEGF agent to a subject is performed intravitreally.

* * * * *